US00RE43140E

(19) United States
(12) Reissued Patent
Khan et al.

(10) Patent Number: US RE43,140 E
(45) Date of Reissued Patent: *Jan. 24, 2012

(54) IMMUNOREGULATOR

(75) Inventors: Nisar Ahmed Khan, Rotterdam (NL); Robbert Benner, Barendrecht (NL)

(73) Assignee: Biotempt B.V., Koekange (NL)

( * ) Notice: This patent is subject to a terminal disclaimer.

(21) Appl. No.: 13/065,318

(22) Filed: Mar. 17, 2011

Related U.S. Patent Documents

Reissue of:
(64) Patent No.: 7,365,155
Issued: Apr. 29, 2008
Appl. No.: 10/262,522
Filed: Sep. 30, 2002

U.S. Applications:
(63) Continuation of application No. PCT/NL01/00259, filed on Mar. 29, 2001.

(30) Foreign Application Priority Data

Mar. 29, 2000 (EP) ..... 00201139

(51) Int. Cl.
*A61K 38/04* (2006.01)
*C07K 5/00* (2006.01)

(52) U.S. Cl. ..... 530/330; 424/185.1

(58) Field of Classification Search ..... None
See application file for complete search history.

(56) References Cited

U.S. PATENT DOCUMENTS

| | | | | |
|---|---|---|---|---|
| 4,571,336 | A | 2/1986 | Houck et al. | |
| 4,855,285 | A * | 8/1989 | Stevens | 514/12 |
| 4,977,244 | A | 12/1990 | Muchmore et al. | |
| 5,055,447 | A | 10/1991 | Palladino et al. | |
| 5,308,834 | A | 5/1994 | Scott et al. | |
| 5,380,668 | A | 1/1995 | Herron | |
| 5,436,270 | A | 7/1995 | Wang | |
| 5,650,489 | A | 7/1997 | Lam et al. | |
| 5,677,275 | A | 10/1997 | Lunardi-Iskandar et al. | |
| 5,700,781 | A | 12/1997 | Harris | |
| 5,801,193 | A | 9/1998 | Ojo-Amaize et al. | |
| 5,837,478 | A | 11/1998 | Gallatin et al. | |
| 5,851,997 | A | 12/1998 | Harris | |
| 5,854,004 | A | 12/1998 | Czernilofsky et al. | |
| 5,877,148 | A | 3/1999 | Lunardi-Iskandar et al. | |
| 5,958,413 | A | 9/1999 | Anagnostopulos et al. | |
| 5,968,513 | A | 10/1999 | Gallo et al. | |
| 5,972,924 | A | 10/1999 | Keep et al. | |
| 5,981,486 | A | 11/1999 | Matsushima et al. | |
| 5,994,126 | A * | 11/1999 | Steinman et al. | 435/325 |
| 5,997,871 | A | 12/1999 | Gallo et al. | |
| 6,051,596 | A | 4/2000 | Badger | |
| 6,150,500 | A | 11/2000 | Salerno | |
| 6,211,151 | B1 | 4/2001 | Sikiric et al. | |
| 6,310,041 | B1 | 10/2001 | Haddox et al. | |
| 6,319,504 | B1 | 11/2001 | Gallo et al. | |
| 6,361,992 | B1 | 3/2002 | Szkudlinski et al. | |
| 6,489,296 | B1 | 12/2002 | Grinnell et al. | |
| 6,507,788 | B1 | 1/2003 | Camara y Ferrer et al. | |
| 6,583,109 | B1 | 6/2003 | Gallo et al. | |
| 6,586,403 | B1 | 7/2003 | Mathison et al. | |
| 6,596,688 | B1 | 7/2003 | Gallo et al. | |
| 6,620,416 | B1 | 9/2003 | Gallo et al. | |
| 6,630,138 | B2 | 10/2003 | Gerlitz et al. | |
| 6,642,201 | B1 | 11/2003 | Khavinson et al. | |
| 6,645,934 | B1 | 11/2003 | Rodemann et al. | |
| 6,699,656 | B2 | 3/2004 | Gallo et al. | |
| 6,727,227 | B1 | 4/2004 | Khavinson | |
| 6,844,315 | B2 | 1/2005 | Khan et al. | |
| 6,921,751 | B1 | 7/2005 | Khan et al. | |
| 7,094,760 | B2 | 8/2006 | Mathison et al. | |
| 7,175,679 | B2 | 2/2007 | Khan et al. | |
| 7,358,330 | B2 | 4/2008 | Khan et al. | |
| 7,402,322 | B2 | 7/2008 | Khan et al. | |
| 7,501,391 | B2 | 3/2009 | Khan et al. | |
| 7,517,529 | B2 | 4/2009 | Khan et al. | |
| 7,524,820 | B1 | 4/2009 | Khan et al. | |
| 7,560,433 | B2 | 7/2009 | Khan et al. | |
| 7,576,174 | B2 | 8/2009 | Benner et al. | |
| 7,662,776 | B2 | 2/2010 | Khan et al. | |
| 7,786,084 | B2 | 8/2010 | Benner et al. | |
| 7,795,226 | B2 | 9/2010 | Benner et al. | |
| 2002/0041871 | A1 | 4/2002 | Brudnak | |
| 2002/0064501 | A1 | 5/2002 | Khan et al. | |
| 2002/0147306 | A1 | 10/2002 | Lin et al. | |

(Continued)

FOREIGN PATENT DOCUMENTS

| | | | |
|---|---|---|---|
| EP | 0 572 688 | | 5/1997 |
| EP | 1 138 692 | A1 | 10/2001 |
| EP | 1 300 418 | | 4/2003 |
| GB | 2 194 886 | A | 3/1988 |
| WO | WO 92/20795 | A1 | 11/1992 |
| WO | WO 96/04008 | | 2/1996 |
| WO | WO 96/33218 | | 10/1996 |
| WO | WO 97/49373 | | 12/1997 |
| WO | WO 97/49418 | | 12/1997 |
| WO | WO 97/49432 | | 12/1997 |

(Continued)

OTHER PUBLICATIONS

Hummel, R.P., et al. Topical and Systemic Antibacterial Agents in the Treatment of Burns. Annals Surg. 1970;173(3):370-384.*

Lider, O., et al. Suppression of Experimental Autoimmune Diseases and Prolongation of Allograft Survival by Treatment of Animals with Low Doses of Heparin. J. Clin. Invest. 1989;83:752-756.*

Abeyama et al., A role of NF-κB-dependent gene transactivation in sunburn. The Journal of Clinical Investigation, vol. 105, No. 12, pp. 1751-1759, Jun. 2000.

Baeuerle et al., "Function and Activation of NF-ΘB in the Immune System," Annu. Rev. Immunol., 1994, pp. 141-179, vol. 12.

(Continued)

*Primary Examiner* — Gerald R Ewoldt
(74) *Attorney, Agent, or Firm* — TraskBritt

(57) ABSTRACT

The invention relates to the field of immunology, more specifically to the field of immune-mediated disorders such as allergies, auto-immune disease, transplantation-related disease or inflammatory disease. The invention provides among others an immunoregulator (NMPF), use of an NMPF in preparing a pharmaceutical composition for treating an immune-mediated disorder, a pharmaceutical composition and a method for treating an immune-mediated disorder.

5 Claims, 36 Drawing Sheets

U.S. PATENT DOCUMENTS

| | | | |
|---|---|---|---|
| 2002/0155106 | A1 | 10/2002 | Hammond |
| 2003/0049273 | A1 | 3/2003 | Gallo et al. |
| 2003/0113733 | A1 | 6/2003 | Khan et al. |
| 2003/0119720 | A1 | 6/2003 | Khan et al. |
| 2003/0148955 | A1 | 8/2003 | Pluenneke |
| 2003/0166556 | A1 | 9/2003 | Khan et al. |
| 2003/0186244 | A1 | 10/2003 | Margus et al. |
| 2003/0212253 | A1 | 11/2003 | Hammond et al. |
| 2003/0215434 | A1 | 11/2003 | Khan et al. |
| 2003/0219425 | A1 | 11/2003 | Khan et al. |
| 2003/0220257 | A1 | 11/2003 | Benner et al. |
| 2003/0220258 | A1 | 11/2003 | Benner et al. |
| 2003/0220259 | A1 | 11/2003 | Benner et al. |
| 2003/0220260 | A1 | 11/2003 | Khan et al. |
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |
| 2005/0119184 | A1 | 6/2005 | Khan et al. |

FOREIGN PATENT DOCUMENTS

| | | | |
|---|---|---|---|
| WO | WO 97/49721 | | 12/1997 |
| WO | WO 98/06742 | | 2/1998 |
| WO | WO 98/34631 | A1 | 8/1998 |
| WO | WO 98/35691 | | 8/1998 |
| WO | WO 99/31227 | | 6/1999 |
| WO | WO 99 59617 | | 11/1999 |
| WO | WO 00/17348 | | 3/2000 |
| WO | WO 01/10907 | A2 | 2/2001 |
| WO | WO 01/11048 | A2 | 2/2001 |
| WO | WO 0110457 | A2 | 2/2001 |
| WO | WO 01/29067 | | 4/2001 |
| WO | WO 01/29069 | A1 | 4/2001 |
| WO | WO 01/36454 | A1 | 5/2001 |
| WO | WO 01/51508 | A1 | 7/2001 |
| WO | WO 01/68113 | A1 | 9/2001 |
| WO | WO 01/72831 | | 10/2001 |
| WO | WO 01/83554 | A2 | 11/2001 |
| WO | WO 02/085117 | | 10/2002 |
| WO | WO 03/029292 | A2 | 4/2003 |

OTHER PUBLICATIONS

Epinat et al., "Diverse agents act at multiple levels to inhibit the Rel/NF-kappaB signal transduction pathway," Oncogene, 1999, pp. 6896-6909, vol. 18.

Gould, Salt selection for basic drugs, Int. J. Pharm., 1986, pp. 201-217, vol. 33.

Hierholzer et al., Essential role of induced nitric oxide in the initiation of the inflammatory response after hemorrhagic shock, J. Exp. Med., Mar. 1998, pp. 917-928, vol. 187, No. 6.

Ichiyama et al., Systemically administered alpha-melanocyte-stimulating peptides inhibit NF-kappaB activation in experimental brain inflammation, Brain Research, Jul. 1999, pp. 31-37, vol. 836.

Lunardi-Iskandar et al., "Effects of a urinary factor from women in early pregnancy on HIV-a, SIV and associated disease," Nature Medicine, pril 1998, pp. 428-434, vol. 4, No. 4.

Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.

Merck Index, 17th ed. 1999, pp. 1145-1146, 1841-1848, 2539, 2551.

Samaniego et al., "Induction of Programmed Cell Death in Kaposi's Sarcoma Cells by Preparations of Human Chorionic Gonadotropin," Journal of the National Cancer Institute, Jan. 20, 1999, pp. 135-143, vol. 91, No. 2.

Wallraff et al., Urinary Excretion of Amino Acids in Pregnancy, J. Clinc. Invest., 1950, pp. 1542-1544, vol. 29.

Wu et al., Gonadotropin-Releasing Hormone (GNRH) Cleavage Products are Involved in the Regulation of GNRH Gene Expression in the GT1-7 Neuronal Cell Line, Society for Neuroscience Abstracts, Nov. 4, 2000, pp. 7.8, XP009091566, vol. 26, No. 1-2.

Lang et al., "Induction of apoptosis in Kaposi's sarcoma spindle cell cultures by the subunits of human chorionic gonadotropin", *AIDS* 1997, vol. 11, No. 11, pp. 1333-1340.

Iskandar et al., "Effects of a urinary factor from a women in early pregnancy on HIV-1. SIV and associated disease", *Nature Medicine,* Apr. 1998, vol. 4, No. 4, pp. 428-434.

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy S., et al., "The Role of Nuclear Factor-ΘB in Cytokine Gene Regulation," 17 Am. J. Respir. Cell Mol. Biol. 3-9 (1997).

Connelly et al., Biphasic Regulation of NF-ΘB Activity Underlies the Pro- and Anti-Inflammatory Actions of Nitric Oxide, The Journal of Immunology, 2001, pp. 3873-3881, 166, The American Association of Immunologists, USA.

Friedlander, Tackling anthrax, Nature, Nov. 8, 2001, pp. 160-161, vol. 414.

Medzhitov, Toll-like Receptors and Innate Immunity, Nature Reviews/Immunology. Nov. 2001, pp. 135-145, vol. 1.

Christman et al., Nuclear factor kappaB: a pivotal role in the systemic inflammatory response syndrome and new target for therapy, Intens Care Med, 1998, pp. 1131-1138, vol. 24.

Jyonouchi et al., Proinflammatory and regulatory cytokine production associated with innate and adaptive immune responses in children with autism spectrum disorders and developmental regression, J Neuroim., 2001, pp. 170-179, vol. 120.

Kanungo et al., Advanced Maturation of Heteropneustes Fossilis (Bloch) by Oral Administration of Human Chorionic Gonadotropin, J. Adv. Zool., 1999, pp. 1-5, vol. 20.

Rohrig et al., Growth-stimulating Influence of Human Chorionic Gonadotropin (hCG) on Plasmodium flaciparum in vitro, Zentralblatt Bakt, 1999, pp. 89-99, vol. 289.

Tak et al, NF-kappaB: a key role in flammatory diseases, J Clin Invest., 2001, pp. 7-11, vol. 107.

Tovey et al., Mucosal Cytokine Therapy: Marked Antiviral and Antitumor Activity, J. Interferon Cytokine Res., 1999, pp. 911-921, vol. 19.

Keller, S., et al., "Human Chorionic Gonadotropin (hCG) Is a Potent Angiogenic Factor for Uterine Endothelial Cells in Vitro," 20(5-6) PLACENTA, p. A37 (Jul. 1999).

Khan, Nisan A., et al., "Inhibition of Diabetes in NOD Mice by Human Pregnancy Factor," 62(12) Human Immunology 1315-1323 (Dec. 2001).

Khan, Nisar A., et al., "Inhibition of Septic Shock in Mice by an Oligopeptide From the β-Chain of Human Chorionic Gonadotrophin Hormone," 63(1) Human Immunology 1-7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881-886, vol. 118, No. 3.

Muchmore et al., Purification and Characterization of a Mannose-Containing Disaccharide Obtained from Human Pregnancy Urine, Journal of Experimental Medicine, Dec. 1984, pp. 1672-1685, vol. 160.

Patil, A., et al., "The Study of the Effect of Human Chorionic Gonadotrophic (HCG) Hormone on the Survival of Adrenal Medulla Transplant in Brain. Preliminary Study," 87 Acta Neurochir (WIEN) 76-78 (1987).

Slater, Lewis et al., "Decreased Mortality of Murine Graft-Versus-Host Disease by Human Chorionic gonadotropin," 23(1) Transplantation 103-104 (Jan. 1977).

Wulczyn, F. Gregory, et al., "The NF-κB/Rel and IκB gene families: mediators of immune response and inflammation," 74(12) J. Mol. Med. 749-769 (1996).

Yamamoto, Y., et al., "Role of the NF-κB Pathway in the Pathogenesis of Human Disease States," 1(3) Current Molecular Medicine 287-296 (Jul. 2001).

Ivanov et al., "Hemoglobin as a Source of Endogenous Bioactive Peptides: The Concept of Tissue-Specific Peptide Pool," Biopolymers, 1997, pp. 171-188, vol. 39.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.
Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.
Khavinson et al., "Inductive Activity of Retinal Peptides," Bulletin of Experimental Biology and Medicine, Nov. 2002, pp. 482-484, vol. 134, No. 5.
Khavinson et al., "Mechanisms Underlying Geroprotective Effects of Peptides," Bulletin of Experimental Biology and Medicine, Jan. 2002, pp. 1-5, vol. 133, No. 1.
Khavinson et al., "Peptide Promotes Overcoming of the Division Limit in Human Somatic Cell," Bulletin of Experimental Biology and Medicine, May 2004, pp. 503-506, vol. 137, No. 5.
Morozov et al., "Natural and Synthetic Thymic Peptides as Therapeutics for Immune Dysfunction," Int. J. Immunopharmac., 1997, pp. 501-505, vol. 19, No. 9/10.
Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

* cited by examiner

IMMUNOREGULATOR

Matter enclosed in heavy brackets [ ] appears in the original patent but forms no part of this reissue specification; matter printed in italics indicates the additions made by reissue.

RELATED APPLICATION

This application is a continuation of co-pending International Application No. PCT/NL01/00259, (International Publication No. WO 01/72831 A2) filed [Mar. 3, 2001] *Mar. 29, 2001*, designating the United States of America, the contents of which are incorporated by this reference.

FIELD OF THE INVENTION

The invention relates to the field of immunology, more specifically to the field of immune-mediated disorders such as allergies, auto-immune disease, transplantation-related disease or inflammatory disease.

BACKGROUND

The immune system produces cytokines and other humoral factors to protect the host when threatened by inflammatory agents, microbial invasion, or injury. In most cases this complex defence network successfully restores normal homeostasis, but at other times the immunological mediators may actually prove deleterious to the host. Some examples of immune disease and immune system-mediated injury have been extensively investigated including anaphylactic shock, autoimmune disease, and immune complex disorders.

Recent advances in humoral and cellular immunology, molecular biology and pathology have influenced current thinking about auto-immunity being a component of immune-mediated disease. These advances have increased our understanding of the basic aspects of antibody, B-cell, and T-cell diversity, the generation of innate (effected by monocytes, macrophages, granulocytes, natural killer cells, mast cells, γδ T cells, complement, acute phase proteins, and such) and adaptive (T and B cells and antibodies) or cellular and humoral immune responses and their interdependence, the mechanisms of (self)-tolerance induction and the means by which immunological reactivity develops against auto-antigenic constituents.

Since 1900, the central dogma of immunology has been that the immune system does not normally react to self. However, it has recently become apparent that auto-immune responses are not as rare as once thought and that not all auto-immune responses are harmful; some responses play a distinct role in mediating the immune response in general. For example, certain forms of auto-immune response such as recognition of cell surface antigens encoded by the major histocompatibility complex (MHC) and of anti-idiotypic responses against self idiotypes are important, indeed essential, for the diversification and normal functioning of the intact immune system.

Apparently, an intricate system of checks and balances is maintained between various subsets of cells (i.e. T-cells) of the immune system, thereby providing the individual with an immune system capable of coping with foreign invaders. In that sense, auto-immunity plays a regulating role in the immune system.

However, it is now also recognised that an abnormal auto-immune response is sometimes a primary cause and at other times a secondary contributor to many human and animal diseases. Types of auto-immune disease frequently overlap, and more than one auto-immune disorder tends to occur in the same individual, especially in those with auto-immune endocrinopathies. Auto-immune syndromes may be mediated with lymphoid hyperplasia, malignant lymphocytic or plasma cell proliferation and immunodeficiency disorders such as hypogammaglobulinaemie, selective Ig deficiencies and complement component deficiencies.

Auto-immune diseases, such as systemic lupus erythematosus, diabetes, rheumatoid arthritis, post-partum thyroid dysfunction, auto-immune thromocytopenia, to name a few, are characterised by auto-immune responses, for example directed against widely distributed self-antigenic determinants, or directed against organ- or tissue specific antigens. Such disease may follow abnormal immune responses against only one antigenic target, or against many self antigens. In many instances, it is not clear whether auto-immune responses are directed against unmodified self-antigens or self-antigens that have been modified (or resemble) any of numerous agents such as viruses, bacterial antigens and haptenic groups.

There is as yet no established unifying concept to explain the origin and pathogenesis of the various auto-immune disorders. Studies in experimental animals support the notion that auto-immune diseases may result from a wide spectrum of genetic and immunological abnormalities which differ from one individual to another and may express themselves early or late in life depending on the presence or absence of many superimposed exogenous (viruses, bacteria) or endogenous (hormones, cytokines, abnormal genes) accelerating factors.

It is evident that similar checks and balances that keep primary auto-immune disease at bay are also compromised in immune mediated disorders, such as allergy (asthma), acute inflammatory disease such as sepsis or septic shock, chronic inflammatory disease (i.e rheumatic disease, Sjögrens syndrome, multiple sclerosis), transplantation-related immune responses (graft-versus-host-disease, post-transfusion thrombocytopenia), and many others wherein the responsible antigens (at least initially) may not be self-antigens but wherein the immune response to said antigen is in principle not wanted and detrimental to the individual. Sepsis is a syndrome in which immune mediators, induced by for example microbial invasion, injury or through other factors, induce an acute state of inflammation which leads to abnormal homeostasis, organ damage and eventually to lethal shock. Sepsis refers to a systemic response to serious infection. Patients with sepsis usually manifest fever, tachycardia, tachypnea, leukocytosis, and a localised site of infection. Microbiologic cultures from blood or the infection site are frequently, though not invariably, positive. When this syndrome results in hypotension or multiple organ system failure (MOSF), the condition is called sepsis or septic shock. Initially, micro-organisms proliferate at a nidus of infection. The organisms may invade the bloodstream, resulting in positive blood cultures, or might grow locally and release a variety of substances into the bloodstream. Such substances, when of pathogenic nature are grouped into two basic categories: endotoxins and exotoxins. Endotoxins typically consist of structural components of the micro-organisms, such as teichoic acid antigens from staphylococci or endotoxins from gram-negative organisms μlike LPS). Exotoxins (e.g., toxic shock syndrome toxin-1, or staphlococcal enterotoxin A, B or C) are synthesised and directly released by the micro-organisms.

As suggested by their name, both of these types of bacterial toxins have pathogenic effects, stimulating the release of a large number of endogenous host-derived immunological mediators from plasma protein precursors or cells (monocytes/macrophages, endothelial cells, neutrophils, T cells, and others).

It is in fact generally these immunological mediators which cause the tissue and organ damage associated with sepsis or septic shock. Some of these effects stem from direct mediator-induced injury to organs. However, a portion of shock-associated-organ dysfunction is probably due to mediator-induced abnormalities in vasculature, resulting in abnormalities of systemic and regional blood flow, causing refractory hypotension or MOSF (Bennett et al.).

The non-obese diabetic (NOD) mouse is a model for auto-immune disease, in this case insulin-dependent diabetes mellitus (IDDM) which main clinical feature is elevated blood glucose levels (hyperglycemia). Said elevated blood glucose level is caused by auto-immune destruction of insulin-producing β cells in the islets of Langerhans of the pancreas (Bach et al. 1991, Atkinson et al. 1994). This is accompanied by a massive cellular infiltration surrounding and penetrating the islets (insulitis) composed of a heterogeneous mixture of CD4+ and CD8+ T lymphocytes, B lymphocytes, macrophages and dendritic cells (O'Reilly et al. 1991).

The NOD mouse represents a model in which auto-immunity against beta-cells is the primary event in the development of IDDM. Diabetogenesis is mediated through a multifactorial interaction between a unique MHC class II gene and multiple, unlinked, genetic loci, as in the human disease Moreover, the NOD mouse demonstrates beautifully the critical interaction between heredity and environment, and between primary and secondary auto-immunity, its clinical manifestation is for example depending on various external conditions, most importantly of the micro-organism load of the environment in which the NOD mouse is housed.

As for auto-immunity demonstrable in NOD mice, most antigen-specific antibodies and T-cell responses are measured after these antigens were detected as self-antigens in diabetic patients. Understanding the role these auto-antigens play in NOD diabetes may further allow to distinguish between pathogenic auto-antigens and auto-immunity that is an epiphenomenon.

In general, T lymphocytes play a pivotal role in initiating the immune mediated disease process (Sempe et al. 1991, Miyazaki et al. 1985, Harada et al. 1986, Makino et al. 1986). CD4+ T-cells can be separated into at least two major subsets Th1 and Th2. Activated Th1 cells secrete IFN-γ and TNF-α, while Th2 cells produce IL-4, IL-S and IL-10. Th1 cells are critically involved in the generation of effective cellular immunity, whereas Th2 cells are instrumental in the generation of humoral and mucosal immunity and allergy, including the activation of eosinophils and mast cells and the production of IgE (Abbas et al. 1996). A number of studies have now correlated diabetes in mice and human with Th1 phenotype development (Liblau et al. 1995, Katz et al. 1995). On the other hand, Th2 T cells are shown to be relatively innocuous. Some have even speculated that Th2 T cells in fact, may be protective. Katz et al. have shown that the ability of CD4+ T cells to transfer diabetes to naïve recipients resided not with the antigen specificity recognised by the TCR per se, but with the phenotypic nature of the T cell response. Strongly polarised Th1 T cells transferred disease into NOD neonatal mice, while Th2 T cells did not, despite being activated and bearing the same TCR as the diabetogenic Th1 T cell population. Moreover, upon co-transfer, Th2 T cells could not ameliorate the Th1-induced diabetes, even when Th2 cells were co-transferred in 10-fold excess (Pakala et al. 1997).

The incidence of sepsis or septic shock has been increasing since the 1930's, and all recent evidence suggests that this rise will continue. The reasons for this increasing incidence are many: increased use of invasive devices such as intravascular catheters, widespread use of cytotoxic and immunosuppressive drug therapies for cancer and transplantation, increased longevity of patients with cancer and diabetes who are prone to develop sepsis, and an increase in infections due to antibiotic-resistant organisms. Sepsis or septic shock is the most common cause of death in intensive care units, and it is the thirteenth most common cause of death in the United States. The precise incidence of the disease is not known because it is not reportable; however, a reasonable annual estimate for the United States is 400,000 bouts of sepsis, 200,000 cases of septic shock, and 100,000 deaths from this disease.

Various micro-organisms, such as Gram-negative and Gram-positive bacteria, as well as fungi, can cause sepsis and septic shock. Certain viruses and rickettsiae probably can produce a similar syndrome. Compared with Gram-positive organisms, Gram-negative bacteria are somewhat more likely to produce sepsis or septic shock. Any site of infection can result in sepsis or septic shock. Frequent causes of sepsis are pyelonephritis, pneumonia, peritonitis, cholangitis, cellulitis, or meningitis. Many of these infections are nosocomial, occurring in patients hospitalised for other medical problems. In patients with normal host defences, a site of infection is identified in most patients. However, in neutropenic patients, a clinical infection site is found in less than half of septic patients, probably because small, clinically inapparent infectious in skin or bowel can lead to bloodstream invasion in the absence of adequate circulating neutrophils. Clearly there is a need to protect against sepsis or septic shock in patients running such risks.

Recently, considerable effort has been directed toward identifying septic patients early in their clinical course, when therapies are most likely to be effective. Definitions have incorporated manifestations of the systemic response to infection (fever, tachycardia, tachypnea, and leukocytosis) along with evidence of organ system dysfunction (cardiovascular, respiratory, renal, hepatic, central nervous system, hematologic, or metabolic abnormalities). The most recent definitions use the term systemic inflammatory response syndrome (SIRS) emphasising that sepsis is one example of the body's immunologically-mediated inflammatory responses that can be triggered not only by infections but also by non-infectious disorders, such as trauma and pancreatitis (for interrelationships among systemic inflammatory response (SIRS), sepsis, and infection, see Crit. Care Med. 20:864, 1992; For a review of pathogenic sequences of the events in sepsis or septic shock see N Engl J Med 328:1471, 1993).

Toxic shock syndrome toxin (TSST-1) represents the most clinically relevant exotoxin, identified as being the causative agent in over 90% of toxic shock syndrome cases (where toxic shock is defined as sepsis or septic shock caused by super-antigenic exotoxins). Super antigens differ from "regular" antigens in that they require no cellular processing before being displayed on a MHC molecule. Instead they bind to a semi-conserved region on the exterior of the TCR and cause false "recognition" of self antigens displayed on MHC class II (Perkins et al.; Huber et al. 1993). This results in "false" activation of both the T cell and APC leading to proliferation, activation of effector functions and cytokine secretion. Due to the superantigen's polyclonal activation of T cells, a systemic wide shock results due to excessive inflammatory cytokine release. (Huber et al. 1993, Miethke et al. 1992).

The inflammatory cytokines involved in sepsis are similar. These immunological mediators are tumor necrosis factor (TNF), interferon gamma (IFN-gamma), nitric oxide (Nox) and interleukin 1 (IL-1), which are massively released by monocytes, macrophages and other leukocytes in response to bacterial toxins (Bennett et al., Gutierrez-Ramos et al 1997). The release of TNF and other endogenous mediators may lead to several patho-physiological reactions in sepsis, such as fever, leukopenia, thrombocytopenia, hemodynamic changes, disseminated intravascular coagulation, as well as leukocyte infiltration and inflammation in various organs, all of which may ultimately lead to death. TNF also causes endothelial cells to express adhesion receptors (selecting) and can activate neutrophils to express ligands for these receptors which help neutrophils to adhere with endothelial cell surface for adherence, margination, and migration into tissue inflammatory foci (Bennett et al.). Blocking the adhesion process with monoclonal antibodies prevents tissue injury and improves survival in certain animal models of sepsis or septic shock (Bennett et al.).

These findings, both with auto-immune disease, as well as with acute and chronic inflammatory disease, underwrite the postulated existence of cells regulating the balance between activated Th-sub-populations. Possible disturbances in this balance that are induced by altered reactivity of such regulatory T cell populations can cause immune-mediated diseases, which results in absence or over-production of certain critically important cytokines (O'Garra et al. 1997). These Th-sub-populations are potential targets for pharmacological regulation of immune responses.

In general, immune mediated disorders are difficult to treat. Often, broad-acting medication is applied, such as treatment with corticosteroids or any other broad acting anti-inflammatory agent that in many aspects may be detrimental to a treated individual.

In general there is a need for better and more specific possibilities to regulate the checks and balances of the immune system and treat immune mediated disorders.

SUMMARY OF THE INVENTION

The invention provides among others an immuno-regulator (NMPF) obtainable or derivable from a urinary metabolite of hCG, in particular from nicked forms of b-hCG, or (synthetic) peptide homologues or analogues thereof. These forms of b-hCG have peptide bond cleavages within the b-subunit (Birken et al, Endocrinology 133:1390-1397, 1993). Surprisingly, it has been found that a range of beta-HCG breakdown products provides a cascade of immunoregulators (NPMF) with a host of functions. Even more surprisingly, said immunoregulators are interrelated and derived from one another. The invention provides use of such an NMPF in preparing a pharmaceutical composition for treating an immune-mediated disorder, a pharmaceutical composition and a method for treating an immune-mediated disorder. Immune-mediated disorders as described herein include chronic inflammatory disease, such as diabetes type I or II, rheumatic disease, Sjögrens syndrome, multiple sclerosis), transplantation-related immune responses such as graft-versus-host-disease, post-transfusion thrombocytopenia, chronic transplant rejection, pre-eclampsia, atherosclerosis, asthma, allergy and chronic auto-immune disease, and acute inflammatory disease, such as (hyper)acute transplant rejection, septic shock and acute autoimmune disease. Autoimmune diseases are a group of disorders of in general unknown etiology. In most of these diseases production of autoreactive antibodies and/or autoreactive T lymphocytes can be found. An autoimmune response may also occur as manifestation of viral or bacterial infection and may result in severe tissue damage, for example destructive hepatitis because of Hepatitis B virus infection.

DETAILED DESCRIPTION OF THE INVENTION

Autoimmune diseases can be classified as organ specific or non-organ specific depending on whether the response is primarily against antigens localised in particular organs, or against wide-spread antigens. The current mainstay of treatment of autoimmune diseases is immune suppression and/or, (because of tissue impairment), substitution of vital components like hormone substitution. However, immunosuppressive agents such as steroids or cytostatic drugs have significant side effects, which limits their application. Now, the use of more specific immunoregulatory drugs is provided by the invention in the treatment of autoimmune disease and other inflammations. Based on the immunoregulatory properties, e.g. the capacities to regulate the Th1/Th2 ratio, to modulate dendritic cell differentiation, their low side-effect profile, and the beneficial clinical effects, etc., it shows these urinary metabolite preparations or synthetic analogues thereof to be very helpful in the treatment of patients with immune-mediated inflammation, such autoimmune disease.

A non-limiting list of an immune diseases includes:

Hashimoto's thyroditis, primary mysxoedema thyrotoxicosis, pernicious anaemia, autoimmune atrophic gastritis, Addison's disease, premature menopause, insulin-dependent diabetes mellitus, stiff-man syndrome, Goodpasture's syndrome, myasthenia gravis, male infertility, pemphigus vulgaris, pemphigoid, sympathetic ophthalmia, phacogenic uveitis, multiple sclerosis, autoimmune haemolytic anaemia, idiopathic thrombocytopenic purpura, idiopathic leucopenia, primary biliary cirrhosis, active chronic hepatitis, cryptogenic cirrhosis, ulcerative colitis, Sjögren's syndrome, rheumatoid arthritis, dermatomyositis, polymyositis, scleroderma, mixed connective tissue disease, discoid lupus erythematosus, and systemic lupus erythematosus.

In one embodiment, the invention provides an immunoregulator capable of down-regulating Th1 cell levels and/or upregulating Th2 cell levels, or influencing their relative ratio in an animal, said immunoregulator obtainable from urine or other sources of bodily products, such as serum, whey, placental extracts, cells or tissues. Obtainable herein refers to directly or indirectly obtaining said NMPF from said source, NMPF is for example obtained via chemical synthesis or from animal or plant sources in nature.

In a preferred embodiment, the invention allows regulating relative ratios and/or cytokine activity of lymphocyte, dendritic or antigen presenting cell subset-populations in a diseased animal (e.g. human), preferably where these lymphocyte subset-populations comprise Th1 or Th2, or DC1 or DC2 populations. In general, naive $CD4^+$ helper T lymphocytes (Th) develop into functionally mature effector cells upon stimulation with relevant antigenic peptides presented on the major histocompatibility complex (MHC) class II molecules by antigen-presenting cells (APC). Based on the characteristic set of cytokines produced, Th cells are commonly segregated into at least two different subpopulations: Th1 cells producing exclusively interleukin-2 (IL-2), interferon-gamma (IFN-γ) and lymphotoxin, while Th2 cells produce IL-4, IL-5, IL6, IL10 and IL-13. These Th1 and Th2 subsets appear to be extremes in cytokine production profiles and within these polarized subsets, individual Th cells exhibit differential rather than co-ordinated cytokine gene expression. These subsets develop from common Th precursor cells (Thp) after triggering with relevant peptides into Th0 cells producing an array of cytokines, including IL-2, IL-4, IL-5 and IFN-γ. These activated Th0 cells subsequently polarize into the Th1 or Th2 direction based on the cellular and cytokine composition of their microenvironment. Antigen-presenting cells like the various subsets of dendritic cells besides subsets of macrophages largely determine this polarization into Th1 or Th2 subset development. The Th1-TH2 subsets appear to cross-regulate each other's cytokine production profiles, mainly through IFN-γ and IL-10, and from this concept it was rationalized that disturbances in the balance between these two subsets may result in different clinical manifestations [5]. IL-12 is a dominant factor promoting Th1 subset polarization and dendritic cells and macrophages produce IL-12. Moreover, IL-12 induces IFN-γ production by T cells and natural killer (NK) cells. Recently, it was reported that IL-18 acts synergistically with IL-12 to induce Th1 development. Polarization of Th2 cells is critically dependent on the presence of IL-4 produced by T cells or basophils and mast cells. APC-derived IL-6 has also been shown to induce small amounts of IL-4 in developing Th cells. IL-10 and APC-derived prostaglandin $E_2$ ($PGE_2$) inhibit IL-12 production and Th1 priming.

The Th1-Th2 paradigm has been useful in correlating the function of Th1 cells with cell-mediated immunity (inflammatory responses, delayed type hypersensitivity, and cytotoxicity) and Th2 cells with humoral immunity. In general, among infectious diseases, resistance to intracellular bacteria, fungi, and protozoa is linked to mounting a successful Th1 response. Th1 responses can also be linked to pathology, like arthritis, colitis and other inflammatory states. Effective protection against extracellular pathogens, such as helminths, mostly requires a Th2 response, and enhanced humoral immunity may result in successful neutralisation of pathogens by the production of specific antibodies.

In yet another preferred embodiment, the invention provides an immunoregulator capable of modulating dendritic cell differentiation. The selective outgrowth of Th1 vs. Th2 type cells is dependent on the interaction of precursor Th cells with antigen-presenting cells (APC) carrying the relevant peptide in conjunction with their MHC class II molecules. Cytokines released by the APC and present during the initial interaction between dendritic cells and the pertinent T cell receptor carrying T cells drive the differentiation in to Th1 vs. Th2 subsets. Recently, two different precursors for DC (myeloid vs. lymphoid) have been described in man. Selective development of DC1 from myeloid precursors occurs after stimulation with CD40 Ligand or endotoxin, and results in high production of IL-12. Lymhoid precursors give rise to DC2 cells after CD40 Ligand stimulation, and produced IL-1, IL-6 and IL-10. These cytokines are of prime importance in driving the development of the activated Th cell: IL-4 is required for the outgrowth of Th2 type cells which can be greatly enhanced by the presence of IL-10, while selective differentiation to Th1 type cells is exclusively dependent on the presence of IL-12. Since DC1 are characterized by the production of IL-12, they will primarily induce outgrowth of Th1 type cells, while DC2 produce IL-10 and selectively promote Th2 development in the presence of exogenous IL-4. It is shown herein that an NMPF as provided by the invention is capable of regulating or modulating DC activity and differentiation, thereby allowing selective differentiation and activity of Th1 and/or Th2 cells.

In one embodiment, the invention provides an immunoregulator comprising an active component obtainable from a mammalian chorionic gonadotropin preparation said active component capable of stimulating splenocytes obtained from a non-obese diabetes (NOD) mouse, or comprising an active component functionally related to said active compound, for example allowing regulating or modulating DC activity and differentiation, or allowing selective differentiation and activity of Th1 and/or Th2 cells, in case of chronic inflammation, such as diabetes or chronic transplant rejection for example as shown in the detailed description herein wherein said stimulated splenocytes are capable of delaying the onset of diabetes in a NOD-severe-combined-immunodeficient mouse reconstituted with said splenocytes, or wherein said active component is capable of inhibiting gamma-interferon production of splenocytes obtained from a non-obese diabetes (NOD) mouse, or wherein said active component is capable of stimulating interleukine-4 production of splenocytes obtained from a non-obesediabetes (NOD) mouse.

In another embodiment, the invention provides an immunoregulator comprising an active component obtainable from a mammalian chorionic gonadotropin preparation said active component capable of protecting a mouse against a lipopolysaccharide induced septic shock, for example allowing regulating or modulating DC activity and differentiation, or allowing selective differentiation and activity of Th1 and/or Th2 cells, in case of acute inflammation, such as seen with shock or (hyper)acute transplantation rejection wherein said active component is capable of reducing ASAT or other relevant plasma enzyme levels after or during organ failure, as commonly seen with shock.

Although said immunoregulator according to the invention is easily obtained as urinary gonadotropin metabolite or break down product from urine, for example wherein said mammalian chorionic gonadotropin preparation is derived from urine, other sources, such as serum, cells or tissues comprising gonadotropin are applicable as well. Also from said sources an immunoregulator according to the invention capable of for example regulating Th1 and/or Th2 cell activity, and/or capable of modulating dendritic cell differentiation, is provided. In particular, as immunoregulator a (synthetic) peptide is provided obtainable of derivable from beta-HCG, preferably from nicked beta-HCG. Of course, such a peptide, or functional equivalent thereof is obtainable or derivable from other mammalian gonadotropins, as explained herein earlier. Said peptide is for example capable of protecting against septic shock or other immune-mediated disorders. Preferably, said peptide immunoregulator is obtained from a peptide having at least 10 amino acids such as a peptide having an amino acid sequence MTRVLQGVLPALPQVVC (SEQ ID NO:1) or functional fragment (e.g., a breakdown product) or functional analogue thereof. Functional fragments herein relates to the immunoregulatory effect or activity as for example can be measured in the septic shock or NOD mouse experimental model. Fragments can be somewhat (i.e. 1 or 2 amino acids) smaller or larger on one or both sides, while still providing functional activity.

The invention further provides a method for selecting an immunoregulator comprising determining therapeutic effect of an immunoregulator by subjecting an animal prone to show signs of diabetes to a peptide composition or fraction thereof, and determining the development of diabetes in said animal. Similarly, a method for selecting an immunoregulator comprising determining therapeutic effect of an immunoregulator by subjecting an animal prone to show signs of septic shock to a peptide composition or fraction thereof and determining the development of septic shock in said animal is provided herewith, the septic shock model also being a fast read-out model for the determination of anti-diabetic activity. Preferably, peptide compositions tested in a method according to the invention are obtained from a peptide having at least 10 amino acids such as a peptide having an amino acid sequence MTRVLQGVLPALPQVVC (SEQ ID NO:1) or functional fragment (e.g. a breakdown product) or functional analogue thereof.

Functional fragments herein relates to the immunoregulatory effect or activity as for example can be measured in the septic shock or NOD mouse diabetes experimental model. Fragments can be somewhat (i.e. 1 or 2 amino acids) smaller or larger on one or both sides. Surprisingly, it has been found in the animal test systems as provided herein that a range of beta-HCG breakdown products provides a cascade of peptide immunoregulators with a host of functions. Even more surprisingly, said immunoregulator peptides are interrelated and derived from one another and can also be produced synthetically. The invention provides use of such an immunoregulating peptide in preparing a pharmaceutical composition for treating an immune-mediated disorder, a pharmaceutical composition and a method for treating an immune-mediated disorder. A useful peptide found in a method according to the invention can be further modified or improved for one or more characteristics by peptide synthesis skills known, for example by identification of functional analogues with replacement mapping techniques, by binding-site (PEPSCAN) detection technology and so on, and can comprise D- or L-amino acids or modified amino acids at one or more (or all) places in the desired sequence. Also, peptide derivatives can be made, such as by circularization (for example by providing with (terminal) cysteines, dimerisation or multimerisation, by linkage to lysine or cystein or other side-chains that allow linkage or multimerisation, repeated, brought in tandem configuration, conjugated or otherwise linked to carriers known in the art, if only by a labile link that allows dissociation. Of course, newly developed peptide compositions or derivatives can be tested according to a method as provided herein.

Functional analogue herein not only relates to analogues or homologues peptides from MIF or MIF-like proteins, from LH or PMSG, or gonadotropin-like proteins, be it modified by glycosylation or modification with unidentified amino acids or non-protein amino acids, but also to synthetic peptide analogues that can be made with peptide synthesis skills known, for example by identification of functional analogues with replacement mapping techniques, PEPSCAN detection technology and so on, and can comprise D- or L-amino acids or modified amino acids at one or more (or all) places in the desired sequence. Also, peptides can be circularised (for example by providing with (terminal) cysteines, dimerised or multimerised, by linkage to lysine or cystein or other side-chains that allow linkaage or multimerisation, repeated, brought in tandem configuration, conjugated or otherwise linked to carriers known in the art, if only by a labile link that allows dissociation.

Preferably, an immunoregulator as provided by the invention is obtainable or derivable from a gonadotropin from a pregnant mammal, preferably a human, for example obtainable from a pharmacological preparation prepared to contain (placental) gonadotropins such as pregnant mare serum gonadotropin (PMSG) found in serum of pregnant mares, or pregnant mouse uterus extract (PMUE) extracted from uteri of gravid mice or human chorionic gonadotropin (hCG or HCG) found in blood or urine of pregnant women. An NMPF as provided by the invention can be associated with or without gonadotropin as for example present in the urine of first trimester of pregnancy (NMPF) and in commercial hCG preparations (NMPF) has immune regulatory effects.

In particular, NMPF can inhibit or regulate auto-immune and acute- and chronic-inflammatory diseases. TNF and IFN-gamma are pathologically involved in acute inflammatory disease such as sepsis or septic shock and also in auto-immune and chronic inflammatory diseases. Since NMPF has the ability to regulate T-cell sub-populations and inhibit TNF and IFN-gamma, NMPF can be used to treat, suppress or prevent illumine mediator disorders such as sepsis or septic shock (acute inflammatory disease) as well as auto-immune disease or chronic inflammatory diseases such as systemic lupus erythematosus, diabetes, rheumatic disease, Sjögrens syndrome, multiple sclerosis, post-partum thyroid dysfunction and thyroid dysfunction related dementia's such as Alzheimer's disease, auto-immune thromocytopenia and others, such as allergies and chronic inflammatory disease and transplantation related immune responses.

Furthermore, the invention provides detection of genetic predisposition for immune-mediated disorders, whereby individuals with particular isoforms or amino acid variations in HCG or HCG derived peptides or immunoregulators are predisposed for certain disorders. Once known, it is provided by the invention to provide the genetically predisposed individual with the proper peptide immunoregulator via gene therapy In particular, an immunoregulator according to the invention is provided wherein said functional fragment comprises a peptide having at least 10 amino acids such as having an amino acid sequence, LQGVLPALPQVVC (SEQ ID NO:2) (β45+β48), or VLPALPQVVC (SEQ ID NO:3) (β 48) or LQGVLPALPQ (SEQ ID NO:4) (β 45), or a functional analogue thereof, herein also called NMPF-K.

Said immunoregulator comprising said peptide (or mixtures of peptides) having the desired length of about at least 10 amino acids (and especially when bound to a larger molecule such as when bound via its cysteine to another beta-HCG fragment) generally regulates Th1/Th2 balance as well as innate immunity during an immune mediated disorder. For example septic shock, LPS induced proliferation of splenocytes or diabetes is accelerated or aggravated. Similar activity is provided by a relative short-chain peptide (third immunoregulator, 3-5 amino acids long) that comprises MTRV (SEQ ID NO:5) or MTR or QVVC (SEQ ID NO:6) or VVC or CLQG (SEQ ID NO:7) or LQGV (SEQ ID NO:8) or LQG (and especially when bound to a larger molecule such as when bound via its cysteine to another beta-HCG fragment).

More in particular, a first immunoregulator is provided comprising a functional fragment comprising an amino acid sequence VLPALPQVVC (SEQ ID NO:3) or LQGVLPALPQ (SEQ ID NO:4) or functional analogue thereof which counteracts the regulatory activities of another, second immunoregulator according to the invention wherein said functional fragment comprises an amino acid sequence of from 9 to 6 amino acids (herein also called NMPF-Kb), such as VLPALPQ (SEQ ID NO:9) or GVLPALPQ (SEQ ID NO:10) or GVLPALP (SEQ ID NO:11) or VLPALP (SEQ ID NO:12) or functional analogue thereof, which for example is capable of regulating Th1/Th2 balance as well as innate immunity during an immune mediated disorder such that it is capable to reduce the clinical symptoms seen with immune-mediated disorders, such as septic shock, LPS induced proliferation of splenocytes or diabetes, instead of accelerating or aggravating these symptoms of immune-mediated disease, as for example is shown in the detailed description where NMPF-Kb is capable of protecting a mouse against a lipopolysaccharide induced septic shock, or other acute or chronic immune-mediated disorder as explained herein. As there is an overlap between β45 and β48 peptide (β45; LQGVLPALPQ (SEQ ID NO:4) β48: VLPALPQVVC (SEQ ID NO:3)), we also tested denaturated β45+β48 (LQGVLPALPQVVC (SEQ ID NO:2)) peptide for its effect on LPS induced proliferation (in vitro) and anti-shock activity (in vivo) in BALB/c mice. Our results showed that denaturated β45+β48 peptide inhibits LPS induced proliferation and in vivo septic shock. Breakdown products are generated via proteolysis, for example by lysis with leucocyte elastate, and can undergo further notification such as by the activity of (glutathion) transferases. One of the possible breakdown product of β45+β48 peptide is LQG which resembles glutathione (tripeptide of G, C, and Q with L-glutamate having an isopeptide bond with the amino moiety of L-cysteine). We have shown that NMPF also inhibits (toxin) streptozotocin (SZ) induced diabetes in mice through destruction of beta-cells. One of the mechanisms involved in the destruction of pancreatic beta cells is the formation of reactive radicals (ROS, NO etc.) that also play an important role in the pathogenesis of many other diseases like nephropathy, obstructive nephropathy, acute and chronic renal allograft rejection, auto-immune diseases (like SLE, rheumatoid arthritis, diabetes, MS), AIDS, diseases related to angiogenesis, atherosclerosis, thrombosis and type II diabetes mellitus. So, it is likely that NMPF also acts as 'anti-oxidant'. For example breakdown products of β45+β48 such as LQG or CLQG (SEQ ID NO:7) peptides alone or in combination with certain carbohydrates or modified with unidentified amino acids or with nonprotein amino acids such as β-alanine, γ-Aminobutyric acid, Omithine, etc. posses immunomodulatory activity (NMPF).

Not wishing to be bound by theory, NMPF-K and NMPF-Kb activity can be described as maintaining a Th1/Th2 balance, whereby NMPF-K acts as if binding to an appropriate receptor but not activating it whereas NMPF-Kb is binding to said receptor and activating it to modulate the Th1/Th2 balance in a beneficial way. NMPF-K and NMPF-Kb are therein both ligands of the same or at least a conformationally similar or alike receptor molecule. Said receptor molecule is now also provided, since it and its acitivity are defined herein by said ligands.

For example, our results show that NMPF-Kb inhibits sepsis or septic shock caused by endotoxin or by exotoxin. NMPF-Kb as provided by the invention inhibits or counters immune mediated auto-immune diseases, chronic inflammatory diseases as well as acute inflammatory diseases.

The invention provides a pharmaceutical composition for treating an immune-mediated disorder such as an allergy, auto-immune disease, transplantation-related disease or acute or chronic inflammatory disease and/or provides an immunoregulator (NMPF), for example for stimulating or regulating lymphocyte action comprising an active component said active component capable of stimulating splenocytes obtained from a 20-week-old female non-obese diabetes (NOD) mouse, said stimulated splenocytes delaying the onset of diabetes in a NOD-severe-combined-immunodeficient (NOD.scid) mouse reconstituted at 8 weeks old with said splenocytes, or comprising an active component functionally related thereto.

In one embodiment, the invention provides an pharmaceutical composition or immunoregulator wherein said active component is capable of inhibiting gamma-interferon production or stimulating interleukine-4 production of splenocytes obtained from a 20-week-old female non-obese diabetes (NOD) mouse. Clinical grade preparations of gonadotropins such as hCG and PMSG have since long been used to help treat reproductive failure in situations where follicular growth or stimulation of ovulation is desired. Said preparations are generally obtained from serum or urine, and often vary in degree of purification and relative activity, depending on initial concentration in serum or urine and depending on the various methods of preparation used.

In a particular embodiment, the invention provides a immunoregulator comprising an active component obtainable or derivable from a mammalian CG preparation said active component capable of stimulating splenocytes obtained from a non-obese diabetes (NOD) mouse, or comprising an active component functionally related to said active compound, for example wherein said stimulated splenocytes are capable of delaying the onset of diabetes in a NOD-severe-combined-immunodeficient mouse reconstituted with said splenocytes.

The invention also provides an immunoregulator wherein said active component is capable of inhibiting gamma-interferon production obtained from a non-obese diabetes (NOD) mouse. The invention also provides an immunoregulator wherein said active component is capable of stimulating interleukine-4 production of splenocytes obtained from a non-obese diabetes (NOD) mouse.

An immunoregulator as provided by the invention (NMPF) has immune regulatory effects. In particular, NMPF can inhibit or regulate auto-immune and acute- and chronic-inflammatory diseases. TNF and IFN-gamma are pathologically involved in acute inflammatory disease such as sepsis or septic shock and also in auto-immune and chronic inflammatory diseases. Since NMPF has the ability to regulate T-cell sub-populations and inhibit TNF and IFN-gamma, NMPF can be used to treat, suppress or prevent immune mediator disorders such as sepsis or septic shock (acute inflammatory disease) as well as auto-immune disease or chronic inflammatory diseases such as systemic lupus erythematosus, diabetes, rheumatoid arthritis, post-partum thyroid dysfunction, auto-immune thromocytopenia and others, such as allergies and chronic inflammatory disease (i.e. rheumatic disease, Sjögrens syndrome, multiple sclerosis) and transplantation related immune responses. Our results for example show that NMPF-Kb inhibit sepsis or septic shock caused by endotoxin or by exotoxin. NMPF-Kb as provided by the invention inhibits or counters immune mediated auto-immune diseases, chronic inflammatory diseases as well as acute inflammatory diseases.

The invention thus provides use of an immunoregulator according to the invention for the production of a pharmaceutical composition for the treatment of an immune-mediated-disorder, for example wherein said immune-mediated disorder comprises chronic inflammation, such as diabetes, multiple sclerosis or chronic transplant rejection, wherein said immune-mediated disorder comprises acute inflammation, such as septic or anaphylactic shock or acute or hyper acute transplant rejection, wherein said immune-mediated disorder comprises auto-immune disease, such as systemic lupus erythematosus or rheumatoid arthritis, wherein said immune-mediated disorder comprises allergy, such as asthma or parasitic disease, in particular wherein said immune-mediated disorder comprises an overly strong immune response directed against an infectious agent, such as a virus or bacterium or wherein said immune-mediated disorder comprises pre-eclampsia or another pregnancy related immune-mediated disorder. Use of NMPF-K as contraceptive (e.g. as morning-after-pill or contraceptive vaccine eliciting contraceptive or sterilising antibodies in the vaccinated female mammal) is also provided. Use of NMPF-Kb is provided for facilitating fertility, especially in case where improved implantation is required. Especially, use is provided wherein said treatment comprises regulating innate immunity and/or relative ratios and/or cytokine activity of lymphocyte, dendritic or antigen presenting cell subset-populations in a treated individual, in particular wherein said subset populations comprise Th1 or Th2, or DC1 or DC2 cells. Thus the invention provides a method for treating an immune-mediated-disorder comprising subjecting an animal to treatment with at least one immunoregulator according to the invention, in particular wherein said disorder comprises diabetes or sepsis.

The invention provides also a method for diagnosing or determining the risk of non-pregnancy related immune disorders associated with Th1/Th2 misbalance as demonstrable by a misbalance between NMPF-K and NMPF-Kb, as for example produced or derived from pituitary derived gonadotropin, especially in age-related disease such as auto-immune and chronic inflammatory disease, such as type II diabetes, rheumatic disease, thyroid dysfunction related mental disease such as dementia's like Alzheimers and others, and atherosclerosis and related disease, said method comprising determining in a sample, preferably a blood or urine sample, the relative ratio of a relative long-chain peptide versus a relative short-chain peptide, said peptides derivable from breakdown of beta-HCG, in particular comprising determining the relative ratio of a relative long-chain peptide versus a relative short-chain peptide derived from breakdown a peptide having an amino acid sequence MTRVLQGVLPALPQVVC (SEQ ID NO:1), for example wherein said relative long-chain peptide comprises an amino acid sequence LQGVLPALPQ (SEQ ID NO:4) or GVLPALPQ (SEQ ID NO:10) or VLPALPQ (SEQ ID NO:9) or GVLPALP (SEQ ID NO:11) or VLPALP (SEQ ID NO:12), in particular wherein said relative short-chain peptide comprises MTRV (SEQ ID NO:5) or MTR or PALP (SEQ ID NO:13) or QVVC (SEQ ID NO:6) or VVC or LQGV (SEQ ID NO:8) or LQG. Detection of said long-chain peptides and short chain peptides, be it modified by glycosylation or modification with unidentified amino acids or non-protein amino acids is preferably achieved by immunological detection methods as known in the art.

The invention provides also a method for diagnosing or determining the risk of a pregnancy related immune-mediated disorder such as pre-eclampsia, or other immune-mediated disorder and the outcome of pregnancy and/or pregnancy related immune disease (such as gestation diabetes mellitus (GDM)) comprising determining in a sample, preferably a urine sample, the relative ratio of a relative long-chain peptide versus a relative short-chain peptide, said peptides derivable from breakdown of beta-HCG, in particular comprising determining the relative ratio of a relative long-chain peptide versus a relative short-chain peptide derived from breakdown a peptide having an amino acid sequence MTRVLQGVLPALPQVVC (SEQ ID NO:1), for example wherein said relative long-chain peptide comprises an amino acid sequence LQGVLPALPQ (SEQ ID NO:4) or GVLPALPQ (SEQ ID NO:10) or VLPALPQ (SEQ ID NO:9) or GVLPALP (SEQ ID NO:11), in particular wherein said relative short-chain peptide comprises MTRV (SEQ ID NO:5) or MTR or QVVC (SEQ ID NO:6) or VVC, or LQGV (SEQ ID NO:8) or LQG.

Anecdotal observations and laboratory studies indicated previously that hCG might have an anti-Kapos's sarcoma and anti-human-immunodeficiency-virus effect (Treatment Issues, July/August 1995, page 15). It has been observed that hCG preparations have a direct apoptotic (cytotoxic) effect on Kaposi's sarcoma (KS) in vitro and in immunodeficient patients and mice and a prohematopoetic effect on immunodeficient patients (Lunardi-Iskandar et al., Nature 375, 64-68; Gill et al., New. Eng. J. Med. 335, 1261-1269, 1996; U.S. Pat. No. 5,677,275), and a direct inhibitory antiviral effect on human and simian immunodeficiency virus (HIV and SIV) (Lunardi-Iskandar et al., Nature Med. 4, 428-434, 1998, U.S. Pat. No. 5,700,781). Said cytotoxic and anti-viral effects have also been attributed to an unknown hCG mediated factor (HAF), present in clinical grade preparations of hCG. However, commercial hCG preparations (such as CG-10, Steris Profasi, Pregnyl, Choragon, Serono Profasi, APL), have various effects. Analysis of several of these, (AIDS, 11: 1333-1340, 1997) for example shows that only some (such as CG-10, Steris Profasi) are KS-killing whereas others (Pregnyl, Choragon, Serono Profasi) were not. Secondly, recombinant subunits of ($\alpha$ or $\beta$) hCG were killing but intact recombinant hCH not. It was also found that the killing effect was also seen with lymphocytes. Therapy of KS has recently been directed at using beta-hCG for its anti-tumour effect (Eur. J. Med Res. 21: 155-158, 1997), and it was reported that the beta-core fragment isolated from urine had the highest apoptotic activity on KS cells (AIDS, 11: 1713-721, 1997).

Recently, Gallo et. al. reported anti-Kaposi's Sarcoma, anti-HIV, anti-SIV and distinct hematopoietic effects of clinical grade crude preparations of human chorionic gonadotropin (hCG) (Lunardi-Iskandar et al. 1995, Gill et al. 1996, Lunardi-Iskandar et al. 1998). In contrast to their previous studies, it is also claimed that the anti-tumour and anti-viral activity of hCG preparation is not due to the native hCG heterodimer, including its purified subunits or its major degradation product, the $\beta$-core; instead the active moiety resides in an as yet unidentified hCG mediated factor (HAF). Whatever the true factor may be, these unidentified factors in several hCG preparations have anti-tumour activity through the selective induction of apoptosis, besides direct cytotoxic effects on the tumour cells. Furthermore, they postulated that the anti-tumour activity could not be due to an immune-mediated response, since there was no infiltration of the tumour with mononuclear cells.

Moreover, the reported pro-hematopoietic effect of clinical grade hCG was noted in clinical studies in humans infected with HIV, (Lunardi-Iskandar et al. 1998) indicating that the hematopoietic effect is indirect, and caused by rescuing CD4+cells otherwise killed by HIV through the anti-HIV activity of hCG.

The invention provides an immunoregulator or a pharmaceutical composition for treating an immune-mediated disorder obtainable from a hCG preparation or a fraction derived thereof. The effects of said immunoregulator include a stimulating effect on lymphocyte populations (such as found in peripheral lymphocytes, thymocytes or splenocytes), instead of cytotoxic or anti-viral effects. The invention provides a method for treating an immune-mediated-disorder comprising subjecting an animal to treatment with at least one immunoregulator obtainable from a pregnant mammal. Said treatment can be direct, for example treatment can comprise providing said individual with a pharmaceutical composition, such as a hCG or PMSG preparation, comprising an immunoregulator as provided by the invention. It is also possible to provide said pharmaceutical composition with a fraction or fractions derived from a pregnant animal by for example sampling urine or serum or placental (be it of maternal or foetal origin) or other tissue or cells and preparing said immunoregulator comprising said active component from said urine or serum or tissue or cells by fractionation techniques known in the art (for example by gel permeation chromatograpy) and testing for its active component by stimulating a NOD mouse or its splenocytes as described. In particular, said preparation or component is preferably derived from a pregnant animal since an embryo has to survive a potentially fatal immunological conflict with its mother: developing as an essentially foreign tissue within the womb without triggering a hostile immune attack. So, to prevent this rejection "allograft" the immunological interaction between mother and fetus has to be suppressed, either for instance through lack of fetal-antigen presentation to maternal lymphocytes, or through functional "suppression" of the maternal lymphocytes. If fetal antigens are presented, maternal immune responses would be biased to the less damaging, antibody-mediated T helper 2 (Th2)-type. This would suggest that pregnant women are susceptible to overwhelming infection, which is not the case. Female individuals during pregnancy maintain or even increase their resistance to infection. Moreover, while said individuals normally are more susceptible to immune diseases than male individuals, especially autoimmune diseases, during pregnancy they are more resistant to these diseases.

The invention also provides a method for in vitro stimulation of lymphocytes and transferring said stimulated lymphocytes as a pharmaceutical composition to an animal for treating said animal for an immune mediated disorder. In a particular embodiment of the invention a pharmaceutical composition is provided comprising lymphocytes stimulated in vitro with an immunoregulator provided by the invention.

In a preferred embodiment of the invention, said disorder comprises diabetes, yet other immune mediated disorders, such as acute and chronic inflammation, can also be treated. In yet another preferred embodiment, said disorder comprises sepsis or septic shock. The invention provides a method of treatment for an animal, preferably wherein said animal is human.

In a particular embodiment, a method provided by the invention is further comprising regulating relative ratios and/or cytokine activity or cytokine expression or marker expression of lymphocyte, dendritic or antigen presenting cell subset-populations in said animal, such as subset-populations that comprise Th1 or Th2 cells, or Th3 or Th8 cells, or DC1 or DC2 cells or other effector or regulatory T-cell populations.

The invention also provides an immunoregulator for use in a method according to the invention, and use of said immunoregulator, preferably obtainable from a pregnant mammal, for the production of a pharmaceutical composition for the treatment of an immune-mediated-disorder, preferably selected from a group consisting of allergies, auto-immune disease (such as systemic lupus erythematosus or rheumatoid arthritis), transplantation-related disease and acute (such as septic or anaphylactic shock or acute or hyper acute transplant rejection) and chronic inflammatory disease (such as atherosclerose, diabetes, multiple sclerosis or chronic transplant rejection). Furthermore, the invention provides a use according to the invention wherein said immune-mediated disorder comprises allergy, such as asthma or parasitic disease, or use according to the invention wherein said immune-mediated disorder comprises an overly strong immune response directed against an infectious agent, such as a virus or bacterium. Often in most of these diseases production of autoreactive antibodies and/or autoreactive T lymphocytes can be found mounting or being part of a too strong immune response. This is for example seen with parasitic disease, where IgE production is overly strong or which disease is Th2 dependent, and detrimental for the organism, but also with (myco)bacterial infections such as TBC or leprosy. An autoimmune response may also occur as manifestation of viral or bacterial infection and may result in severe tissue damage, for example destructive hepatitis because of Hepatitis B virus infection, or as seen with lymphocytic choriomeningitis virus (LCMV) infections. Said overly strong immune response is kept at bay with an immunoregulator as provided by the invention. Yet other use as provided by the invention relates to treatment of vascular disease, whereby radical damage (damage caused by radicals) to cells and tissue is prevented or repaired by treatment with NMPF according to the invention; whereby NMPF also acts as antioxidant directly or indirectly. For example, a determining event in the pathogenesis of diabetes I is the destruction of insulin-producing pancreatic beta cells. There is strong evidence that the progressive reduction of the beta-cell mass is the result of a chronic autoimmune reaction. During this process, islet-infiltrating immune cells, islet capillary endothelial cells and the beta cell itself are able to release cytotoxic mediators. Cytokines, and in particular nitric oxide (NO), are potent beta-cell toxic effector molecules. The reactive radical NO mediates its deleterious effect mainly through the induction of widespread DNA strand breaks, other radicals, such as oxygen, through their effects on lymfocyte sub-populations such as Th1 and Th2 cells. This initial damage triggers a chain of events terminating in the death of the beta cell and disarray of the immune response.

Furthermore, an immunoregulator according to the invention is capable of regulating radical induced or directed cell-cell interactions or cell responses, specifically those interactions or responses of an immunological nature, e.g. related to regulating interactions of the innate or adaptive immune system. Not wishing to be bound by theory, there are two arms of the immune system: the innate (non-specific), and adaptive (specific) systems, both of which have cellular and humoral components. Examples of cellular components of the innate immune system are monocytes, macrophages, granulocytes, NK cells, mast cells, gd T cell etc, while, examples of humoral components are lysozyme, complement, acute phase proteins and mannose-binding lectin (MBL). The major cellular components of the adaptive immune system are T and B cells, while examples of humoral components are antibodies. The adaptive system has been studied most because of its specificity, effectiveness at eliminating infection and exclusive presence in higher multicellular organisms. The innate system is often considered primitive and thought to be 'unsophisticated'. However, the innate system not only persists but could also play a critical role in one of the most fundamental immune challenges—viviparity. The innate system instigates an immune response by processing and presenting antigen in association with major histocompatibility complex (MHC) class I and II molecules to lymphocytes. Full response often requires adjuvant (such as endotoxin), which, through interaction with the innate immune system, produce costimulatory surface molecules or cytokines. This determines the biological significance of antigens and communicates this information to the adaptive system. So it instructs the adaptive system to either respond or not. So these two great arms of immune system not only influence each other but also regulate each other at least at the cellular level through for example cytokines and co-stimulatory molecules etc.

There are many physiological conditions and immune pathologies where these two systems are involved separately or in combination. For example, it has been shown that in pregnancy the maternal innate immune system is more stimulated, or for it has been proposed that type II diabetes mellitus is a disease of a chronic hyperactive innate immune system. Another example is the involvement of the innate immune system in listeriosis. Dysregulation in the adaptive immune system may also lead to immune diseases like systemic or organ-specific autoimmunity, allergy, asthma etc, but it can also play a role in the maintenance of pregnancy and in the prevention of "allograft" rejection.

As mentioned above, the adaptive system has been studied most because of its specificity, effectiveness at eliminating infection, and exclusive presence in higher multicellular organisms. Its regulation has also been studied most. For example, it well known that the cytokine micro-environment plays a key role in T helper cell differentiation toward the Th1 or Th2 cell type during immune responses. IL-12 induces Th1 differentiation, whereas IL-4 drives Th2 differentiation. Recently it has also been shown that subsets of dendritic cells (DC1, DC2) provide different cytokine microenvironments that determine the differentiation of either Th1 or Th2 cells. In addition, negative feedback loops from mature T helper cell responses also regulate the survival of the appropriate dendritic cell subset and thereby selectively inhibit prolonged Th1 or Th2 responses. Moreover, development of Th1 responses can be antagonized directly by IL-4 and indirectly by IL-10, which inhibits the production of IL-12 and interferon-g-inducing factor (IGIF) by macrophages stimulated by the innate immune response. Th2 cells dependent on IL-4 to proliferate and differentiate have been implicated in allergic and atopic manifestations, and in addition through their production of IL-4 and IL-10, have been suggested to play a role in tolerance. Specifically, it has been suggested that Th1 to Th2 switch may prevent the development of organ-specific autoimmune pathologies and required for the maintance of pregnancy. Recently it has become clear that distinct subsets of regulatory T cells are responsible for regulating both Th1 and Th2 responses and prevent the development of immune pathologies. One of the common features of many of these regulatory T cells is that their function is at least in part due the action of TGF-beta; this would be in keeping with the ability of TGF-beta to inhibit both Th1 and Th2 development while IL-10 could preferentially inhibit Th1 alone.

The selective outgrowth of Th1 vs. Th2 type cells is dependent on the interaction of precursor Th cells with antigen-presenting cells (APC) carrying the relevant peptide in conjunction with their MHC class II molecules. Cytokines released by the APC and present during the initial interaction between dendritic cells and the pertinent T cell receptor carrying T cells drive the differentiation in to Th1 vs. Th2 subsets. Recently, two different precursors for DC (myeloid vs. lymphoid) have been described in man. Selective development of DC1 from myeloid precursors occurs after stimulation with CD40 Ligand or endotoxin, and results in high production of IL-12. Lymhoid precursors give rise to DC2 cells after CD40 Ligand stimulation, and produced IL-1, IL-6 and IL-10. These cytokines are of prime importance in driving the development of the activated Th cell: IL-4 is required for the outgrowth of Th2 type cells which can be greatly enhanced by the presence of IL-10, while selective differentiation to Th1 type cells is exclusively dependent on the presence of IL-12. Since DC1 are characterized by the production of IL-12, they will primarily induce outgrowth of Th1 type cells, while DC2 produce IL-10 and selectively promote Th2 development in the presence of exogenous IL-4.

NMPF as provided by the invention is able to regulate the Th1 /Th2 balance in vivo (BALB/c, NOD) and in vitro. In dominant Th1 phenotype models like NOD, NMPF (like NMPF-P and its fractions) amongst others down-regulates the IFN-gamma production (in vivo/in vitro) and promote the IL-10 and TGF-beta production, in contrast to IL-4 production, which indicates the induction of regulatory cells like Th3 and Tr1 by NMPF. These regulatory cells may play role in the therapeutic effects of NMPF in immune and inflammatory diseases and immune tolerance. Furthermore, the invention provides an immunoregulator selected by a method according to the invention, a pharmaceutical composition comprising such a selected immunoregulator, and the use of said for the preparation of a pharmaceutical composition for the treatment of an immune-mediated disorder.

Purified NMPF is used to produce monoclonal antibodies and/or other specific reagents thereby facilitating the design of an NMPF-specific quantitative immuno-assay. Also single chain $F_v$ fragments are isolated by using the phage display technology with the use of a phage library containing a repertoire comprising a vast number of different specificities.

The invention further provides a method and a pharmaceutical composition for modulating cardiovascular or circulatory disorders, such as heart failure, brain infarctions, Alzheimer's disease, thrombosis, arteriosclerosis, pregnancy related cardiovascular or circulatory disorders and the like. It has been found that an immunoregulator as described supra has a very beneficial effect on animals, including humans, suffering from a cardiovascular disorder.

An immunoregulator according to the invention also widens the scope of possibilities of dotter treatments. In cases where conventionally such a treatment could not be performed because of risks of an oxygen tension becoming too low, a dotter treatment is now feasible when combined with treatment with an immunoregulator described above. Accordingly, expensive and difficult bypass surgery may in many cases be avoided.

The invention is further explained in the following examples and accompanying discussion without limiting the invention thereto. It is to be noted that these examples discuss implications of the invention of which it will be clear to the skilled person that they provide a general teaching applicable over a broad scope.

EXAMPLE I

Introduction

The immune system has two arms: the non-specific (innate) and specific (adaptive) immune defense, both of which have cellular and humoral components. T and B cells account for the antigen-specific cellular and humoral (antibodies) immune defense. On the other hand, monocytes/macrophages, granulocytes, NK cells, mast cells and likely also gd T cells are the cellular components of the innate immune system, while complement, acute phase proteins, lysozyme and mannose-binding lectin (MBL) are major humoral components of the innate immune system. The adaptive system has been studied most because of its specificity and lasting effectiveness in eliminating infections. The innate system is thought to play a critical role in the most fundamental immune challenge in mammals: viviparity.

The innate system instigates an immune response by processing and presenting antigen in association with major histocompatibility complex (MHC) class I and II molecules to lymphocytes, the so called signal 1. Full responses often require adjuvants (such as endotoxin), which, through interaction with the innate immune system, produce signal 2, in the form of costimulatory surface molecules or cytokines. Signal 2 appears to determine the biological significance of antigens and communicates this information to the adaptive system. In fact, it is believed that this signal 2 instructs the adaptive system to either respond or not (Immunology Today 20, 114-118). So, the innate system is an integral part of the specific immune defense.

During pregnancy there are increased numbers of monocytes and granulocytes from the first trimester onwards. It has been found that, in normal pregnancy, circulating monocytes and granulocytes have activated phenotypes, in some ways comparable with changes observed in systemic sepsis (Am. J. Obstet. Gynecol. 179, 80-86). Others have shown increased monocyte phagocytosis and respiratory burst activity. Monocyte surface expression of the endotoxin receptor CD14 is increased, and in response to endotoxin monocytes from normal pregnant women produce more of the proinflammatory type I cytokine IL-12 (Immunology Today 20, 114-118).

Other studies have similarly found granulocyte activation in pregnancy as well as changes in plasma levels of soluble innate factors typical of an acute phase response (Am J. Reprod. Immunol. Microbiol. 15, 19-23).

During pregnancy the maternal immune system is modulated, resulting in suppression of maternal immune responses against the fetus, while maintaining the mother's resistance to infection. We have shown the presence of immunoregulator (IR, WO99-59617) which we named in this document NMPF (Natural immuno-Modulatory Pregnancy-Factor(s)) that regulate both innate and adaptive immune systems in a stimulatory and antagonistic way (WO99-59617). These factors include, but are not limited to, commercial hCG preparations derived from human pregnancy urine, b-hCG preparations, certain peptides of b-hCG, certain combinations of b-hCG peptides and certain gel filtration chromatography fractions of commercial hCG preparations and human pregnancy urine. Balance in these factors is crucial for proper regulation of the maternal immune system. For example, the over-activation of the innate system can cause problems in the progression of the pregnancy itself. Pre-eclampsia is one of such condition characterized by hyperactivation of the innate immune system. Recently it has been also suggested that the chronic misbalance between the two immune systems could be the basis of type II diabetes (non-insulin dependent diabetes mellitus) and other diseases as well (WO99-59617).

Several cytokines have been proposed to play an important role in balancing the immune system. One such cytokine which plays an important role in the innate immune defense and in the regulation of inflammatory responses is macrophage migration inhibitory factor (MIF).

MIF was originally identified by its ability to prevent the migration of macrophages out of capillary tubes. Since then, the expression of MIF activity has been found at a variety of inflammatory loci, suggesting its role in regulating the function of macrophages in host defense (Science 153, 80-82; J. Exp. Med. 137, 275-288). First described as a T-cell cytokine, recently, MIF is identified to be a peptide also released by pituitary cells in response to infection and stress (Nature 365, 756-759; Nature 377, 68-71). Originally considered to be the target of MIF action, monocytes and macrophages have been found to be a main source of MIF that is released after exposure to bacterial endo- and exotoxins and to cytokines. Once released, MIF induces the expression of proinflammatory mediators by macrophages and activated T cells, thereby strongly promoting inflammatory and immune responses (Nature Medicine 6,164,170). The critical regulatory role of MIF within the immune system is further underscored by the finding that MIF is induced by glucocorticoids and has the unique ability to override the anti-inflammatory and immunosuppressive effects of glucocorticoids on macrophages and T cells. Thus, MIF and glucocorticoids function as a physiological counter-regulatory dyad that controls host inflammatory and immune responses (Proc. Natl. Acad. Sci. USA 93, 7849-7854). Anti-MIF antibodies reduce the inflammation in experimental models of glomerulonephritis, arthritis, and allograft rejection, confirming the role of MIF in the regulation of inflammatory responses. Elevated concentrations of MIF have also been detected in alveolar air spaces of patients with the adult respiratory distress syndrome (ARDS). Recent studies have also shown that MIF is an important mediator of lethal endotoxemia and staphylococcal toxic shock, playing a critical role in the pathogenesis of septic shock. Besides the functions in the immune system, MIF has also other activities. For instance, MIF mRNA and protein are expressed in brain, embryonic eye lens and differentiating epidermal cells, suggesting its pivotal role in the regulation of the neuroendocrine system, cell growth and differentiation. A number of reports showed the presence of MIF in various organs and tissues: dermal vessels constitutively express MIF and can be strongly activated to express MIF in acute/chronic inflammations such as eczema and psoriasis. MIF expression on endothelium may provide an important differentiogenic signal for mononuclear phagocytes on their way to the tissue site.

One of the mechanisms of immune regulation that we detect during pregnancy is through modulation of the innate and adaptive immune defenses by NMPF. By way of example, but not limited to, acting directly or indirectly on regulatory cells of the APC compartment (such as DC1, DC2) or on lymphocytes (regulatory T cells), NMPF biases activated T lymphocytes towards Th2 immune response. The suppression of Th1 immune responses may be compensated by the stimulation of the innate immune defense by NMPF which could explain the maintenance of maternal resistance to infection. Recently, it has been shown that in some instances such compensatory mechanism (stimulation of innate immunity) could be more dominant and may account for abnormal pregnancy: pre-eclampsia.

Pre-eclampsia is a common, pregnancy-specific syndrome defined by clinical findings of elevated blood pressure combined with proteinuria and edema. The incidence has been reported to be between two and seven percent of all pregnancies. The clinical findings become manifested mostly late in pregnancy. The disease can progress rapidly, at times without warning, to a life-threatening disease. Expedient delivery initiates the resolution of pre-eclampsia but is a major cause of fetal and maternal morbidity and mortality.

Roberts et al in their classic article gathered the evidence to invoke activation of maternal endothelium as an underlying process. Generalized maternal endothelial cell dysfunction allowed most, if not all, clinical aspects to be potentially explained by a single, unifying process: hypertension through disturbed endothelial control of vascular tone, fluid retention by increased endothelial permeability, and clotting dysfunction resulting from abnormal endothelial expression of procoagulant. Eclampsia can be ascribed to focal cerebral ischemia resulting from vasoconstriction, consistent with the evidence of changes detected by new cerebral imaging techniques. The liver dysfunction intrinsic to the HELLP (hemolysis, elevated liver enzymes, and low platelet count) syndrome could also be attributed to the effects of acute underperfusion.

Endothelial cells can be activated in several different ways that are potentially relevant to the origins of pre-eclampsia, and several candidate factors have emerged, including free fatty acids, lipoproteins, oxidized lipoproteins or lipid peroxides, tumor necrosis factor alpha (TNF-a), fibronectin degradation products, and deported syncytiotrophoblastic microvillous fragments. The source of the factors that lead to endothelial cell dysfunction has not been determined with certainty, but the evidence points to the placenta.

In addition to endothelial dysfunction there is substantial published evidence that there is systemic activation of the maternal inflammatory cell responses in pre-eclampsia. Both granulocytes and monocytes are activated. There is increased release of the proinflammatory cytokines TNF-a and its 2 soluble receptors, interleukin 6 (IL-6) and soluble phospholipase A2 (an important mediator of inflammatory reactions) into the circulation. It is well known that the clotting system is abnormally activated, and complement systems are similarly affected. Postmortem observations indicate that in some circumstances the lethal pathologic condition resembles that of the Shwartzmann reaction, a particular form of inflammatory response to endotoxin that has been characterized in experimental animals. Since the above mentioned characteristics of pre-eclampsia resemble that of septic shock, we identified that also NMPF (IR) factor(s) are involved in pre-eclampsia that can worsen septic shock or sepsis. We addressed this by using a high dose LPS animal model for septic shock. Since in the urine of pre-eclamptic patients high levels of nicked hCG b-subunits are present, we also tested these nicked subunits to find out whether they worsen septic shock and so behave like MIF, which is an important mediator of lethal endotoxemia and staphylococcal toxic shock.

Material and Methods

NMPF purification: To analyse the NMPF from commercial hCG preparations, we used a Shimadzu HPLC system equipped with Alltech macrosphere size exclusion (GPC) column of 60 Å, 100 Å or 300 Å (250×4.6 mm and 300×7.5 mm). The separation ranges of the columns were 28,000-250, 2500-350,00 and 1,200,000-7,500 Dalton, respectively. External molecular weight standards were employed to calibrate the column elution positions. The markers used were: aprotinin (6,500 Da), cytochrome C (12,400), carbonic anhydrase (29,000), albumin (66,000) and blue dextran (2,000,000).

To analyze NMPF, three different hCG preparations were used: NMPF-PG (Pregnyl; Organon; OSS, The Netherlands), NMPF-A (APL; Weyth Ayerst; Philadelphia, USA) and NMPF-PR (Profasi; Serono, Rome, Italy). As running buffer 50 mM ammonium bicarbonate buffer containing ethanol (5 w, vol/vol) was used. Sample load volume was 10-50 ml for the 250×4.6 mm column and 50-200 ml for the 300×7.5 mm column. The flow rate for the 250×4.6 mm and 300×7.5 mm columns were 0.5 ml/min for 45 min. and 1-2 ml/min for 45 min, respectively.

First trimester pregnancy urine (2 liters) was collected in a bottle from a healthy volunteer and was refrigerated until delivered at the laboratory within 2 days. Upon delivery, 1 gram per liter of sodium azide was added and the pH was adjusted to 7.2-7.4 with sodium hydroxide and allowed to sediment for 1 hour (h) at room temperature (RT). Approximately, 75% of the supernatant was decanted and the remainder close to the precipitate was centrifuged (10 min at 25,000 rpm at 40° C.) to remove sediment and added to the rest of the supernatants. The supernatants were filtered through 0.45 mm in a Minitan (Millipore) transversal filtration set-up. Subsequently, the filtrate (2 liter) was concentrated in an Amicon ultrafiltration set-up equipped with an YM Diopore membrane with a 10 kDa cut-off. The final volume (250 ml) was dialysed against 2 changes of 10 liters of Milli Q water. Next the sample was further concentrated by 10 kDa cut-off in an Amicon ultrafiltration system to a final volume of 3 ml.

Mice used in sepsis or septic shock experiments: Female BALB/c mice of 8-12 weeks of age were used for all experiments. The animals were bred in our facility under specific pathogen-free conditions according to the protocols described in the Report of European Laboratory Animal Science Associations (FELASA) Working group on Animal Health (Laboratory Animals 28: 1-24, 1994).

Injection protocols: For the endotoxin model, BALB/c mice were injected i.p. with 150-300 μg LPS (E. coli 026:B6; Difco Lab., Detroit, Mich., USA). Control groups were treated with PBS i.p. only. To test the effect of NMPF, we treated BALB/c with an optimized dose of 700 IU of different hCG preparations, thereof derived fractions (10-50 mg) or from first trimester pregnancy urine (NMPF-U) for 3 days and then injected with LPS i.p.

In order to determine whether NMPF inhibited shock even after the shock induction, we also treated BALB/c mice with NMPF i.p. after 3, 12, 24 and 36 h of injection with LPS. At different time points semi-quantitative sickness scores and survival rates were noted.

Semi-quantitative sickness measurements: Mice were scored for sickness severity using the following measurement scheme:

1 Percolated fur, but no detectable behaviour differences compared to normal mice.
2 Percolated fur, huddle reflex, responds to stimuli (such as tap on cage), just as active during handling as healthy mouse.
3 Slower response to tap on cage, passive or docile when handled, but still curious when alone in a new setting.
4 Lack of curiosity, little or no response to stimuli, quite immobile.
5 Laboured breathing, inability or slow to self-right after being rolled onto back (moribund, sacrificed).

b-hCG peptide and anti-MIF treatment: Most urinary metabolites of hCG are a nicked form of b-hCG. These forms of b-hCG have peptide bond cleavages within the b-subunit. b48 (VLPALPQVVC (SEQ ID NO:3)) is one such peptide which has been shown to be associated with a natural urinary metabolite of hCG. To test the effect of this peptide on septic shock, we injected BALB/c mice with LPS and treated them 2 h later i.p. with b48-peptide (100 mg). In order to see whether possible breakdown products also have effect on septic shock, we incubated b48-peptide at 37° C. for three h before testing the peptide in the septic shock model in BALB/c mice.

Previously (WO 99-59617), we have shown that NMPF (IR) has also anti-diabetic effect. So in order to test whether b48 peptide has anti-diabetic effect, we performed transfer experiments. Total spleen cells were recovered from diabetic NOD mice and stimulated in vitro in RPMI+ supplemented with 10% FBS with coated anti-CD3 (145-2c11; 25 mg/ml) and IL-2 (50 U/ml) along with 300 IU/ml NMPF (Pregnyl) or b48 peptide (20 mg/ml). Culture flasks were then incubated at 37° C. in 5% of $CO_2$ in air for 48 h. After 48 h cells were twice washed with PBS and $20\times10^6$ cells were i.p. transferred into an 8-wk-old NOD.scid mouse (n=4).

In vitro/ex vivo LPS stimulated proliferation of splenocytes: After 48 h of septic shock induction in BALB/c mice by high dose LPS injection, spleen cells ($1\times10^6$ cells/ml) were recovered and restimulated in vitro with LPS (10 U/ml) in 96-well plates (round bottom). After 24 hours of culture, the LPS stimulated proliferation of splenocytes was measured via [$^3$H]TdR incorporation during the last 16 hours in culture. In other experiments splenocytes from non-treated BALB/c mice were isolated and in vitro stimulated ($1\times10^6$ cells/ml) with LPS in the presence or absence of different sources of NMPF (37.5-600 IU/ml)(Pregnyl, Organon; APL, Wyeth Ayerst; Profasi, Serono), NMPF fractions (10-20 mg/ml), b-48 peptide or its breakdown products, anti-MIF or combinations of these products each at 10 mg/ml. After 24 hours of culture, the LPS stimulated proliferation of splenocytes was measured.

Results

NMPF purification: Samples of NMPF from different sources (Pregnyl, APL, Profasi, Pregnancy urine) were applied on the Macroshere GPC 300 Å column and eluted with ammonium bicarbonate. Three selected areas were fractionated, NMPF-1 which elutes apparently with molecular weight of >25 kDa, NMPF-2 which elutes apparently with molecular weight between the 25 kDa-6 kDa, and NMPF-3 which elutes apparently with molecular weight <6 kDa (FIG. 1.). All these fractions were lyophilized and were tested for anti-shock activity (shown elsewhere in this document). The lower molecular weight fraction (NMPF-3) which elutes after the column volume was further fractionated on the Macrosphere GPC 60 Å column (FIG. 2.). All fractions were lyophilized and were also tested for anti-shock activity.

NMPF treatment in LPS-induced septic shock: To determine the effect of high-dose LPS treatment in NMPF treated mice, BALB/c mice (n=6) were injected intraperitoneally with LPS (150 mg/kg) and survival was assessed daily for 5 days. PBS-treated BALB/c mice succumbed to shock from day 1 after high-dose LPS injection, with lower than 10% of mice alive on day 5 (FIG. 3.). In contrast, 100% of the mice treated with NMPF from source Pregnyl, or its fractions NMPF-1 or NMPF-3 obtained from GPC 300 Å column, were alive on day 5 ($P<0.001$) (FIG. 3.), while groups of mice treated with NMPF-2 from source Pregnyl or Dexamethasone (data not shown) demonstrated around 25% of survivors (FIG. 3). Not all commercial hCG preparations showed NMPF activity; for example NMPF from source Profasi showed only partial anti-shock activity (around 40% survival). In addition, variability in NMPF activity between different batches of the same source as well as variability of activity of same batch in time was observed. Treatment of BALB/c mice with APL before or after the shock induction, showed in a number of experiments acceleration of shock and early death.

In order to determine whether there are factor(s) present in hCG preparation that also accelerate shock and inhibit or counteract NMPF activity, we further fractionated NMPF-3 from a pretested active batch (containing anti-shock activity) and a non-active batch from source Pregnyl on GPC 60 Å column. Three selected areas were fractionated, NMPF-3.1 which elutes apparently with molecular weight of >2000 Da, NMPF-3.2 which elutes apparently with molecular weight between 2000-300 Da and NMPF-3.3 elutes apparently with molecular weight lower then 300 Da (FIG. 2.). All fractions were tested for anti-shock activity.

Results from these experiments revealed that anti-shock activity in a pretested active batch resided in a fraction NMPF-3.2, while NMPF-3.3 fraction from both (active and non-active) batches accelerated shock (FIG. 4.).

In order to determine whether NMPF-3.3 inhibits the anti-shock activity of NMPF-3.2, we added NMPF-3.3 into NMPF-3.2 in 10:1 ratio (100:10 mg) and injected the mixture i.p. in mice two hours after LPS injection (n=6). Data from these experiments showed that in all mice treated with NMPF-3.2 fraction alone, septic shock was inhibited and they had sickness scores lower than 2 (FIG. 4), while this anti-shock activity of NMPF-3.2 fraction was inhibited with NMPF-3.3. NMPF-3.3 treatment alone accelerated shock and the treated mice died even earlier than PBS treated mice (FIG. 4.). Same trend of results were obtained in experiments, in which active and non-active batches from Pregnyl were mixed and injected in BALB/c mice after septic shock induction (data not shown).

Ratio between NMPF-3.2 and NMPF-3.3: Next, we further purified NMPF-3.2 and NMPF-3.3 on GPC 60 Å column from active and non-active Pregnyl batches, and from first trimester pregnancy urine and determined the ratio. We found that first trimester pregnancy urine having anti-shock activity had around 1:2.2 ratio (NMPF-3.2 NMPF-3.3) (FIG. 5.) and non-active batch of Pregnyl had 1:3.4 ratio (FIG. 6.), while the active batch of Pregnyl had around 1:1 ratio (FIG. 7.).

Ex vivo LPS stimulated splenocytes proliferation: After 48 hours of LPS shock induction, splenocytes from PBS treated and NMPF treated mice (from mice treated with either active Pregnyl, thereof derived NMPF-3.2 or NMPF-3.3 fractions, or APL preparation) were isolated and restimulated with LPS. After 24 hours of culture, LPS stimulated proliferation of splenocytes was measured. Reduction in LPS induced proliferation was observed after culture of splenocytes from NMPF (active batch of Pregnyl) and thereof derived NMPF-3.2 (1600 vs 1350 cpm) fraction treated BALB/c mice as compared to PBS treated mice (3500 cpm), while treatment by NMPF(APL) or NMPF-3.3 increased the LPS stimulated proliferation (6000 vs 7200 cpm). Comparable results were obtained when splenocytes from untreated BALB/c mice were in vitro stimulated with LPS in the presence of above mentioned additions (data not shown).

In vitro treatment with NMPF from different sources, b-48 peptide, denaturated b-48 peptide and anti-MIF: The major characteristics of pre-eclampsia resemble that of septic shock. Therefore we hypothesized that there might be also NMPF (IR) factor(s)that are involved in pre-eclampsia and also worsen septic shock or sepsis. Above we have shown that NMPF-3.3 is one such fraction which accelerates septic shock and increases in vitro/ex vivo LPS induced splenocytes proliferation, which is correlated with increase in the disease seventy. In the urine of pre-eclamptic patients high levels of nicked hCG b-subunits are present. Therefore we also tested whether these nicked subunits worse septic shock and so resemble NMPF-3.3 traction. Furthermore, MIF is an important mediator of lethal endotoxemia and staphylococcal toxic shock, so we also compared the effects of b-48 peptide and NMPF on proliferation with anti-MIF and MIF.

These experiments revealed that anti-MIF has a trend to decrease LPS induced proliferation, similar as a pretested Pregnyl batch that shows anti-shock activity (NMPF-PG$^+$) (FIG. 8.). Moreover, anti-MIF and NMPF-PG$^+$ together work synergistically and decrease proliferation (FIG. 8.). NMPF from APL (NMPF-A), non-active Pregnyl batch (NMPF-PG$^-$; without anti-shock activity) and b-48 peptide (NMPF-K) increased the LPS induced proliferation as compared to LPS only (FIGS. 8-12). On the other hand, NMPF-PG+ or denaturated b-48 peptide (NMPF-Kb) inhibited and decreased the LPS induced proliferation at least till the level of anti-MIF treatment alone (FIGS. 8-12.). In vivo treatment of BALB/c mice with NMPF-PG$^-$, NMPF-K or NMPF-A after septic shock induction accelerated the disease severity (at t=48 hrs 0-25% survival rate) as compared to PBS treated mice (at t=72 hrs 15% survival rate), while septic shock in BALB/c mice was completely inhibited by NMPF-PG$^+$ or NMPF-Kb.

In addition, our NOD spleen cells transfer experiments revealed that 22 days after transferring, NOD.scid mice receiving b48-peptide and PBS treated spleen cells were positive for diabetes and within a week they reached a blood glucose level above 30 mmol/l, while NOD.scid mice receiving NMPF (pregnyl) treated spleen cells remained normal (blood glucose <8 mmol/l). 6 weeks after transferring, the PBS and b48 reconstituted NOD.scid mice looked very uncomfortable, while NMPF mice group remained healthy. Mice from all groups were killed at this time.

There are many physiological conditions and immune pathologies where adaptive and innate immune systems are involved separately or in combination. For example, it has been shown that in pregnancy the maternal innate immune system is more stimulated, and it has been proposed that type II diabetes mellitus is due to chronic hyperactivation of the innate immune system. Another example is the involvement of the innate immune system in listeriosis. Dysregulation in the adaptive immune system may also lead to immune diseases like systemic or organ-specific autoimmunity, allergy, asthma etc, and the adaptive immune system can also play a role in the maintenance of pregnancy and in the prevention of "allograft" rejection and chronic inflammation, presumably including atherosclerosis and related diseases.

As shown in our previous (Immunoregulator; WO99-59617) NMPF (IR) is able to regulate the Th1/Th2 balance in vivo (BALB/c, NOD) and in vitro. In dominant Th1 phenotype models like NOD, NMPF (like NMPF-PG and its fractions) amongst others promote the IL-10 and TGF-beta production, which indicates the induction of regulatory cells like Th3 and Tr1 by NMPF. These regulatory cells may play role in the beneficial effects of NMPF in immune and inflammatory diseases and immune tolerance. While NMPF and several of its fractions are able to inhibit the production of IFN-gamma in vitro and in vivo, this was not observed for NMPF-3 (IR-P3) and recombinant hCG (rhCG). NMPF-3 (IR-P3) and rhCG separately show no to moderate inhibition of the IFN-gamma production, but the combination of NMPF-3 and rhCG gives a strong inhibition of the IFN-gamma production. This implies the need of NMPF-3 for rhCG for at least its IFN-gamma inhibition capacity in these models, while NPMPF-1 and NMPF-2 alone are capable to inhibit IFN-gamma production. This holds also for the anti-CD3 stimulated spleen cells obtained from in vivo treated NOD mice and for the polarization of T-helper cells to the Th2 phenotype. In our previous work we have also shown that NMPF (IR) has the potential to inhibit acute inflammatory responses, like in sepsis or septic shock. So, chronic as well as acute immune responses are modulated by NMPF.

By way of example and not wishing to bound to theory, in pregnancy a fetus has to survive potential maternal immune rejection, which is in part achieved through deviation of the maternal immune system towards Th2-type immune responses. But in this way maternal immune suppression carries the attendant risk of infection, as is observed in transplant patients receiving corticosteroids or other immunosuppressive therapy. NMPF (IR) factor(s) obtainable at least from pregnancy urine and thereof derived hCG preparations have the potential to modulate immune responses in such a way that the maternal rejection of the fetus is suppressed and that the mother maintains or even increases her resistance to infection. These and related factors are also responsible for the inhibition of immune diseases, particularly Th1-mediated immune diseases, during pregnancy.

By way of example and not wishing to bound to theory, pregnancy apparently demands incompatible immune adjustments. On the one hand, adaptive immune responses during pregnancy are modulated at different cellular levels towards immune tolerance state (such as Th2-type) and on the other hand the maternal innate immune system is modulated for resistance to infection. The evidence is that components of the maternal innate immune system are systemically activated. There are increased numbers of monocytes and granulocytes from the first trimester onwards. It has also been found that in normal pregnancy circulating monocytes and granulocytes in the maternal blood have an activated phenotype, in some ways comparable with changes observed in systemic sepsis. Others have shown increased monocyte phagocytosis and respiratory burst activity, and an increased expression of endotoxin receptor CD14 on monocytes as well as an increased response to endotoxin: monocytes from normal women produce more of the proinflammatory cytokines like in septic shock. Many studies have similarly found granulocyte activation in pregnancy as well as changes in plasma levels of soluble innate factors typical of an acute phase response. Not all components of the innate system are activated in the maternal circulation. Most notably, cytotoxic activity and IFN-gamma production by NK cells are suppressed.

By way of example and not wishing to bound to theory, we propose that one of the mechanisms of NMPF to modulate the immune response during pregnancy is the following: some NMPF factors during pregnancy can ensure that if T cells are activated, there is a bias to a Th2 response. This could be achieved by effecting different cell populations like macrophages, DC, T cells and their regulatory subsets. Other or similar NMPF factors could activate monocytes and hence other innate cells. So, the balance between different NMPF factors is crucial for a balanced regulation of different immune responses. We propose that in pre-eclampsia there is a misbalance between different NMPF factors. Over-activation of innate cells by NMPF factor(s) and/or a decrease in adaptive immune response (particularly Th1-type) inhibiting NMPF factor(s) could cause Th1/Th2 misbalance towards the Th1 phenotype, in some ways comparable with changes observed in systemic sepsis. Our results showed that there are also NMPF factor(s) (NMPF-3.3) that can stimulate innate immunity and accelerate septic shock, while other NMPF factor(s) like NMPF-3.2 inhibit septic shock and the activity of NMPF-3.3. NMPF-3.2 factor(s) present in NMPF-3 fraction in combination with for example hCG modulate the adaptive immune response towards Th2-type (WO99-59617; inhibition of IFN-gamma by NMPF-3 (IR-P3) in combination with hCG) and is essential for normal pregnancy and inhibition of Th1 autoimmune diseases, induction of tolerance etc.

Analysis of hCG preparation (Pregnyl) and pregnancy urine have shown that hCG preparation and pregnancy urine having anti-shock activity contain NMPF-3.2 and NMPF-3.3 fractions in about an 1:2 ratio or higher, while hCG preparations without anti-shock activity or that worse septic shock have an NMPF-3.2 and NMPF-3.3 ratio of 1:3 or lower. This also explains why not all commercial hCG preparations have anti-shock activity. Moreover, we showed that hCG preparation possessing a high ratio of NMPF-3.3:NMPF-3.2 and so having no anti-shock activity, mixed with an active hCG preparation could gain anti-shock activity. So, the ratio between different NMPF factors or fractions like NMPF-3.2 and NMPF-3.3 can be used as a diagnostic marker not only for the prediction of successful pregnancy, but also for different immunopathology such as pre-eclampsia, sepsis or septic shock etc. In addition, in abnormal pregnancy like pre-eclampsia, one can also use NMPF factor(s) or NMPF-fraction(s) (e.g. NMPF-3.2) as a treatment. Our experiments also showed that NMPF (NMPF-3.2) inhibited septic shock even 30 h after shock induction, this shows that NMPF not only inhibits early mediators of endotoxin lethality like TNF-alpha, IL-1b, MIF, but also inhibits late mediators such as recently characterized high mobility group-1 (HMG-1) protein (Science 285, 248-251).

hCG is a member of the structural superfamily of cysteine knot growth factors like NGF, PDGF-B and TGF-beta and a members of the glycoprotein hormone family which also includes LH, FSH and TSH. They each consist of two non-covalently associated protein subunits, a common 15 kD alpha chain and a hormone specific 23 kD beta chain (Annu. Rev. Biochem. 50, 465-495). hCG is produced by placental trophoblasts of normal pregnancy, and in gestational trophoblastic disease. It is also produced in much smaller quantities by the pituitary (Endocrinology 137, 1402-1411) in both pre- and postmenopausal women and in men (Trends in Endocrinology and Metabolism 1, 418-421)., in many non-gestational malignant tumors and other tissues. hCG possesses a complex structure as a family of isoforms with structural, immunological and biological differences. The chemical basis for this heterogeneity is not known with certainty but differences in the amino acid composition, carbohydrate residues or both have been proposed. More recently it was also shown that oxidation of specific methionine residues may also be responsible. Different forms of hCG, alpha and beta-subunits, their nicked fragments, beta-core fragment and multiple isoforms of hCG have been reported in different tissues and body fluids (Journal of Endocrinology 161, 99-106; Endocrinology 129, 1541-1550; Obstet. Gynecol. 77, 53-59; Journal of Biochemistry 107, 858-862; Obstet. Gynecol. 80, 223-228; Endocrinology 133, 985-989; 129, 1551-1558; 130, 2052-2058; Journal of Endocrinology 135, 175-188; 139, 519-532; Molecular and Cellular Endocrinology 125, 93-131).

Since all commercial hCG preparations are derived from pregnancy urine and contain different breakdown products of hCG, we speculated whether these products have NMPF activity. The most known breakdown products of hCG are beta-core hCG, a peptide bond nick in the beta-subunit between residues 44-45, 46-47 and 47-48. b48 (NMPF-K) is found in approximately 10-20% of the molecules in pregnancy urine and is associated with a natural urinary metabolite of hCG. Our experiments showed that NMPF-K accelerates septic shock (like MIF) and LPS induced proliferation of splenocytes alone or in combination with a non-active hCG preparation. This effect is inhabitable with anti-MIF, active hCG preparation, NMPF-3.2 and denaturated b48 (NMPF-Kb) peptide. This shows that NMPF-K activity resembles with NMPF-3.3 and the NMPF-Kb activity resembles to NMPF-3.2. In addition, there are also other peptide bond cleavages in hCG and its subunits as well as heterogeneity of the beta-core fragment. For example b45 bond cleavage, mainly found in hCG preparation and in urine, possibly derive from the action of bacterial proteases. In addition, Medeiros et. al. showed that HPLC separation of beta-core in its reduced and S-carboxymethylated forms showed three peptides, but only two of them could be sequenced and was demonstrated to be the previously reported b6-40 and b55-92 peptides of bhCG, while the third peak did not give any clear sequence because of the low signal due to several unidentified amino acids. We showed that breakdown products of NMPF-K share activity with NMPF-3.2. This NMPF-K peptide lies between two beta-core fragments (b6-40 and b55-92) and partially derived from beta-core b55-92 fragment. It is possible that there are also other single and/or double cleavage products of beta-core fragments or of not yet identified beta-core peptides (like Medeiros et. al. showed beta-core faction with a unidentified amino acids) responsible for NMPF activity in hCG preparations and pregnancy urine. Breakdown products of b48-peptide with additional unidentified amino acids from beta-core and/or with additional glycosylation possess among other anti-diabetic and anti-chronic inflammatory activity.

In short, the invention provides among others an immunoregulator (immunoregulating peptide) obtainable or derivable from a urinary metabolite of hCG, in particular from (nicked) forms of beta-hCG, or (synthetic) peptide homologues or analogues thereof. These forms of beta-hCG have peptide bond cleavages within the beta-subunit (Birken et al, Endocrinology 133:1390-1397, 1993), and herein it is provided that the breakdown products, especially those from the beta-44 to beta-49 regions provide significant immunoregulatory effects by using the animal model test systems as provided.

It was found for example herein in animal experiments as described below that peptides obtainable from hCG react in a septic shock model with strong immunoregulatory effects.

EXAMPLE II

Materials and Methods

Gel permeation: We fractionated commercial hCG preparation (c-hCG, Pregnyl, Organon, Oss, The Netherlands) as follows: we used Shimadzu HPLC system equipped with Alltech macrosphere size exclusion (GPC) 60 Å column (4.6 mm ID×250 mm L) in 50 mM ammonium bicarbonate buffer. The separation range for this column was 28,000-250 Dalton. Sample (20,000 IU hCG/ml) load volume was 10-50 ml. The flow rate was 0.3 ml/min for 25 minutes. External molecular weight standards were also employed to calibrate the column elution positions. The markers used were: aprotinin (6,500 Da), cytochrome C (12,400) and carbonic anhydrase (29, 000). In addition, the concentrated urine (see urine purification) obtained from Pelicon system was filtered through 0.45 mm filter and 40,000 IU c-hCG (Pregnyl) dissolved in 50 mM ammonium bicarbonate were analysed on Shimadzu HPLC system equipped with Superdex G25 (30 mm ID×990 mm L) desalted column in 50 mM ammonium bicarbonate buffer supplemented with 5% methanol. The separation range for column were 5000-1000 Dalton. Sample load volume was 7-10 ml. The flow rate was 3 ml/min for 250 minutes. External molecular weight standards were also employed to calibrate the column elution positions. 100 ml fractions were collected, lyophilised and were further tested for anti-shock activity.

Urine purification: First trimester pregnancy urine (2 liters) was collected in a bottle from a healthy volunteer and was refrigerated until delivered at the laboratory within 2 days. Upon delivery, 1 gram per liter of sodium azide was added and the pH was adjusted to 7.2-7.4 with sodium hydroxide and allowed to sediment for 1-hour (h) at room temperature (RT). Approximately, 75% of the supernatant was decanted and the remainder close to the precipitate was centrifuged (10 min at 25000 rpm at 4° C.) to remove sediment and added to the rest of the supernatants. The supernatant (about 2 liter) was concentrated in a Pellicon ultrafiltration set-up equipped with a Pellicon XL filter (Millipore, cat. No. PXCO1OC50) with a 5 kDa cut-off. The final volume was 150 ml. Urine from healthy non-pregnant women, and from women in their first trimester pregnancy with autoimmune disease (SLE, Sjogren) were treated with same method as mentioned above.

Endotoxin shock model: For the endotoxin model, BALB/c mice were injected i.p. with 8-9 mg/kg LPS (E. coli 026:B6; Difco Lab., Detroit, Mich., USA). Control groups (PBS) were treated with PBS i.p. only. To test the effect of NMPF, we treated BALB/c with a dose of 300-700 IU of different hCG preparations (PG23;Pregnyl batch no. 235863, PG25; Pregnyl batch no. 255957), with peptides (5 mg/kg) or with different fractions (0.5-1 mg/kg) after two hours of LPS injection.

LPS induced proliferation: In order to determine whether treatment of LPS injected BALB/c mice with different fractions, peptides or commercial hCG (c-hCG) alter the proliferative response of spleen cells, we also isolated splenocytes from above mentioned LPS shock experiments. Total spleen cells ($1\times10^6$ cells/ml) from treated BALB/c mice were restimulated in RPMI$^+$ supplemented with 10% FBS with different concentrations of LPS (5, 10, 20 mcg/ml) in round bottom 96-well plates. Plates were incubated at 37° C. in 5% CO2 in air for 24 hrs. The proliferation was measured via [$^3$H]TdR incorporation by adding 0.5 mCi/well during the last 12 hrs in culture.

Flow cytometry: In some experiments, after 48 hours of septic shock induction spleen cells were isolated for flow cytometry analysis. The cell surface markers analysed in these experiments were CD19, CD80, CD40, B220, CD4, F4/80, NK1.1, DX-5 and CD25. For analysis of these marker FITC or PE conjugated mABs were purchased from BD PharMingen. Shortly, spleen cells ($2\times10^5$) were washed twice with FACS buffer and incubated with mABs according to the manufacturer's instructions. Hereafter, cells were washed and analysed on FACSort flow cytometer (Becton Dickinson). Based on their forward and side scatter characteristics, live cells were gated and analyzed.

Coronary Artery Occlusion (CAO) experiments: NMPF have immunoregulatory effects in chronic inflammatory as well as acute inflammatory mice models. Since certain cytokines like TGF-betal, TNF-alpha, IL-1 and ROS (reactive oxygen species) have been implicated in irreversible myocardial damage produced by prolonged episodes of coronary artery occlusion and reperfusion in vivo that leads to ischaemia and myocardial infarct, we tested the cardioprotective properties of peptides in ad libitum fed male Wistar rats (300 g). The experiments were performed in accordance with the Guiding principles in the Care and Use of Animals as approved by the Council of the Amcerican Physiological Society and under the regulations of the Animal Care Committee of the Erasmus University Rotterdam. Shortly, rats (n=3) were stabilized for 30 minutes followed by i.v. 1 ml of peptide treatment (0.5 mg/ml) in 10 minutes. Five minutes after completion of treatment, rats were subjected to a 60-min coronary artery occlusion (CAO). In the last 5 minutes of CAO, rats were again treated over 10 minutes i.v. with 1 ml of peptide (0.5 mg/ml) followed by 120 minutes of reperfusion (IP). Experimental and surgical procedures are described indetail in Cardiovascular Research 37(1998) 76-81. At the end of each experiment, the coronary artery was re-occluded and was perfused with 10 ml Trypan Blue (0.4%, Sigma Chemical Co.) to stain the normally perfused myocardium dark blue and delineate the nonstained area at risk (AR). The heart was then quickly excised and cut-into slices of 1 mm from apex to base. From each slice, the right ventricle was removed and the left ventricle was divided into the AR and the remaining left ventricle, using micro-surgical scissors. The AR was then incubated for 10 min in 37° C. Nitro-Blue-Tetrazolium (Sigma Chemical Co.; 1 mg per 1 ml Sorensen buffer, pH 7.4), which stains vital tissue purple but leaves infarcted tissue unstained. After the infarcted area (IA) was isolated from the noninfarcted area, the different areas of the LV were dried and weighed separately. Infarct size was expressed as percentage of the AR. Control rats were treated with PBS.

NOD experiments: We treated NOD mice at the age of 8-10 weeks with PBS (n=3) or peptide 1 (VLPALPQVVC (SEQ ID NO:3)), or 5 recombinant hCG (rhCG, Sigma) and rhCG in combination with peptide 1 each with 10-40 mcg i.p. for three days. In order to determine the effect of the treatment on Th1 polarisation, we isolated CD4+cells and performed Th1 polarisation assays as follows: Purified CD4+ T cells from the spleen were obtained by negative selection due to complement depletion with antibodies specific for B cells, NK cells, monocytes/macrophages and granulocytes. Cells were further purified using magnetic activated cell sorting with a cocktail of biotinylated mAbs against CD11b, B220, CD8 and CD40, followed by incubation with streptavidin-conjugated microbeads (Milteny Biotech, Bergisch Gladbach, Germany). CD4+ T-cells used for experiments were always 90-95% purified as determined by flow cytometry. For primary stimulation, purified CD4+ T cells were cultured at $1\times1^5$ cells/well in flat bottom 96-well plates (Nalge Nunc Int., Naperville, Ill., USA), and stimulated with plate-bound anti-CD3 mAb (145-2C11, 25 mg/ml), anti-CD28, and IL-2 (50 U/ml). For differentiation of Th1 cells, anti-IL-4 mAb (11B11; 10 mg/ml) and IL-12 (10 ng/ml) were added to the cultures. Unprimed cultures contained only anti-CD3, anti-CD28 and IL-2. All doses were optimised in preliminary experiments. After 4 days of culture, the cells were washed 3 times and transferred to new anti-CD3-coated 96-well plates and restimulated in the presence of IL-2 (50U/ml) and anti-CD28 (10 mcg/ml). Forty-eight hours later, supernatants were collected and assayed for IFN-gamma production by ELISA as readout for Th1 polarization.

Cytokine ELISA: IFN-gamma was detected using monoclonal anti-IFN-gamma antibody (XMG1.2) as the capture antibody and revealed with biotinylated-conjugated rat anti-mouse IFN-gamma monoclonal antibody (R46A2). ABTS substrate was used for detection.

Flat bottom microplates (96-wells, Falcon 3912, Microtest II Flexible Assay Plate, Becton Dickinson, Oxnard, USA) were coated with IFN-gamma specific capture antibodies (XMG1.2, 5 mg/ml) diluted in PBS and stored at 4° C. for 18 hrs. After coating, plates were washed (PBS, 0.1% BSA, 0.05% Tween-20) and blocked with PBS supplemented with 1% BSA at room temperature for 1 hr. After washing, samples and standards were added and incubation was continued for at least 4 hrs at room temperature. Thereafter, plates were washed and biotinylated detection antibodies were added (R46A2, 1 mcg/ml) and incubated overnight at 4° C. After washing, streptavidin-peroxidase (1/1500 diluted, Jackson Immunoresearch, West Grove, Pa., USA) was added. After 1 hr, plates were washed and the reaction was visualized using 2,2'-azino-bis-3-ethylbenz-thiazoline-6-sulfonic acid (ABTS, 1 mg/ml, Sigma, St. Louis, Mo., USA). Optical density was measured at 414 nm, using a Titertek Multiscan (Flow Labs, Redwood City, USA).

Peptide synthesis: The peptides were prepared by solid-phase synthesis (Merrifield, 1963) using the fluorenylmethoxycarbonyl (Fmoc)/tert-butyl-based methodology (Atherton, 1985) with 2-chlorotrityl chloride resin (Barlos, 1991) as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF) (ii) coupling of the Fmoc amino acid (3 eq) with diisopropylcarbodiimide (DIC)/1-hydroxybenzotriazole (HOBt) in DMF/N-methylformamide (NMP) (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H20/triisopropylsilane (TIS) 95:2.5:2.5. After 30 minutes TIS was added until decouloration. The solution was evaporated in vacuo and the peptide precipitated with diethylether. The crude peptides were dissolved in water (50-100 mg/ml) and purified by reverse-phase high-performance liquid chromatography (RP-HPLC). HPLC conditions were: column: Vydac TP2181OC18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For peptides LQG and LQGV (SEQ ID NO:8): 10 minutes 100% A followed by linear gradient 0-10% B in 50 minutes. For peptides VLPALP (SEQ ID NO:12) and VLPALPQ (SEQ ID NO:9): 5 minutes 5% B followed by linear gradient 1% B/minute. The collected fractions were concentrated to about 5 ml by rotation film evaporation under reduced pressure at 40' C. The remaining TFA was exchanged against acetate by eluation two times over a column with anion exchange resin (Merck II) in acetate form. The eluate was concentrated and lyophilized in 28 hours.

EAE models: Female SJL/J mice (n=4; 8-12 weeks of age; obtained from Harlan, Zeist, The Netherlands, or bred at the Erasmus University Rotterdam) were immunized with 100 mcg of proteolipid protein peptide 139-151 (PLP139-151; H-His-Ser-Leu-Gly-Lys-Trp-Leu-Gly-His-Pro-Asp-Lys-Phe (SEQ ID NO:14); obtained from either Peptides International, Louisville, Ky., or TNO Prevention and Health, Leiden, The Netherlands), emulsified in CFA containing 4 mg/ml of Mycobacterium tuberculosis H37 Ra (Difco, St. Louis, Mo.). distinct model of EAE were induced by injection of either 200 mg pertussis toxin (Sigma) in 50 mcl PBS i.v. on day 0 and 2 post immunization, or 1010 Bordetella pertussis bacteria (RIVM, Bilthoven, The Netherlands) in 200 mcl PBS i.v. on day 1 and 3 after immunization. Mice were examined for clinical signs of EAE and weighed daily.

clinical symptoms of EAE were scored on scale of 0 to 5 with graduations of 0.5 for intermediate scores: (0) no clinical signs; (1) flaccid tail; (2) mild paraparesis; (3) dual hind limb paralysis; (4) moribund; or (5) death due to EAE. Starting from day 7 post immunization, 60-F2 or 60-F3 fractions (20 mcg) from c-hCG (10,000 IU) in a total volume of 200 mcl PBS was injected i.p. for two weeks at alternate day. Control mice were treated with PBS only.

Results

Gel permeation of urine and commercial hCG preparation: c-hCG (FIG. 16) and first trimester pregnancy urine were fractionated on HPLC system equipped with GPC 60A column. Three selected areas were fractionated, 60A-fraction 1 (60A-F1) which elutes apparently with molecular weight of >10 kDa, 60A-F2 which elutes apparently with molecular weight between the 10 kDa-1 kDa, and 60A-F3 which elutes apparently with molecular weight <1 kDa. These fractions were tested further for anti-shock activity.

In addition, urine from healthy pregnant women in their first trimester pregnancy, urine from women in their first trimester pregnancy with autoimmune disease and urine from healthy non-pregnant women were analysed on superdex G25 column. All 100 ml fractions were also tested for anti-shock activity. FIGS. 17 and 18 show the chromatograms of c-hCG and urine from healthy pregnant women in their first trimester of pregnancy.

Survival curve: To determine the effect of high-dose LPS treatment in c-hCG and urine fractions treated mice, BALB/c mice (n=6) were injected intraperitoneally with LPS (8-9 mg/kg) and survival was assessed daily for 5 days. In our previous patent (WO9959617) and in this patent application we have shown that three selected areas were fractionated on GPC 60A column: 60A-F1 which elutes apparently with molecular weight of >10 kDa, 60A-F2 which elutes apparently with molecular weight between the 10 kDa-1 kDa, and 60A-F3 which elutes apparently with molecular weight <1 kDa. All these activities were tested for anti-shock activity and they all had anti-shock activity (presumably the lower molecular weight activity also elutes along with the high molecular weight fractions). PBS-treated BALB/c mice succumbed to shock between days 1 and 2 after the high dose LPS injection, with less than 10% of the mice alive on day 5. In contrast 100% of 60A-F1 and 60A-F3 treated mice were alive on day 5 ($p<0.001$), while 60A-F2 treated mice demonstrated only around 70% of survival. Since the lower molecular weight fraction had also anti-shock activity, we fractionated c-hCG, urine of first trimester pregnancy, urine from women with autoimmune diseases in their first trimester of pregnancy and urine from healthy non-pregnant women on G25 superdex column. All 100 ml fractions were tested for anti-shock activity.

PBS-treated BALB/c mice succumbed to shock between days 1 and 2 after the high-dose LPS injection, with less than 10% of mice alive on day 5. In contrast, 100% of the mice treated with c-hCG, first trimester pregnancy urine fraction V from healthy individuals or urine from individuals with autoimmune disease in their first trimester of pregnancy were alive on day 5 ($P<0.001$). However, some fractions which were eluted before (fraction II and IV) and after (the anti-shock) fraction V (e.g. fraction VI) had accelerated shock and all treated mice died even much earlier (within 24 hours after septic shock induction) than PBS treated mice. In addition, the anti-shock activity of fraction III and V was inhibited by the addition of fraction II, IV or VI in at least ratio of 1:6. This applied also for fractions obtained from commercial hCG preparations and pregnancy urine from healthy individuals. Moreover, we have noticed that very less amount of anti-shock fractions from the urine of pregnant individuals with autoimmune, disease were need to inhibit septic shock in BALB/c mice. These women also showed clinical improvement in the autoimmune disease during pregnancy.

Illness kinetics: Visible signs of sickness were apparent in all of the experimental animals, but the kinetics and obviously the severity of this sickness were significantly different. After treatment of BALB/c mice with LPS (endotoxin) and either first trimester pregnancy urine fraction V from healthy individuals, first trimester pregnancy urine from individuals with autoimmune disease or commercial hCG preparation the clinical symptoms of the LPS treated BALB/c mice did not exceed the sickness level 2. In addition, these fractions even inhibited the symptoms of shock and mortality when administered 32 hours after LPS injection.

Peptides data (NMPF): The table below shows survival percentages of mice over the time period of 72 hours. For the LPS (endotoxin) model, BALB/c mice were injected i.p. with 8-9 mg/kg LPS (E. coli 026:B6; Difco Lab., Detroit, Mich., USA). Control groups (PBS) were treated with PBS i.p. only. We treated BALE/c mice with a dose of 300-700 IU of different hCG preparations (PG23; Pregnyl batch no. 235863, PG25; Pregnyl batch no. 255957) or with peptides (5 mg/kg) after two hours of LPS injection.

These experiments showed (table 1.) that peptides 4 and 6 inhibited shock completely (all mice had in first 24 hours sickness scores not higher than 2; shortly thereafter they recovered completely and had sickness scores of 0), while peptides 2, 3 and 7 accelerated shock (all mice had in first 24 hours sickness scores of 5 and most of them died, while the controle mice treated with LPS+PBS had sickness scores of 3-4 in first 24 hours and they died after 48 hours with sickness scores of 5). In addition, peptides 1, 5, 8, 9, 11, 12, 13 and 14 showed in number of different experiments variability in effectiveness as well as in the kind (inhibitory vs accelerating) of activity. This variability is likely attributable to the rate of breakdown of the various peptides, and the different effects the various peptides and their breakdown products have in vivo. Similar to the above mentioned shock experiments with fractions, the shock inhibiting activity was inhibitable by the addition of shock accelerating activity and visa versa.

These data are representative of at least 10 separate experiments.

TABLE 1

| Test substance | SEQUENCE | SURVIVAL IN TIME (HRS) 0 | 16 | 40 | 72 |
|---|---|---|---|---|---|
| PBS | | 100 | 100 | 67 | 17 |
| PG23 | | 100 | 100 | 100 | 100 |
| PG25 | | 100 | 83 | 83 | 83 |
| PEPTIDE NO. | | | | | |
| 1 | VLPALPQVVC (SEQ ID NO: 3) | 100 | 100 | 50 | 17 |
| 2 | LQGVLPALPQ (SEQ ID NO: 4) | 100 | 67 | 0 | 0 |
| 3 | LQG | 100 | 83 | 20 | 17 |
| 4 | LQGV (SEQ ID NO: 8) | 100 | 100 | 100 | 100 |
| 5 | GVLPALPQ (SEQ ID NO: 10) | 100 | 100 | 80 | 17 |
| 6 | VLPALP (SEQ ID NO: 12) | 100 | 100 | 100 | 100 |
| 7 | VLPALPQ (SEQ ID NO: 9) | 100 | 83 | 0 | 0 |

TABLE 1-continued

| | SEQUENCE | SURVIVAL IN TIME (HRS) 0 | 16 | 40 | 72 |
|---|---|---|---|---|---|
| 8 | GVLPALP (SEQ ID NO: 11) | 100 | 100 | 83 | 67 |
| 9 | VVC | 100 | 100 | 50 | 50 |
| 11 | MTRV (SEQ ID NO: 5) | 100 | 100 | 67 | 50 |
| 12 | MTR | 100 | 100 | 67 | 50 |
| 13 | LQGVLPALPQVVC (SEQ ID NO: 2) | 100 | 100 | 100 | 100 |
| 14 | (CYCLIC) LQGVLPALPQVVC (SEQ ID NO: 1) | 100 | 83 | 83 | 83 |

TABLE 2

| SEQUENCE ID: | | anti-shock effect |
|---|---|---|
| LQGV | (SEQ ID NO: 8) | +++ |
| AQGV | (SEQ ID NO: 15) | +++ |
| LQGA | (SEQ ID NO: 16) | +++ |
| VLPALP | (SEQ ID NO: 12) | +++ |
| ALPALP | (SEQ ID NO: 17) | ++ |
| VAPALP | (SEQ ID NO: 18) | ++ |
| ALPALPQ | (SEQ ID NO: 19) | ++ |
| VLPAAPQ | (SEQ ID NO: 20) | ++ |
| VLPALAQ | (SEQ ID NO: 21) | +++ |
| | | shock accelerating effect |
| LAGV | (SEQ ID NO: 22) | +++ |
| LQAV | (SEQ ID NO: 23) | +++ |
| VLAALP | (SEQ ID NO: 24) | +++ |
| VLPAAP | (SEQ ID NO: 25) | +++ |
| VLPALA | (SEQ ID NO: 26) | +++ |
| VLPALPQ | (SEQ ID NO: 27) | +++ |
| VLAALPQ | (SEQ ID NO: 28) | +++ |
| VLPALPA | (SEQ ID NO: 29) | +++ |

In table 2 we see the effect of ALA-replacement (PEPSCAN) in peptide LQGV (SEQ ID NO:8), VLPALP (SEQ ID NO:12), VLPALPQ (SEQ ID NO:9) in septic shock experiments. We conclude, that the change in even one amino acid by a neutral amino acid can lead to different activity. So, genomic differences as well as polymorphism in these peptides can regulate the immune response very precise. Derivates of these peptides, for example (but not limited to) by addition of non-classical amino acids or derivatives that are differentially modified during or after synthesis, for example benzylation, amidation, glycosylation, proteolytic cleavage, linkage to an antibody molecule or other cellular ligand etc. could also lead to a better effectiveness of the activity.

Since MIF is one of the major inducers of sepsis, we also restimulated spleen cells from Peptide 1 group mice with LPS in vitro and then measured the MIF production. FIG. 19 shows that in vivo treatment with LPS increased MIF production as compared to PBS treated mice, while Peptide 1 treatment after the shock induction inhibited MIF production (FIG. 19). No effect on MIF production was found in mice treated with Peptide 1 alone; this shows the specificity of the peptide 1. In addition, LPS restimulated proliferation was also studied in splenocytes from peptide 1 and c-hCG-V (fraction V from c-hCG) treated mice. These data showed that after restimulation with LPS in vitro, splenocytes from LPS treated mice have a greater capacity to proliferate in vitro as compared to PBS treated mice (FIG. 20). On the other hand, splenocytes from LPS+peptide 1 and LPS+c-hCG-V treated mice showed a much higher capacity to proliferate as compared to the LPS treated control mice (FIG. 20). No differences in LPS induced proliferation was observed in mice treated with PBS, peptide 1 or c-hCG-V alone.

FIG. 21 shows the effect of restimulation of splenocytes from in vivo treated mice with different doses of LPS in vitro. These data are also consistent with the above mentioned proliferation data. In these experiments restimulation of splenocytes from mice treated with peptide 1 (anti-shock activity), c-hCG (containing anti-shock activity) and c-hCG-V (anti-shock fraction from c-hCG) after the septic shock induction showed higher capacity to proliferate as compared to LPS+PBS treated mice. On the other hand, splenocytes from mice treated with peptide 2 (shock accelerating peptide) showed the same capacity to proliferate as compared to LPS+PBS treated mice (FIG. 21). In this figure it is important to notice that the kinetics of the proliferation of spleen cells from peptide 1 and c-hCG-V fraction treated mice were the same.

All together, in vitro stimulation of splenocytes from BALB/c mice treated with LPS and peptide or fraction with anti-septic shock activity decreased proliferation which is associated with inhibition of septic shock in vivo with these peptides or fractions. On the other hand, in vitro restimulation with LPS of splenocytes from in vivo LPS+anti-septic shock activity treated BALB/c mice increased proliferation which is associated with the inhibition of septic shock.

Flow cytometry: flow cytometry analysis of splenocytes from treated BALB/c mice revealed that the septic shock inhibitory and septic shock accelerating effects correlated with a characteristic pattern of surface makers of the spleen cells. FIG. 22 shows that the shock inhibitory activities (c-hCG, peptide 1, peptide 4 and peptide 6) increased the expression of CD80 molecule on CD19 cells as compared to PBS+LPS control group, whereas minor effect was observed with peptide 7 which accelerates shock. FIG. 23 shows decreased number of CD19/CD40 cells in the spleens of shock inhibitory activities as compared to PBS+LPS group, while no effect was observed with peptide 7 in shock experiments. FIGS. 24 and 25 shows septic shock inhibitory activity deactivates B220 positive and F4/80 positive cells as compared to the PBS+LPS treated groups. While the number of activated CD4+ T cells (FIG. 26) were increased with septic shock inhibitory activities. No differences were observed in the activation of B220-, F4/80- and CD4 positive cells with shock accelerating activity (peptide 7) (FIGS. 24-26). In addition, decrease in Nk1.1 cell membrane marker experssion was observed after treatment with LPS and peptide with septic shock inhibitory activities as compared to PBS+LPS group, while no effect was found after treatment with shock accelerating activity (FIG. 27) An increased number of Dx-5 (pan-NK cells marker) was observed with septic shock inhibitory as well as shock accelerating activity (FIG. 28). These results suggest that the septic shock inhibitory activity might be correlated with the deactivation of macrophages and B-cells, increased number activated CD4+ T cells and Dx-5 NK cells, while the septic shock accelerating activity correlates with increased number of activated Dx-5 NK cells (activation and number of macrophages, B and T cells compare to LPS+PBS).

hCG bioactivity: hCG binds to a LH receptor and induce signalling through cAMP. We determined whether peptides 1, 2, 4, 6 and low molecular weight anti-shock fraction c-hCG-V could bind to LH receptor and posses hCG bioactivity. FIG. 29 shows that hCG and c-hCG bind to 293-hLHRwt/CREluc cells and induce dose-dependent luciferase activity, while no effect was observed in luciferase activity with peptide 1, 2, 4, 6 and low molecular weight fraction c-hCG-V (FIG. 30). Moreover, addition of peptide 1, 2, 4, 6 and fraction c-hCG-V in the presence of hCG also did not show effect on luciferase activity induce by hCG itself (FIG. 31).

These data show that these peptides and fraction c-hCG-V do not have hCG bioactivity and they do not bind to LH receptor, nor that they disturb the binding of hCG to the LH receptor.

NOD experiments: In our previous patent (WO9959617) we have shown that high levels of IFN-gamma and dominant Th1 cells are associated with autoimmune diseases, we tested whether lower molecular weight fractions from a GOA column (60A-F3) of c-hCG and first trimester pregnancy urine can suppress dominant Th1 activity. To determine whether 60A-F3 needed an additional factor, such as hCG, to exert its full activity, we also treated NOD mice with 60A-F3, rhCG, and 60A-F3 in combination with rhCG and then evaluated the Th1 polarisation. FIG. 32 shows that there was moderate inhibition of IFN-gamma production found under Th1 polarisation conditions with 60A-F3 (c-hCG) and rhCG alone, while the outgrowth of Th1 cells was completely blocked with the combination of rhCG and GOA-F3 (c-hCG) (FIG. 32). Similar results were found with the lower molecular weight fraction 60A-F3 of first trimester pregnancy urine (data not shown).

We also stimulated spleen cells from these treated mice with anti-CD3 in vitro and then measured the IFN-gamma production at different time points. FIG. 33 shows that in vivo treatment with c-hCG and its fractions 60A-F1 (IR-P1) and 60A-F2 (IR-P2) inhibited the anti-CD3 stimulated IFN-gamma production, while a moderate increase in IFN-gamma production was found with rhCG and 60A-F3. In addition, fraction 60A-F3 (IR-P3) in combination with rhCG was able to inhibit the production of IFN-gamma (FIG. 33).

Anti-CD3 stimulated proliferation studies showed that anti-CD3 stimulated splenocytes from NOD mice treated with c-hCG, and 60A-P1 have a smaller capacity to proliferate in vitro (FIG. 34). Furthermore, splenocytes from 60A-F3 (IR-P3) and rhCG treated mice showed a higher capacity to proliferate as compared to the PBS treated control mice (CTL), while 60A-F3(IR-P3) in combination with rhCG caused the same decrease in proliferation as c-hCG and 60A-F1 (IR-P1) (FIG. 34). Moderate effect was found in the anti-CD3 stimulated proliferation of splenocytes from 60A-F2 treated NOD mice. Similarly, we also tested the effect of peptide 1 in combination with rhCG on Th1 differention and IFN-gamma production and proliferation. We observed that there was an increase of IFN-gamma production found under Th1 polarisation conditions with peptide 1 (27 ng/ml) and r-hCG alone (25 ng/ml) as compared to PBS (20 ng/ml),while the outgrowth of Th1 cells was completely blocked with the combination of rhCG and peptide 1 (7 ng/ml). Furthermore, splenocytes from peptide 1 and rhCG treated mice showed a higher capacity to proliferate as compared to the PBS treated control mice (CTL), while peptide 1 in combination with rhCG caused the same decrease in proliferation as c-hCG and 60A-F1 and 60A-F2.

EAE model: FIG. 35 shows the effect of 60A-F1 (IR-P1), 60A-F2 (IR-P2) and 60A-F3 (IR-P3) in EAE model induced by PLP+PTX. Here, we see that the treatment of mice with 60A-F1 and 60A-F2 reduced the disease severity as well as delayed the induction of EAE. While 60A-F3 treatment only delayed the onset of the disease, suggesting that it needs an additional factor(s) from 60A-F2. These result are also consistent with weight results shown in FIG. 35. In this figure, mice treated with active NMPF fractions after EAE induction, lost less weight than PBS treated mice. In addition, treatment of mice with c-hCG and 60A-F3 fraction from c-hCG showed less disease severity in EAE mouse model induced by PLP/B. pertussis which is a chronic disease model for EAE (MS) (FIG. 36).

CAO model: Our CAO data showed that 15 rats in control group treated with only PBS had infarcted area of 70±2% (average±standard error) after 60-minutes of CAO followed by 2 hours of reperfusion. While rats treated with peptide VLPALP (SEQ ID NO:12), LQGV (SEQ ID NO:8), VLPALPQVVC (SEQ ID NO:3), LQGVLPALPQ (SEQ ID NO:4), LAGV (SEQ ID NO:22), LQAV (SEQ ID NO:23) and MTRV (SEQ ID NO:5) showed infarcted area of 62±6%, 55±6%, 55±5%, 67±2%, 51±4%, 62±6% and 68±2%, respectively. Here, we see that certain peptides (such as VLPALP (SEQ ID NO:12), LQGV (SEQ ID NO:30), VLPALPQVVC (SEQ ID NO:3), LAGV (SEQ ID NO:22)) have protective on the area at risk for infarction. In addition, peptide LQAV (SEQ ID NO:23) showed smaller infarcted area but in some instances the area was haemorhagic infarcted. These are the same peptides that have anti-septic shock activity in vivo. It is important to note that mice treated with certain above mentioned peptides showed less viscousity of blood. Apart from immunological effect, there is a possibility that these peptides have also effect on blood coagulation system directly or indirectly and there a certain homology between CAO and sepsis models. So, in both model the circulatory system plays an important role in the pathogensis of the disease.

Discussion

Human chronic gonadotropin (hCG) is the glycoprotein hormone known as the hormone of pregnancy since its detection forms the basis of all pregnancy tests. It is produced very early in pregnancy by the developing trophoblast tissue which becomes the placenta. The hormone serves to maintain the steroid secretions of the corpus luteum (derived from the ovarian follicle after ovulation). The resultant steroids maintain the lining of the uterus in a state suitable for development of the embryo after its implantation.

HCG is a member of the glycoprotein hormone family, which also includes human luteinizing hormone (LH), human follicle-stimulating hormone (FSH), and human thyroid-stimulating hormone (TSH). These hormones are heterodimeric, sharing a common alpha subunit which in humans is encoded by a single gene and each having a unique beta subunit structure that confers hormone specificity. Among the four related hormones, only hCG and its close structural homolog, LH, bind to the same receptor present within the ovary in females and the testis in males. Human LH stimulates sex steroid production in both male and female and thus, the development of sex-specific characteristics. Human FSH binds to the different receptors in ovary and testis and serves to stimulate development of ova in the female and sperm in the male. The fourth homrone, human TSH, is not directly related to reproductive function but is responsible for stimulation of the production of thyroxine which controls the rate of bodily metabolism. Recently, after solving the three-dimensional (3D) structure of hCG, it has been shown that hCG is a member of the structural superfamily of cystine knot growth factors like NGF, PDGF-B and TGF-beta.

HCG exhibits a variety of forms, especially in urine (Birken, 1996; O'Connor, 1994; Alfthan, 1996; Cole, 1996; Wide, 1994; Birken, 1993; Cole, 1993). It appears in abundance in the urine of women during the first trimester of pregnancy. It exhibits charge heterogeneity due to variability in its sialic acid content. These forms include heterodimeric hCG with intact polypeptide backbone (hCG), heterodimeric hCG with peptide bond cleavages it its beta-loop 2 (residues 44-49) (nicked hCG), hCG beta-core fragment which is derived from hCG beta-subunit and is composed of residues 6-40 disulfide bridged to residues 55-92 and containing trimmed carbohydrate groups with no sialic acid, hCG beta-subunit derived from dissociation of hCG (beta-hCG), hCG alpha-subunit derived from dissociation of hCG (alpha-hCG). In addition, there is a pituitary form of hCG and pituitary form of an hLH beta-core fragment.

The beta-subunit, like the alpha-subunit of hCG, is composed of three loops; roughtly loop 1 (residues 9-40), loop 2 (residues 41-54) and loop 3 (residues 55-92). The beta-subunit also has the region termed "seatbelt", which wraps the alpha-subunit. The beta-subunit contains six disulfide bridges which hold the molecule together when peptide bond cleavages take place in loop 2 resulting in nicked hCG. The beta-core fragment is missing most of loop 2 and the seatbelt region. Hence, beta-core fragment is missing the entire seatbelt region, most of loop 2, and part of the amino terminus of the beta-subunit. Cleavages in the beta-loop 2 region (since is known to be exposed to solvent and is easily cleaved by proteases) result in biologically inactive hCG and many immunoassays fail to measure nicked hCG accurately due to diminished immunopotency after cleavages in beta-loop 2.

Here we have shown that number of selected breakdown products from loop 2 have immune regulatory effects. In our experiments peptides 4 (LQGV (SEQ ID NO:8)) and 6 (VLPALP (SEQ ID NO:12)) inhibited shock completely, while peptide 2 (LQGVLPALPQ (SEQ ID NO:4)), 3 (LQG) and 7 (VLPALPQ (SEQ ID NO:9)) accelerated shock. In addition, 1 (VLPALPQVVC (SEQ ID NO:3)), 5 (GVLPALPQ (SEQ ID NO:10)), 8 (GVLPALP (SEQ ID NO:11)), 9 (VVC), 11 (MTRV (SEQ ID NO:5)), 12 (MTR), 13 (LQGVLPALPQVVC (SEQ ID NO:2)) and 14 (cyclic, LQGVPALPQVVC (SEQ ID NO:2)) showed in number of different experiments variability in effectiveness as well as in the kind (inhibitory vs accelerating) of activity. This variability is likely attributable to the rate of breakdown of the various peptides, and the different effects the various peptides have. Nicking in amino acid residues of beta-hCG beginning at residues 44, 45, 48 and 49 by human leukocyte elastase are observed and the existence of nicked hCG (and also analogous nicking residues) had been established by several investigators (Kardana, 1991; Birken,-1991). Moreover, one or two nicked beta site are also commonly seen in a single hCG preparation as well as in LH preparations (Ward, 1986; Hartree, 1985; Sakakibara, 1990; Birken, 2000; Cole, 1991; Birken, 1993). Existence of these peptides or their homologous during pregnancy explains the inimunoregulatory state of the pregnancy. We have also shown that combination of peptide 1 with recombinant hCG is able to inhibit the development of dominant Th1 CD4+T cells while alone peptide 1 as well as recombinant hCG are not. This strongly suggests the need of additional factor from hCG in order achieved this effect. These other factors could be derived from different parts hCG or their homologous that are known to exist as fragments such as residues beta-CG6-40, beta-CG41-55, beta-CG55-92 and beta-CG90-110. In addition, anti-septic shock peptides as well as shock accelerating peptides have some, homology (>30%) with certain regions of the above mentioned fragments. Previously, we have shown that 60A-F2 (also known as IR-P2 with anti-diabetic activity) does not posses anti-shock effects and even in some case it accelerates septic shock. So, it is likely that indeed the peptides (table 1.) used in the septic shock model in combination with above mentioned fragments from beta-hCG have anti-chronic inflammatory (anti-diabetic) effects. Same is true for anti-EAE activity. These various peptides act inconsert to maintain hemostasis in the immune system and to prevent and control disbalances of the immune system like in infections, sepsis, autoimmune disease and in immune-mediated diseases.

We have shown in our previous patent (WO9959617) and this patent application that these NMPF activities have regulatory effects on innate and adoptive immune responses and are present in variable ratio's which explains the heterogeneity in results with commercial hCG preparations derived from pregnancy urine even from the single commercial manufacturer.

Number of studies have shown that hCG is not only produce by placenta, but for example pituitary as well as PBMC from non-pregnant individuals and male individuals are also able to produce hCG. Apart from the possibility that NMPF could be produce by placenta and by maternal cells, it is possible that NMPF could also be derived from hCG like molecules in the presence of various proteases and its regulation might be also tightly controlled by these proteases. Many proteases are shown to be exist in human plancenta, serum and in other parts of the body and one of their physiological roles could be the production of such immunomodulating peptides. Since we have also observed in our experiments the upregulation of pan-Nk cells (upregulation of Dx-5 marker), it is reasonable to think that that these type of cells do not have only natural killer cell activity, but are also involved in the regulation of adoptive as well as innate immune responses (Saito, 2000). For instance, Nk cells have the ability to modulate cellular response of antigen presenting cells (APC) like mcrophages, DC, and other lymphocytes population. In addition the strong cytotoxic activity of NK cells especially pan-NK cells contribute to the inhibition of tumor and tumor metastasis without inducing significant toxicity (Arai, 2000). Such immunomodulatory effect is also observed by neutrophils which are involved in different pathological insults such as sepsis. Not only are these cells crucial cell population which bridge innate resistance and acquired cell-mediated immune responses but they also play a role in driving T-cell host responses directly or indirectly through APC against the intracellular organism (Tateda, 2001). So, during pregnancy the cross talk mediated by NMPF and hCG in the maternal endocrine system, decidual immune system and trophoblast function modulate the relationship between maternal and fetal immunity and endocrine systems. On one side due to NMPF and hCG mammalian fetus perceived, as a successful allograft and successful parasite and on the other the maternal and the fetus are also optimally immuno-compitent for protection against threats like infections.

In addition, in this patent implication, we have shown that certain peptides (such as VLPALP (SEQ ID NO:12), LQGV (SEQ ID NO:30), VLPALPQVVC (SEQ ID NO:3), LAGV (SEQ ID NO:22)) have protective on the area at risk for infarction. In addition, peptide LQAV (SEQ ID NO:22) showed smaller infarcted area but in some instances the area was haemorhagic infarcted. These are the same peptides that have anti-septic shock activity in vivo. It is important to note that mice treated with certain above mentioned peptides showed less viscousity of blood. Apart from immunological effect, there is a possibility that these peptides have also effect on blood coagulation system directly or indirectly and there a certain homology between CAO and sepsis models. So, in both model the circulatory system plays an important role in the pathogensis of the disease. In this CAO model we see a protective role of NMPF on myocardial infarction this also suggest the same protective effect of NMPF in other organs as well in circulatory related disease. Examples of such diseases are (but not limited to) cerebral vascular incident (CVI), circulatory diseases of the brain, retinopathies (such as associated with vascular diseases like diabetes), circulatory diseases of pregnancy, thrombosis, atherosclerosis.

Since NMPF has a immunomodulatory effect and protective effect on CAO induced infarct, it can also be used in instances where there is risk of low blood circulation leading to decrease in oxygen supply (hypoxia). Examples are (but not limited to) angiography procedures, PTCA, (coronary) bypass procedures and stenosis.

BRIEF DESCRIPTION OF THE DRAWINGS

FIG. 36 shows the effect of treatment of mice with c-hCG and 60A-F3 fraction from c-hCG in EAE mouse model induced by PLP/B. pertussis which is a chronic disease model for EAE (MS).

SEQUENCE LISTING

Figure 1:
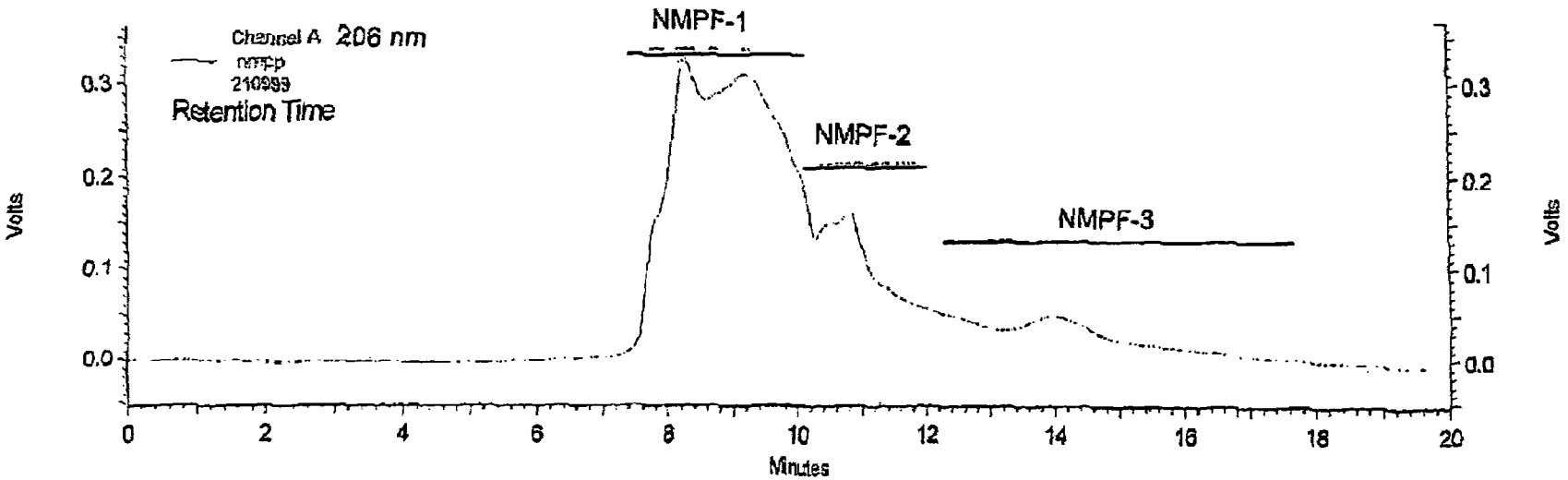
FIG. 1: This figure shows macrosphere GPC 300 Achromatogram of NMPF (Pregnyl) sample. Three selected areas were fractionated, NMPF-1 which elutes apparently with molecular weight of >25 kDa, NMPF-2 which elutes apparently with molecular weight between the 25 kDa-6 kDa, and NMPF-3 which elutes apparently with molecular weight <6 kDa.
Figure 2:
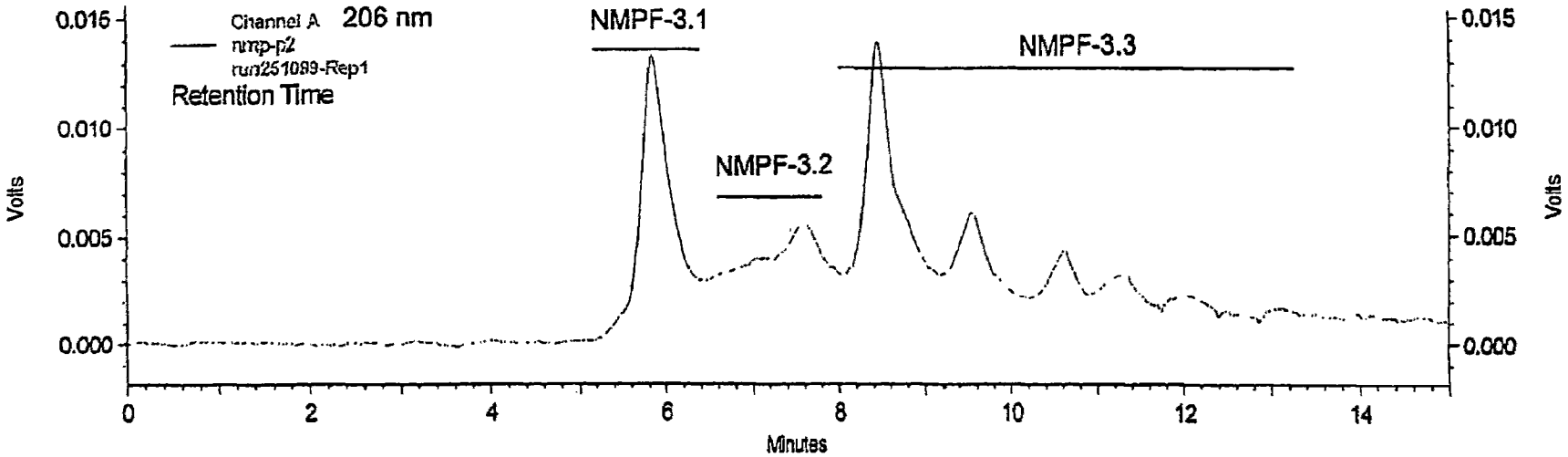
FIG. 2: This figure shows macrosphere GPC 60A chromatogram of NMP-3 fraction obtained from macrosphere GPC 300 A column. Three selected areas were fractioned, NMPF 1 which elutes apparently with molecular weight between 2000-300 Da and NMPF 3.8 elutes apparently with molecular weight lower than 300 Da (FIG. 2.). All fractions were tested for anti-shock activity.
Figure 3:
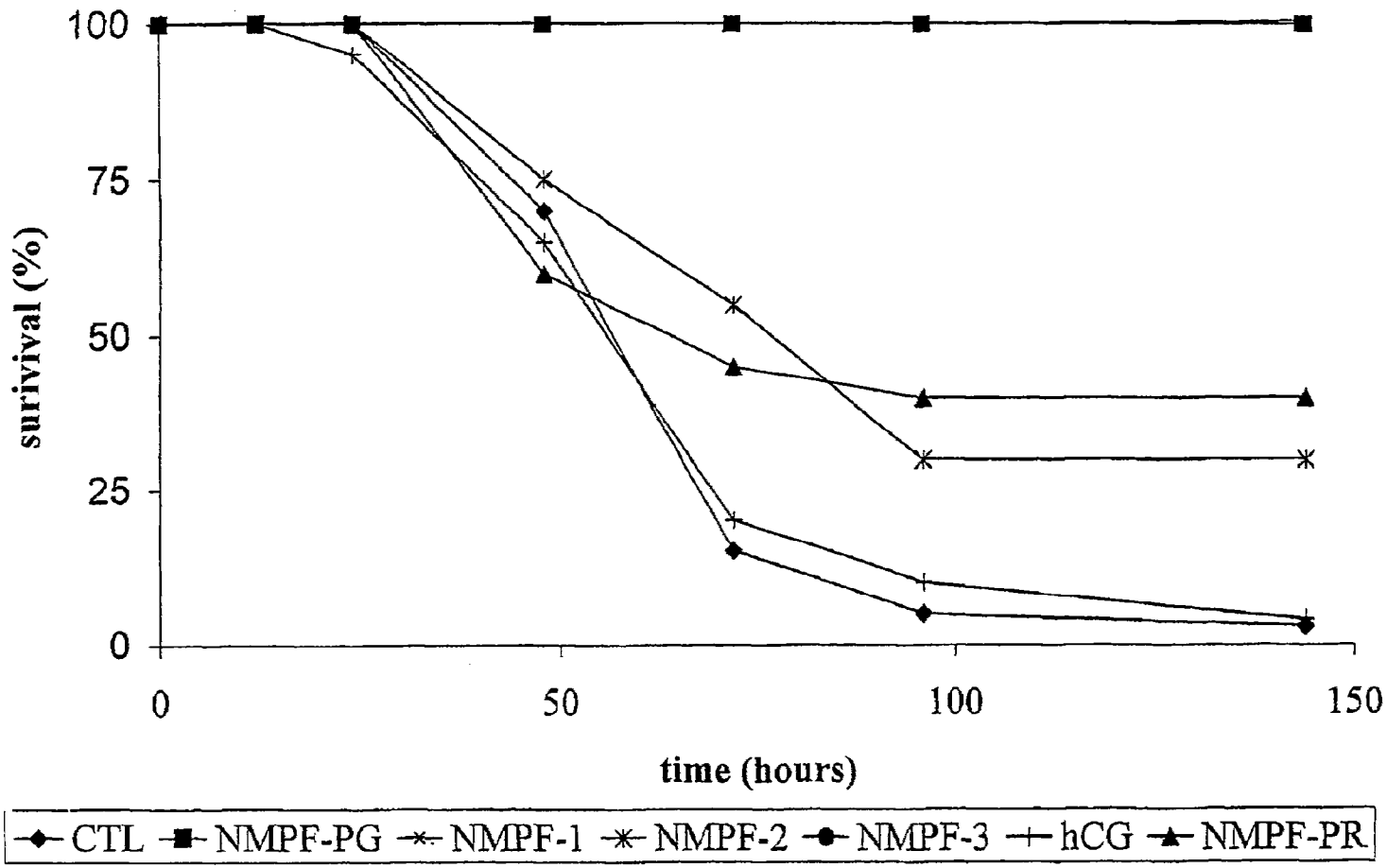
FIG. 3: This figure shows that PBS-treated BALB/c mice succumbed to shock from day 1 after high-dose LPS injection, with lower than 10% of mice alive on day 5. In contrast, 100% of the mice treated with NMPF from source Pregnyl, or its fractions NMPF-1 or NMPF-3 obtained from GPC 300 A column, were alive on day 5 ($P<0.001$), while groups of mice treated with NMPF-2 from source Pregnyl or Dexamethalsone (data not shown) demonstrated around 25% of survivors. Not all commercial hCG preparations showed NMPF activity; for example NMPF from source Profasi showed only partial anti-shock activity (around 40% survival).
Figure 4:
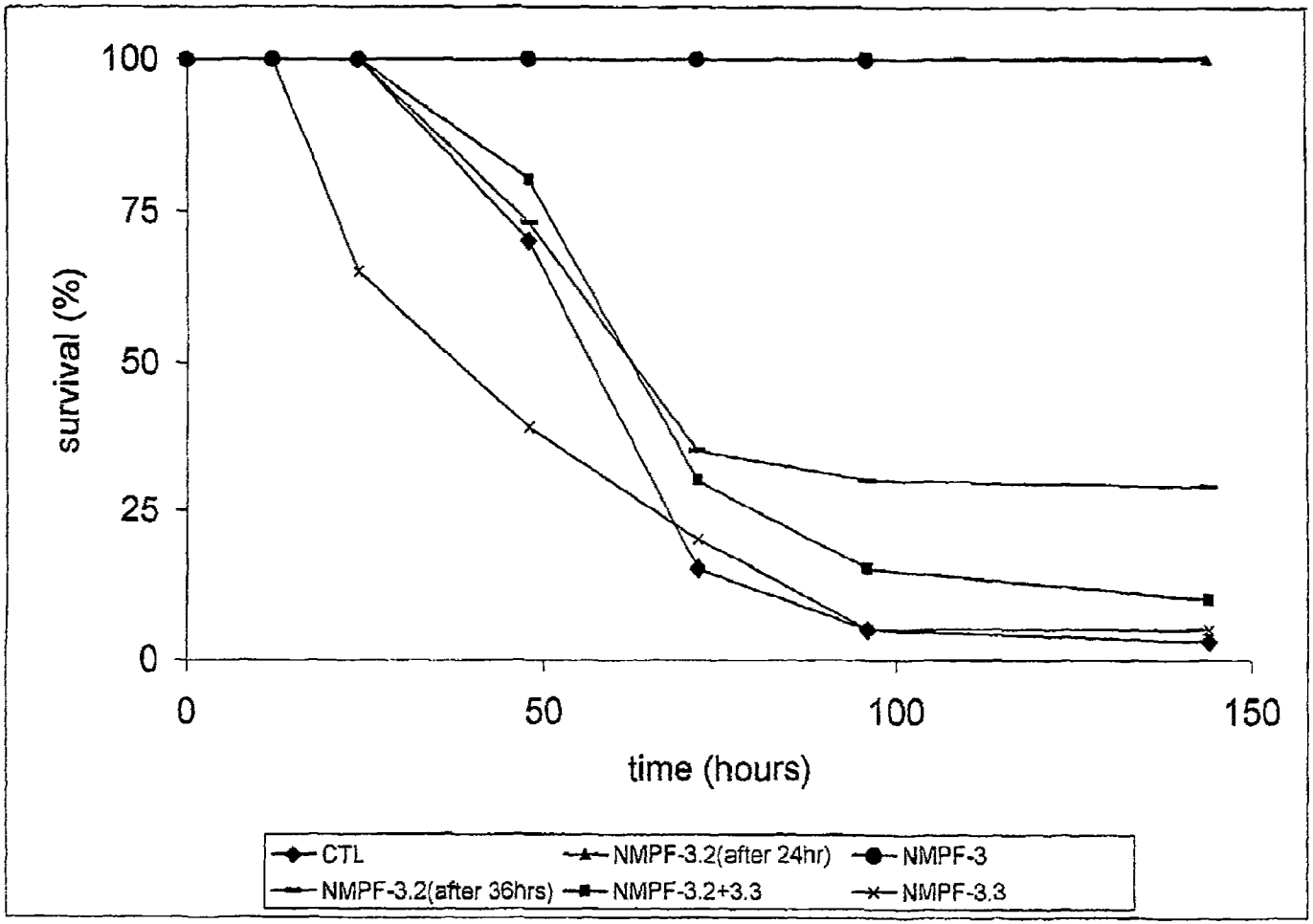
FIG. 4: This figure shows anti-shock activity in a pretested active batch resided in a fraction NMPF-3 and thereof derived NMPF-3.2 fraction which inhibit shock even after 24 hrs. and 36 hrs. of shock induction. In addition in all mice treated with NMPF-3.2 fraction alone, septic shock was inhibited and they had sickness scores lower than 2, while this anti-shock activity of NMPF-3.2 fraction was inhibited with NMPF-3.3. NMPF-3.3 treatment alone accelerated shock and the treated mice died even earlier than PBS treated mice.
Figure 5:
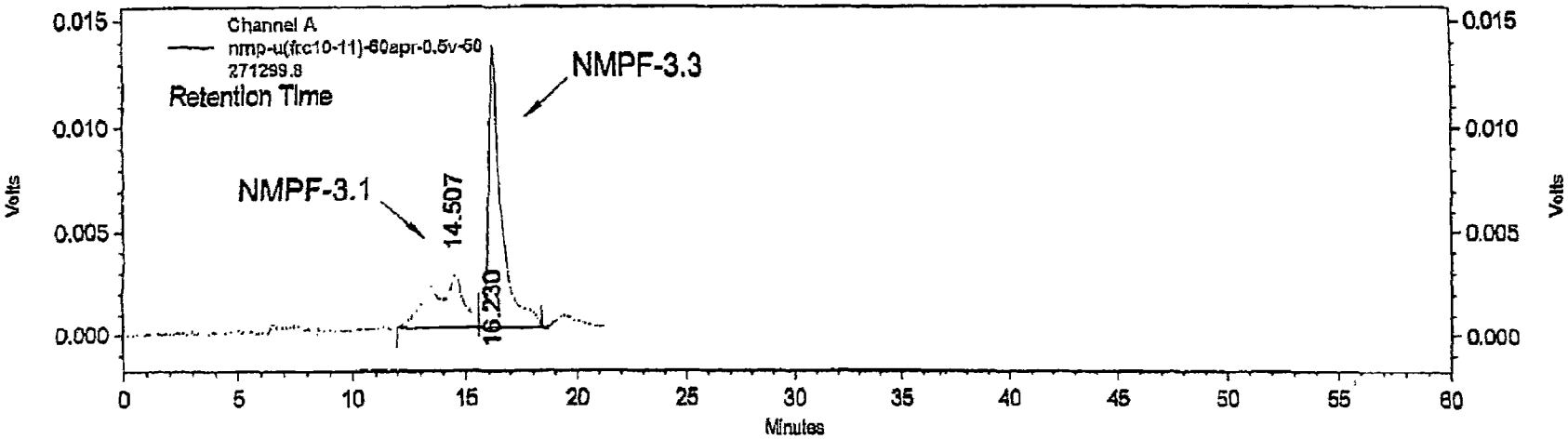
FIG. 5: This figure shows macrosphere GPC 60A chromatogram of pooled NMPF-3.2 and NMPF-3.3 fractions from first trimester pregnancy urine (containing anti-shock activity). This figure shows that the ratio between fraction NMPF-3.2 and NMPF-3.3 is around 1:2.2 (see text).
Figure 6:
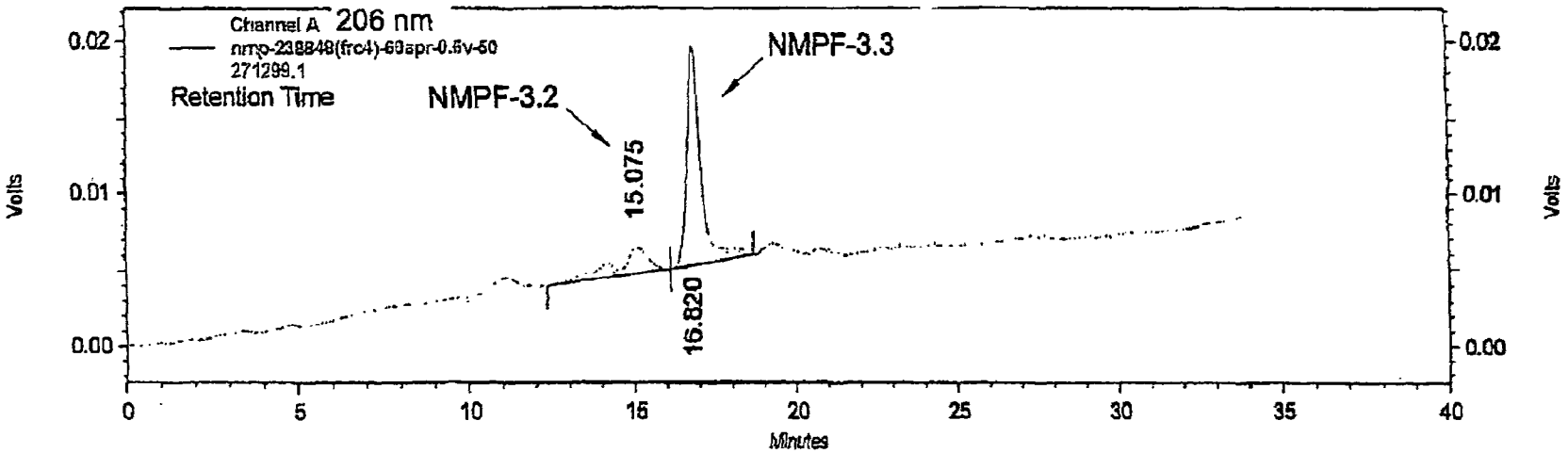
FIG. 6: This figure shows macrosphere GPC GOA chromatogram of pooled NMPF-3.2 and NMPF-3.3 fractions from non-active Pergnyl batch (containing no anti-shock activity). This figure shows that the ratio between fraction NMPF-3.2 and NMPF-3.3 is around 1:3.4 (see text).
Figure 7:
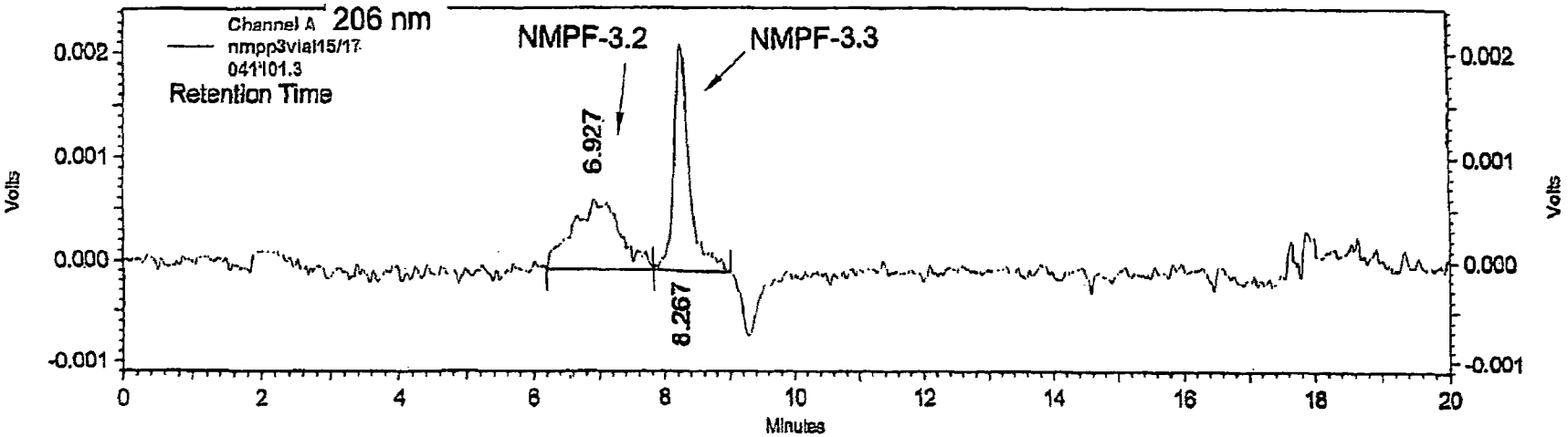
FIG. 7: This figure shows macrosphere GPC 60A chromatogram of pooled NMPF-3.2 and NMPF-3.3 fractions from active Pergnyl batch (containing anti-shock activity). This figure shows that the ratio between fraction NMPF-3.2 and NMPF 3.3 is around 1:1 (see text).
Figure 8:
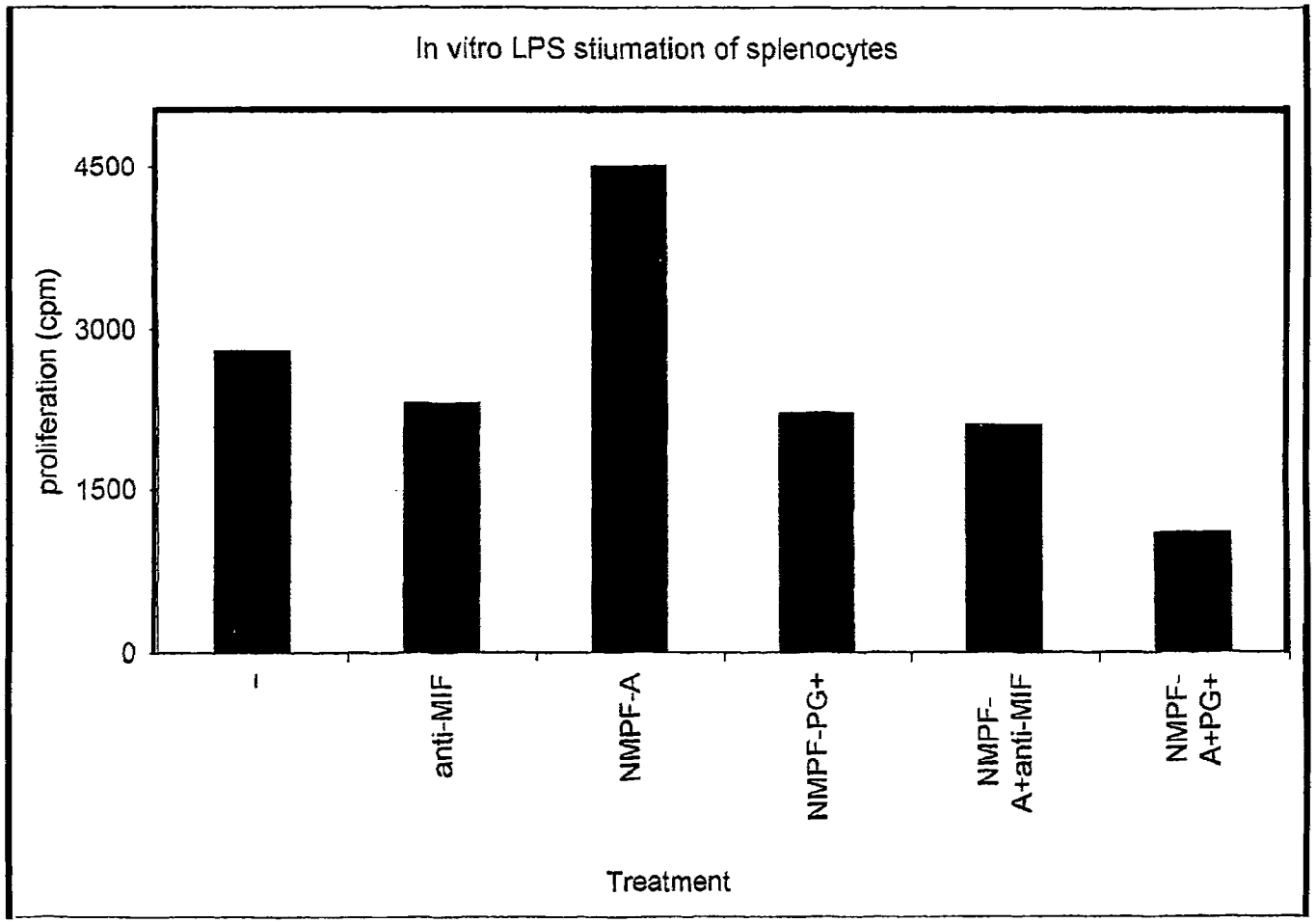
FIG. 8: This figure shows LPS induced proliferation of splenocytes. Anti-MIF and NMPF (from active Pregnyl batch, NMPF-PG*) are both able to decrease LPS stimulated proliferation as compare to LPS alone, and together they show synergistically inhibitory effect on LPS stimulated proliferation.
Figure 9:
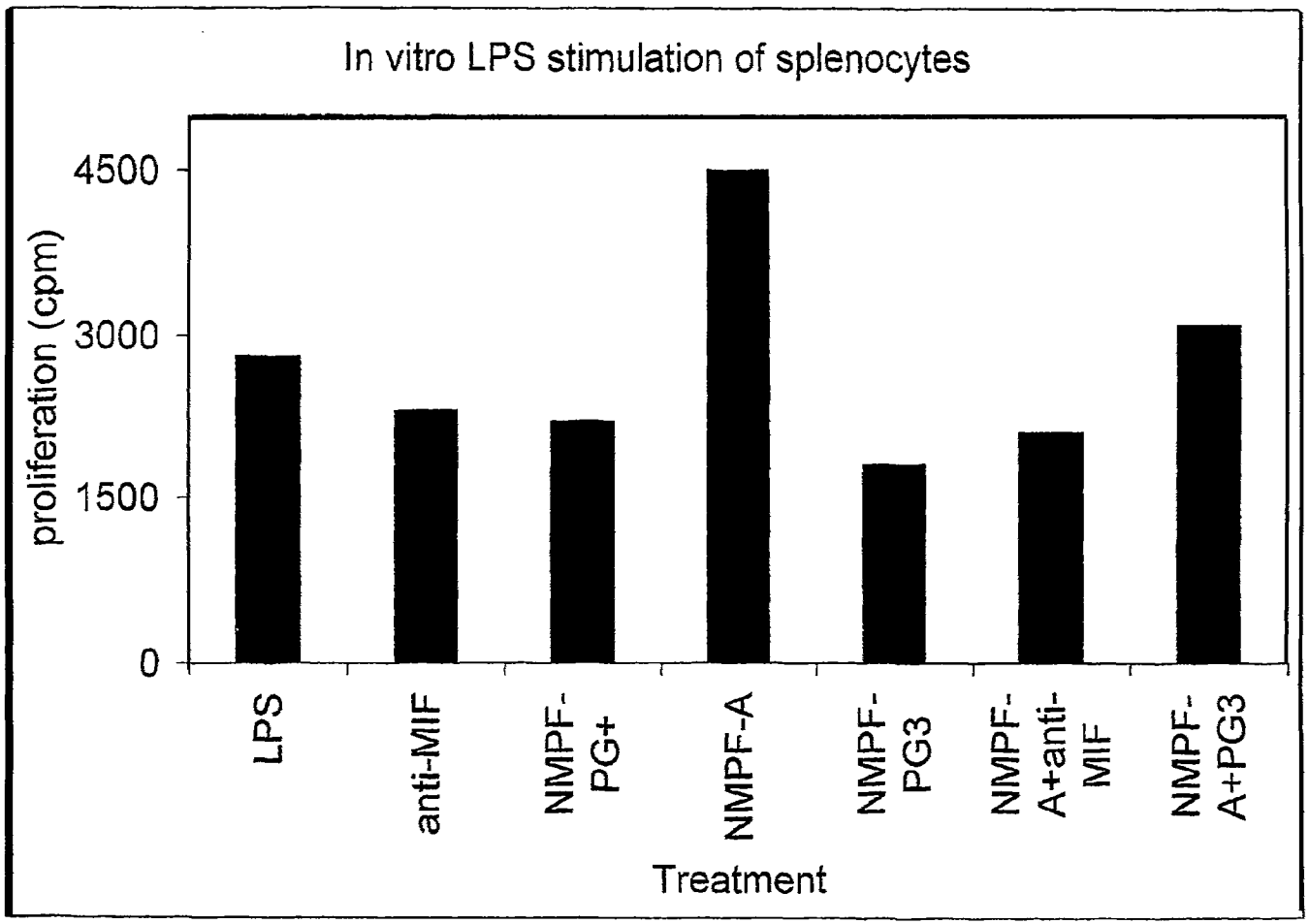
FIG. 9: This figure shows NMPF-A (APL) accelerate LPS induced proliferation, while this proliferation is inhibited by anti-MIF and NMPF-G*.
Figure 10:
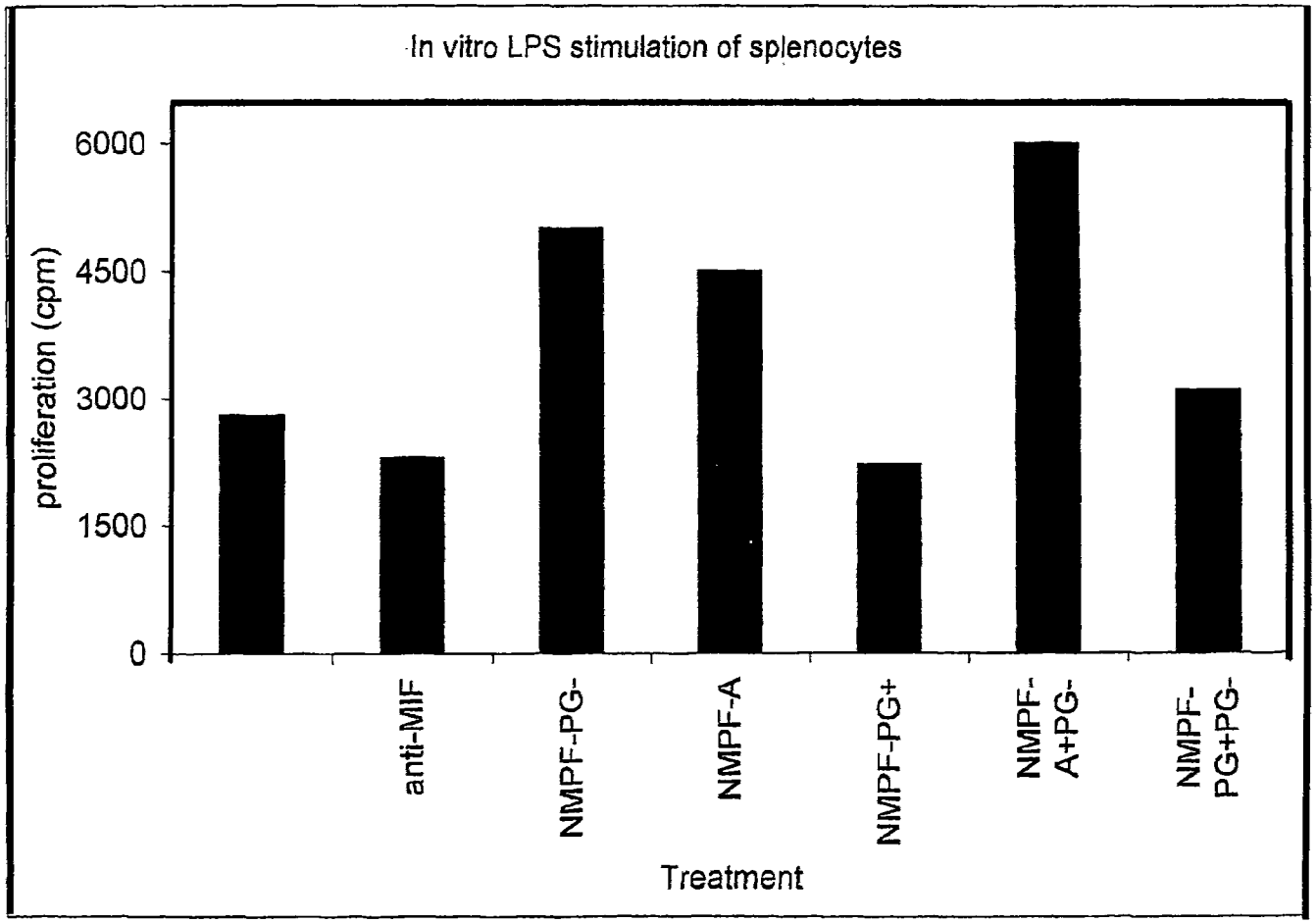
FIG. 10: This figure shows that low molecular weight fraction (NMPF-PG3) from active Pregnyl batch (NMPF-PG*) as well as complete NMPF-PG+ are able to inhibit NMPF-A accelerated LPS induced proliferation.
Figure 11:
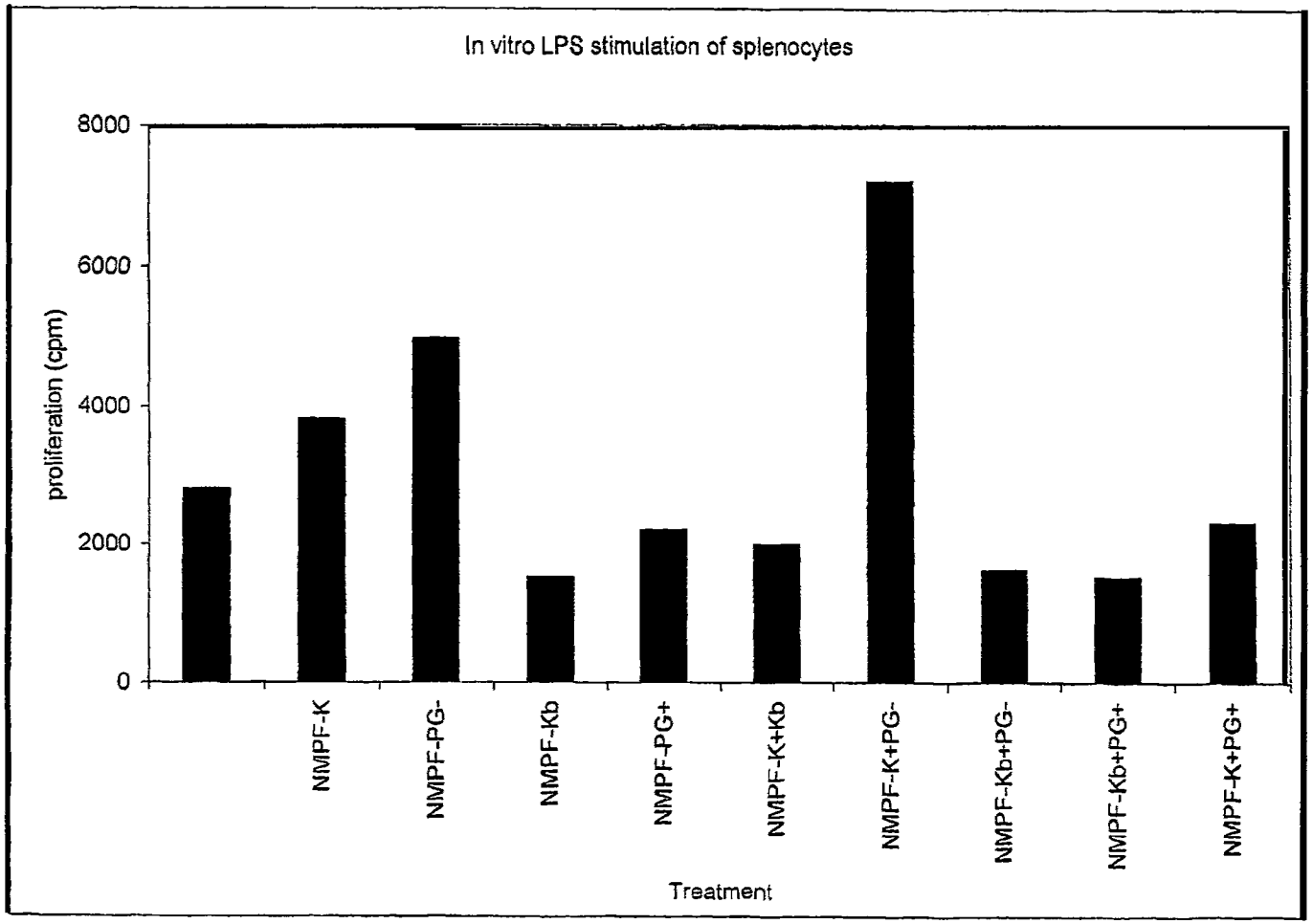
FIG. 11: This figure shows that NMPF-PG (non-active Pregnyl batch) and NMPF-A or in combination (synergistically) increase LPS induced proliferation, while NMPF-PG* inhibits this proliferation same as anti-MIF (see FIGS. 8-9).
Figure 12:
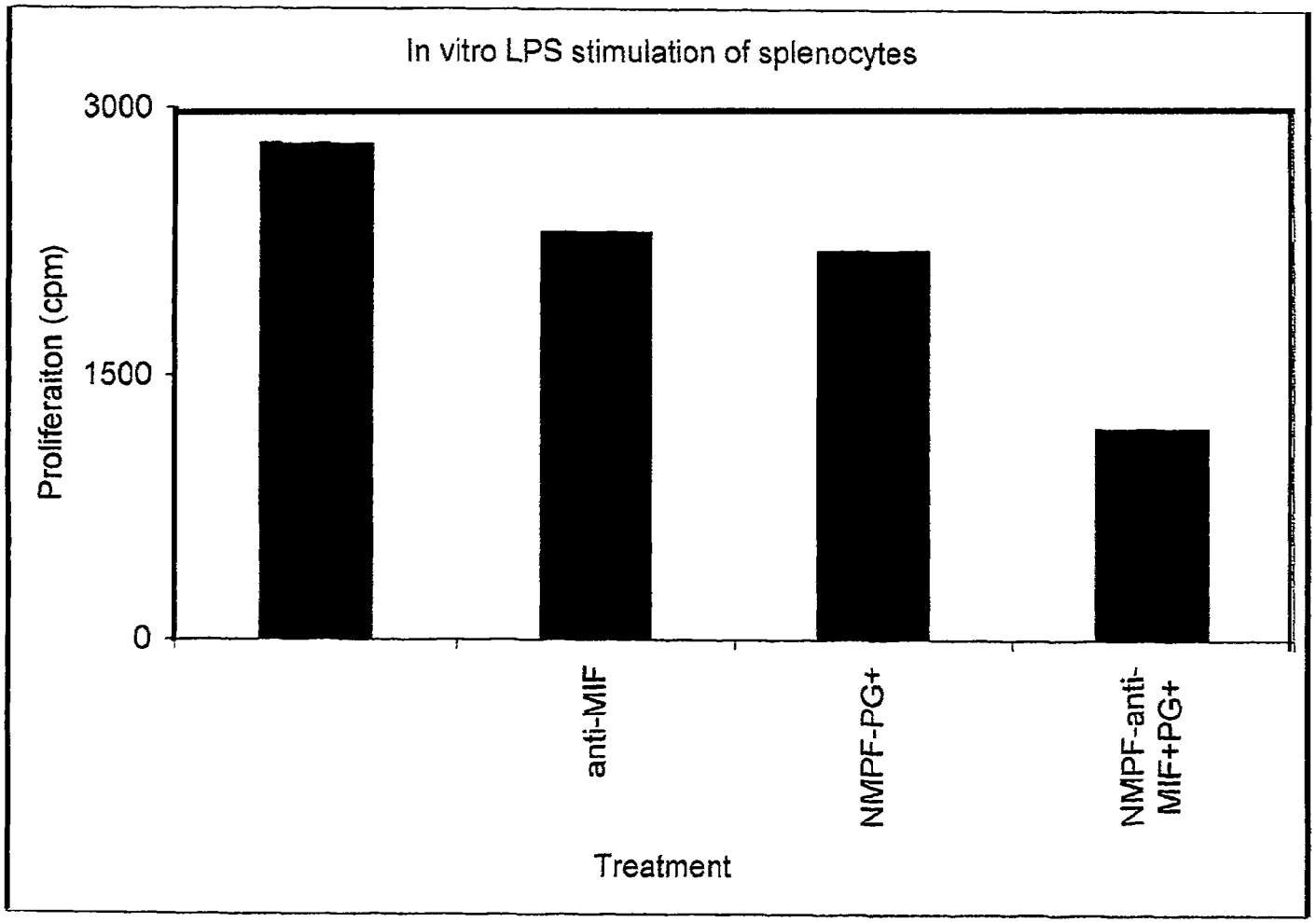
FIG. 12: This figure shows that NMPF-K accelerates LPS induced proliferation same as NMPF-PG⁻, while in combination they synergistically increase proliferation and this increase in proliferation is inhibited with NMPF-Kb or NMPF-PG*. In addition, NMPF-Kb and NMPF-PG* synergistically decrease LPS induced proliferation.
Figure 13:
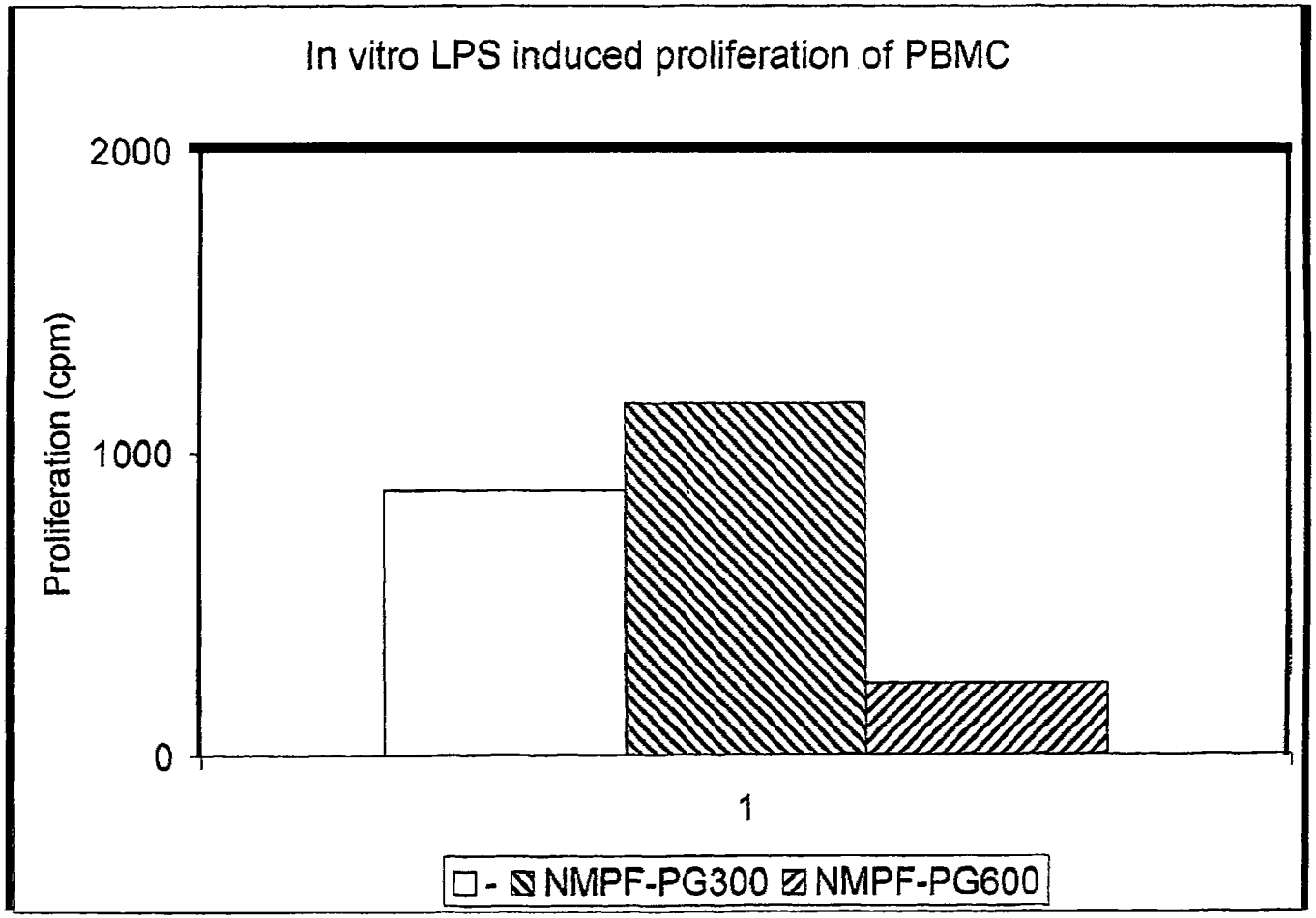
FIGS. 13-15: These figures show dose dependent (300 and 600 IU/ml) inhibitory effect of NMPF-PG+ on LPS and PHA/IL-2 induced proliferation of PBMC isolated from septic shock patient. Same effect was observed in medium conditions alone.
Figure 14:
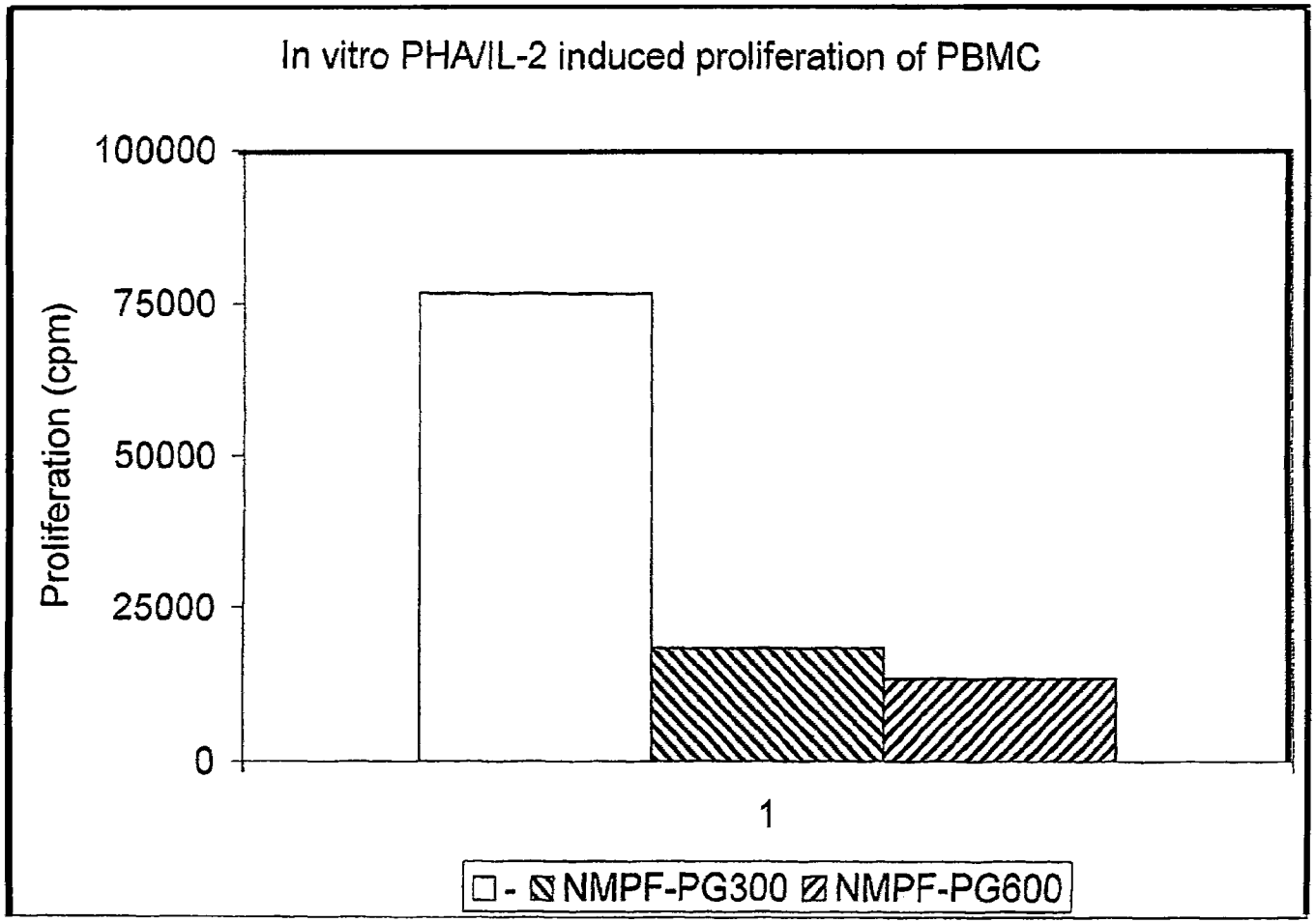
Figure 15:
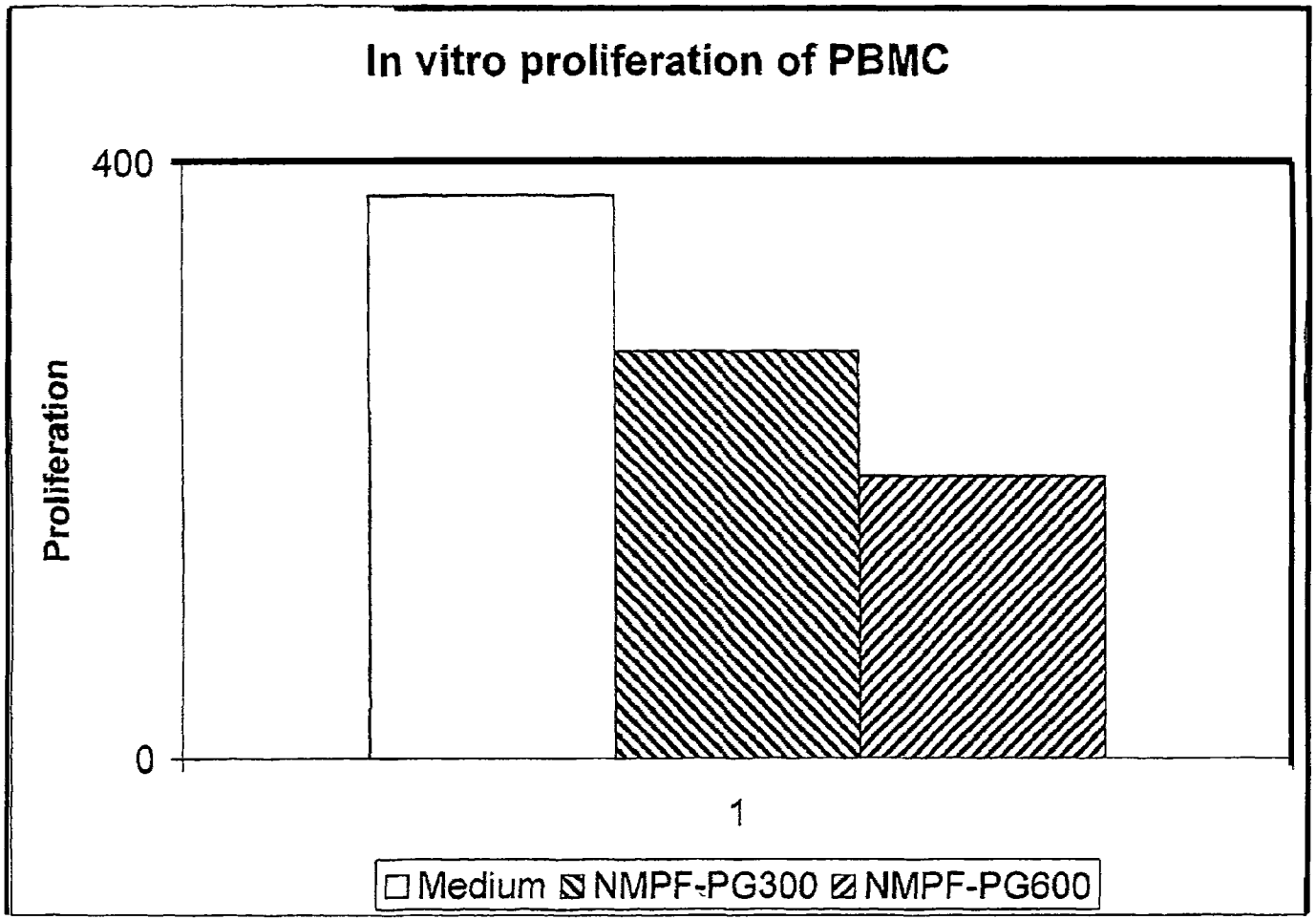
Figure 16:
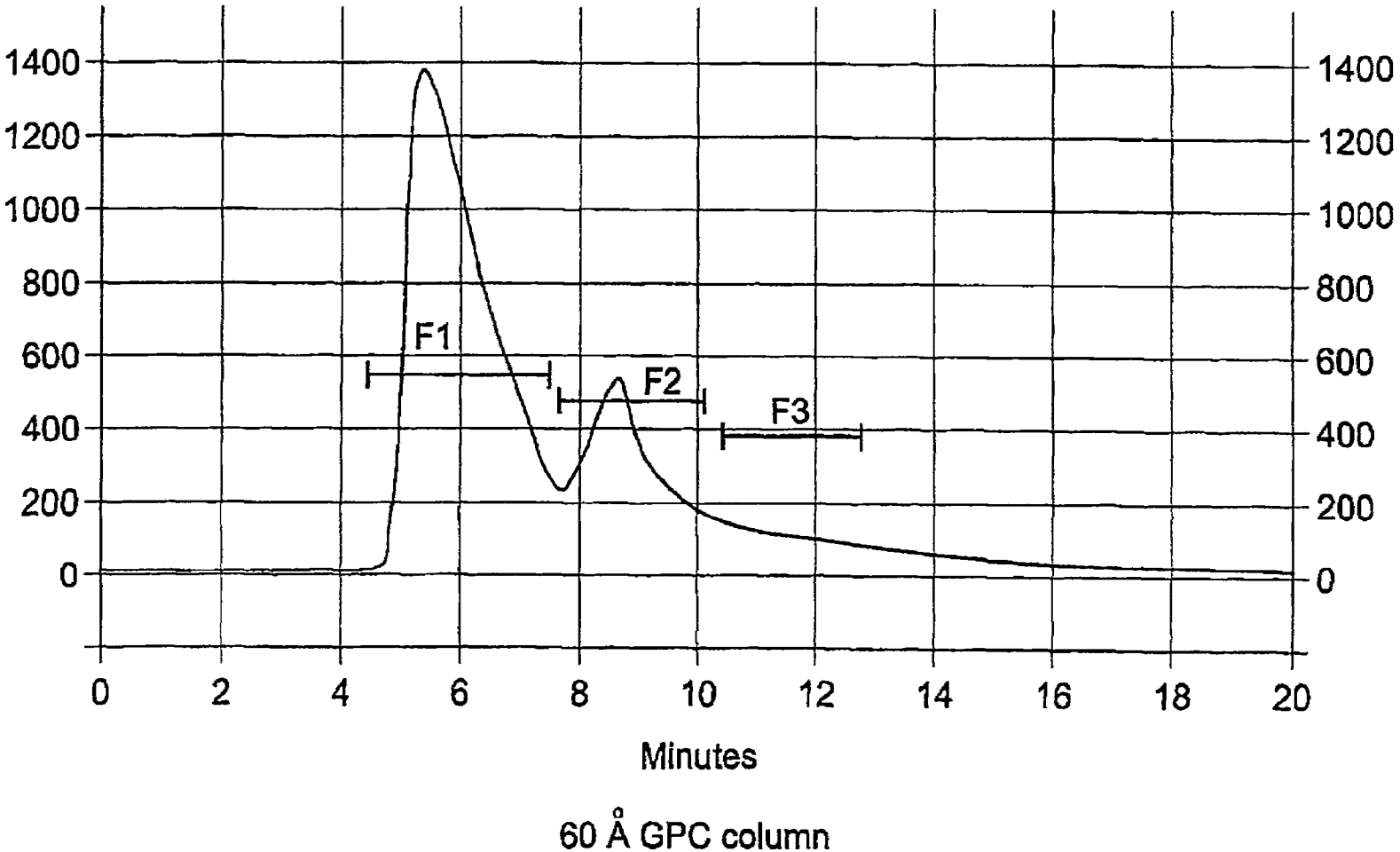
FIG. 16: This figure shows macrosphere GPC 60A chromatogram of c-hCG. Three selected areas were fractionated, 60A-F1 which elutes apparently with molecular weight of >10 kDa, 60A-F2 which elutes apparently with molecular weight between 10 kDa-1 kDa and 60A-F3 elutes apparently with molecular weight lower then 1 kDa. All fractions were tested for anti-shock activity.
Figure 17:
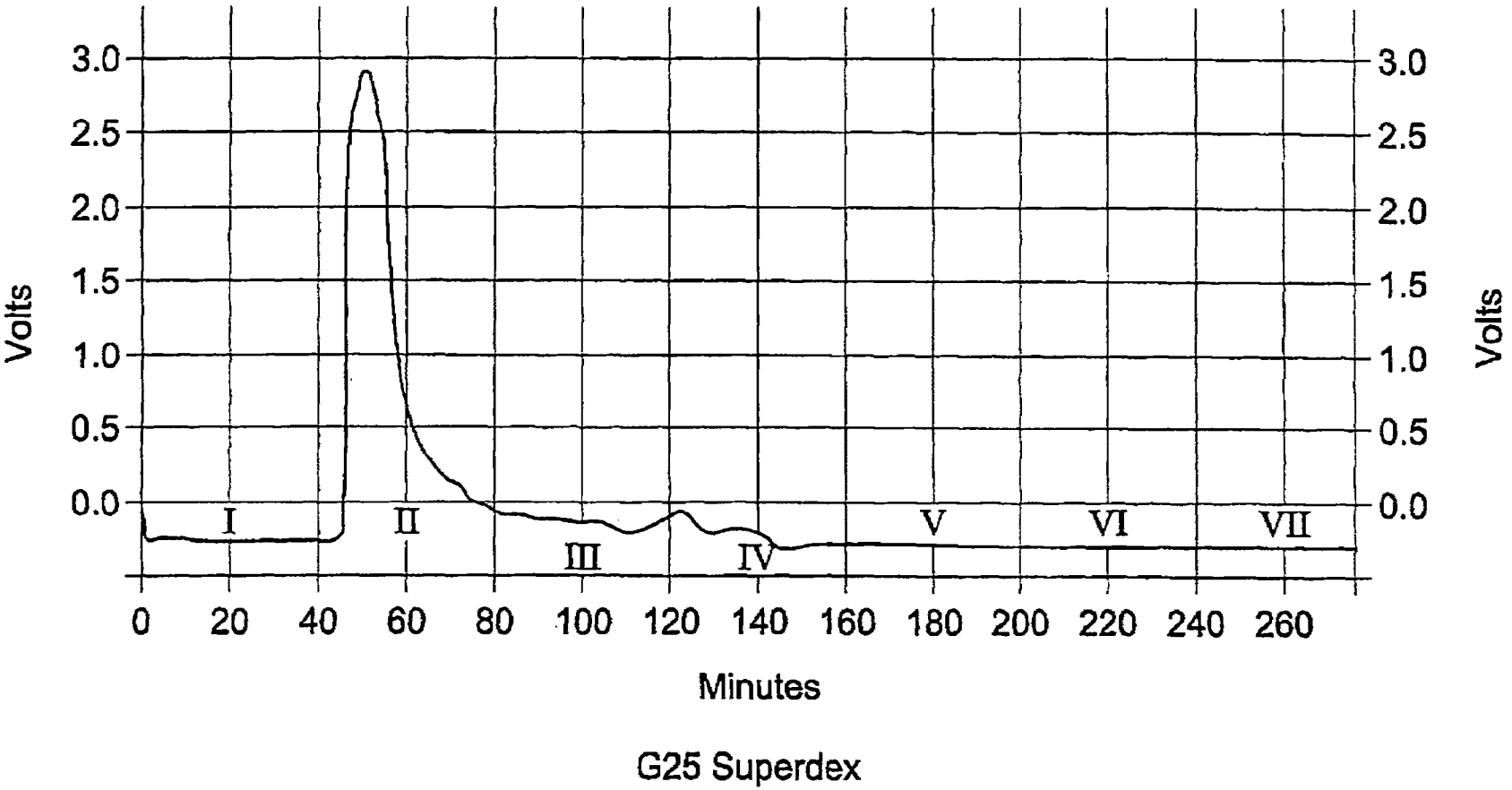
FIG. 17: This figure shows G25 Superdex chromatogram of c-hCG. 100 mL fractions were collected (fraction I-VII) and all fractions were tested for anti-shock activity.
Figure 18:
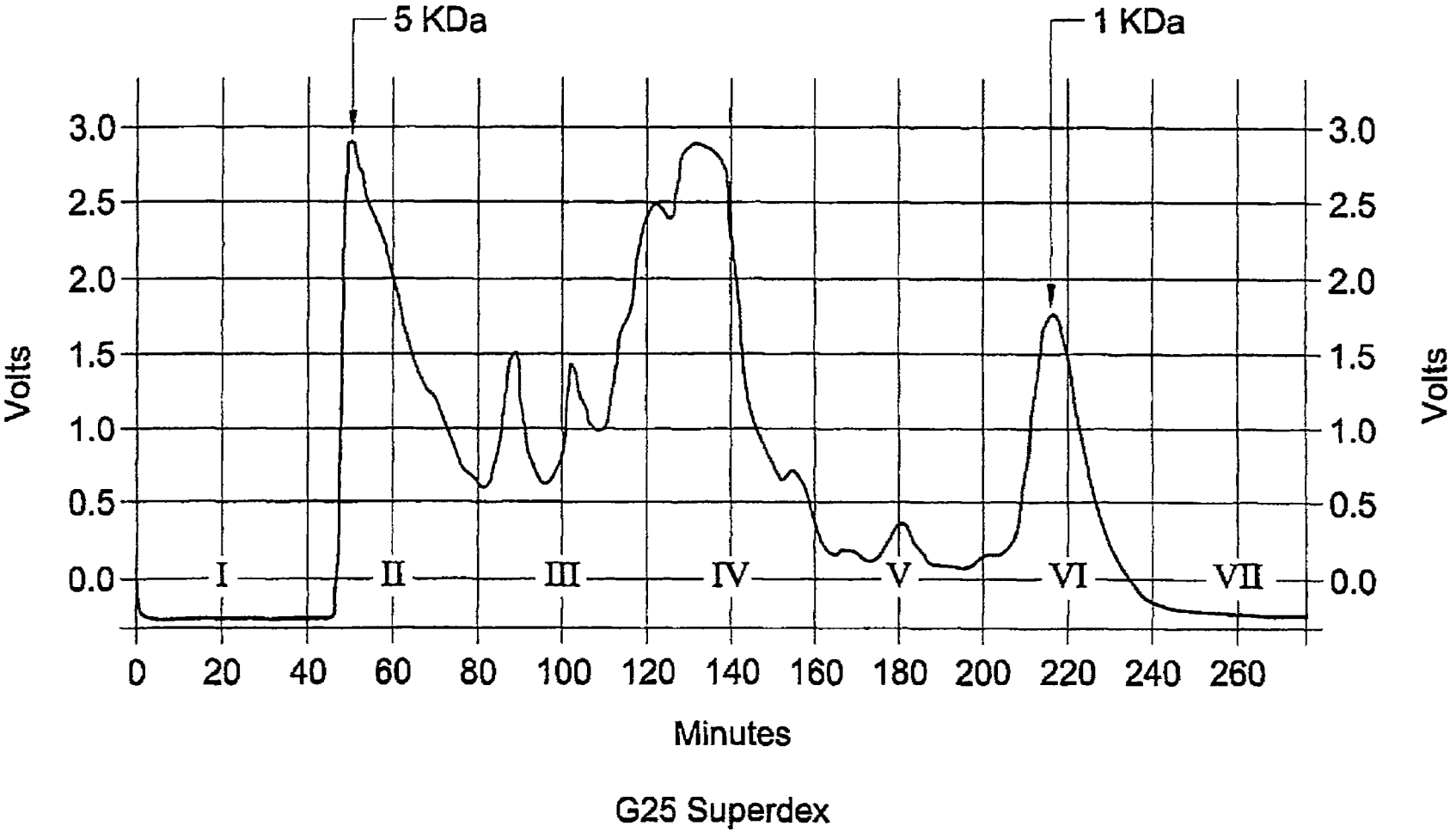
FIG. 18: This figure shows G25 Superdex chromatogram of first trimester pregnancy urine from healthy individuals. 100 mL fractions were collected (fraction I-VII) and all fractions were tested for anti-shock activity.
Figure 19:
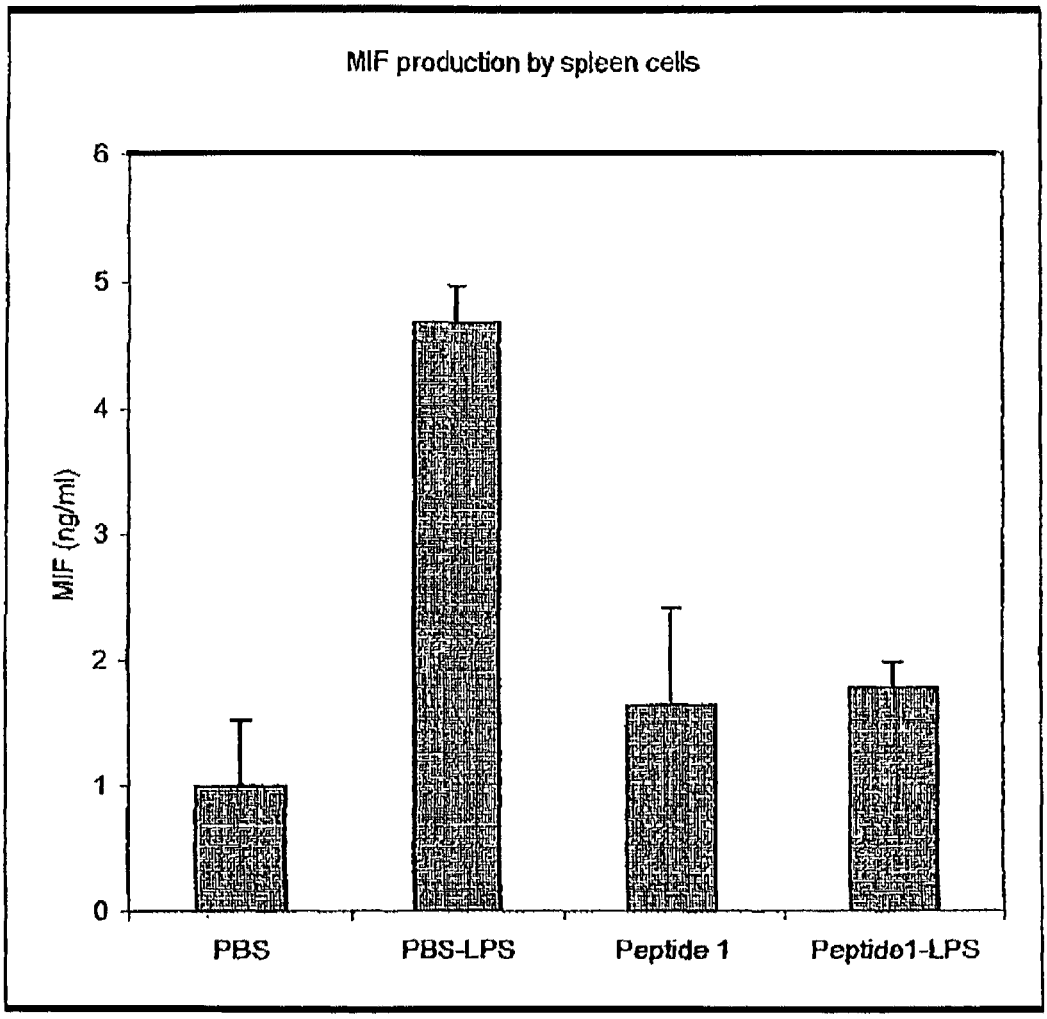
FIG. 19: This figure shows that in vivo treatment with LPS increased MIF production as compared to PBS treated mice, while Peptide 1 treatment after the shock induction inhibited MIF production. No effect on MIF production was found in mice treated with Peptide 1 alone.
Figure 20:
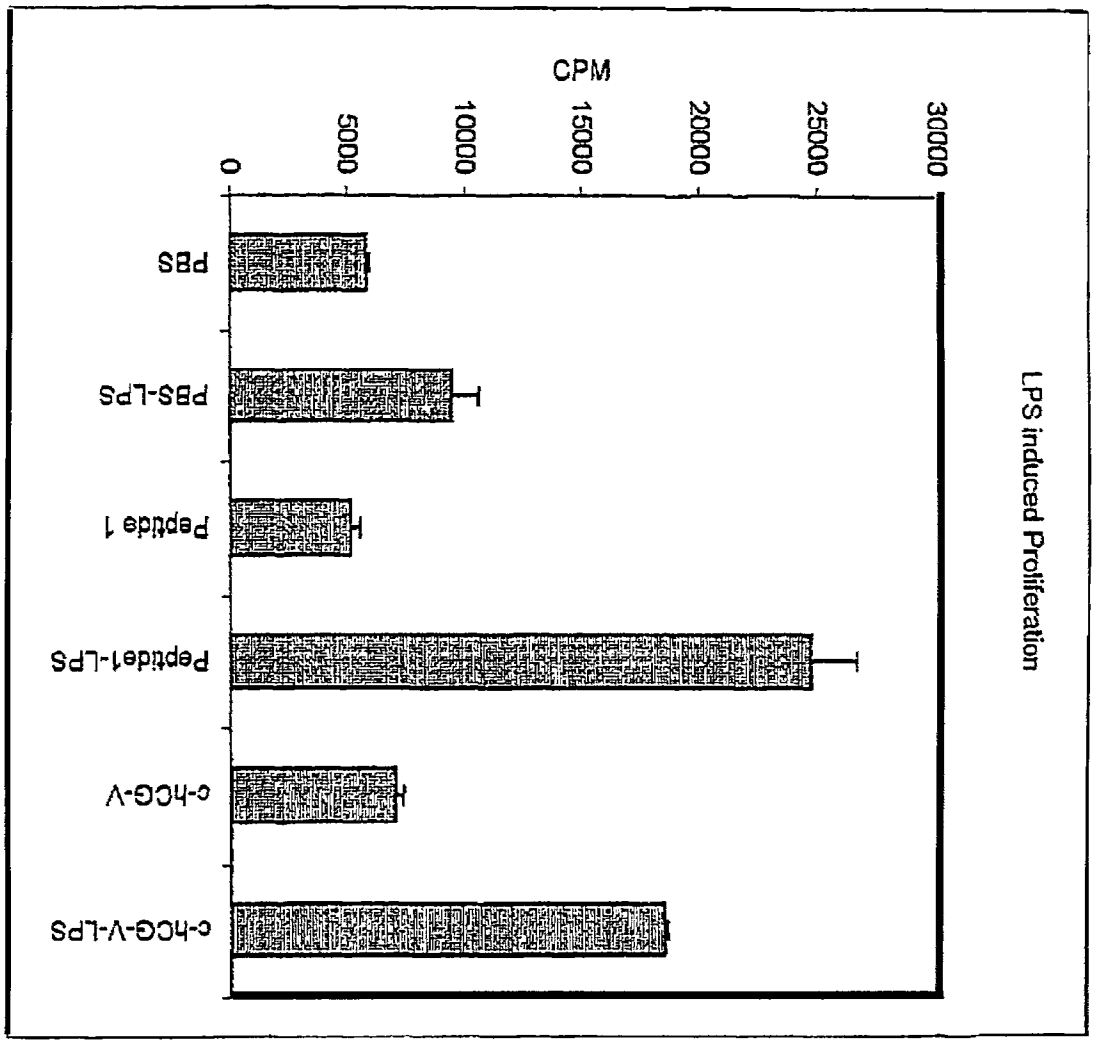
FIG. 20: This figure shows that after restimulation with LPS in vitro, splenocytes from LPS treated mice have a greater capacity to proliferate in vitro as compared to PBS treated mice. On the other hand, splenocytes from LPS+ peptide 1 and LPS+c-hCG-V treated mice showed a much higher capacity to proliferate as compared to the LPS treated control mice. No differences in LPS induced proliferation was observed in mice treated with PBS, peptide 1 or c-hCG-V alone.
Figure 21:
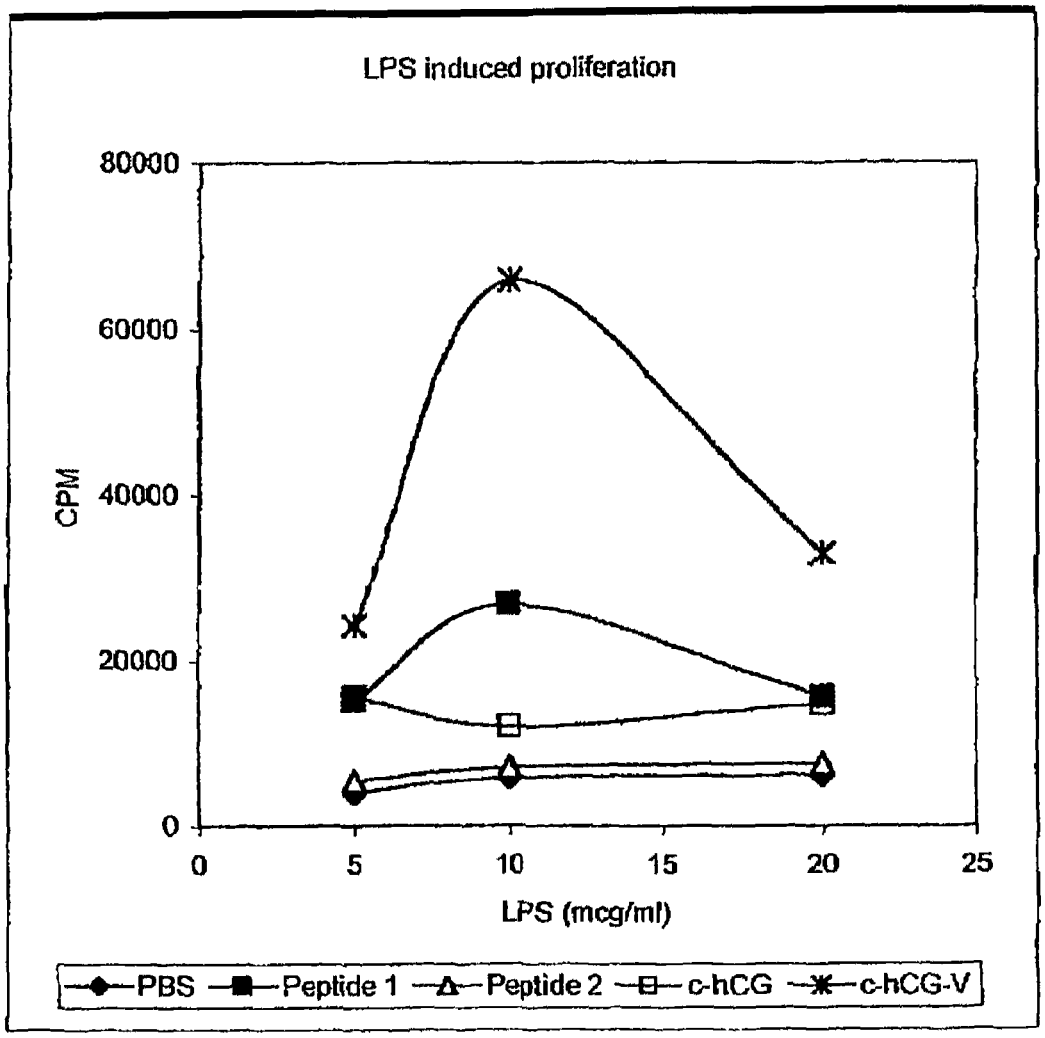
FIG. 21: This figure shows the effect of restimulation of splenocytes from in vivo treated mice with different doses of LPS in vitro.
Figure 22:
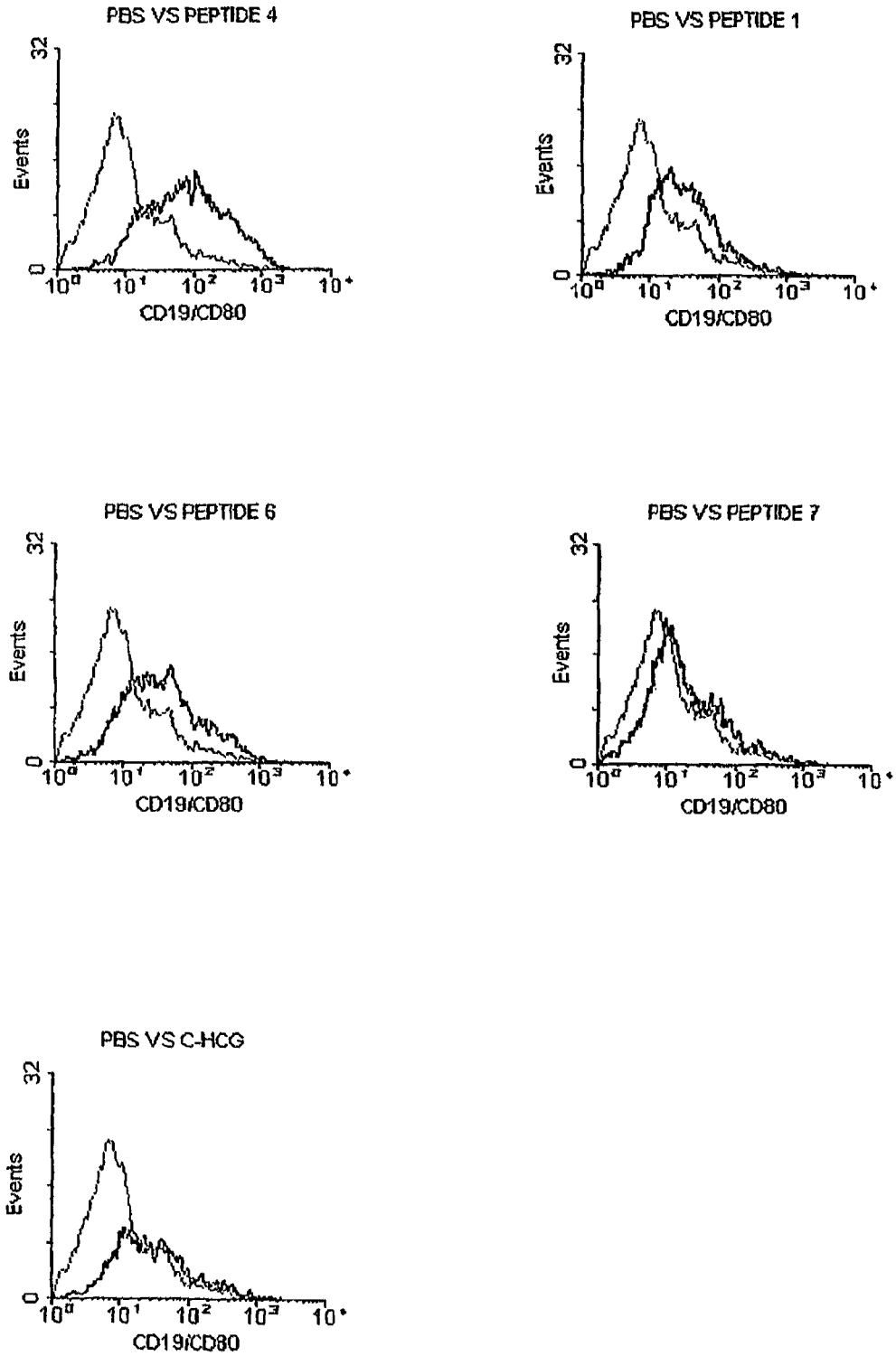
FIG. 22: This figure shows that the shock inhibitory activities (c-hCG, peptide 1, peptide 4 and peptide 6) increased the expression of CD80 molecule on CD19 cells as compared to PBS+LPS control group, whereas-minor effect was observed with peptide 7 which accelerates shock.
Figure 23:
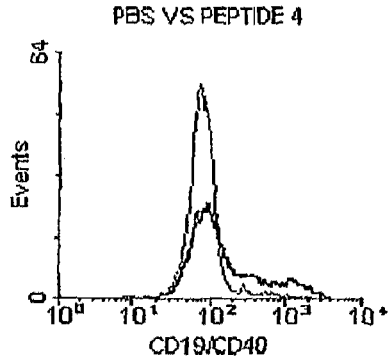
FIGS. 23-28: These figures show flow cytometry analysis on splenocytes from treated BALB/c mice.
Figure 23:
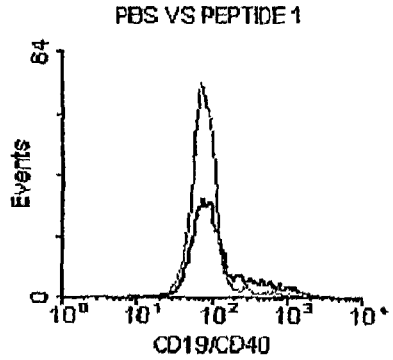
Figure 23:
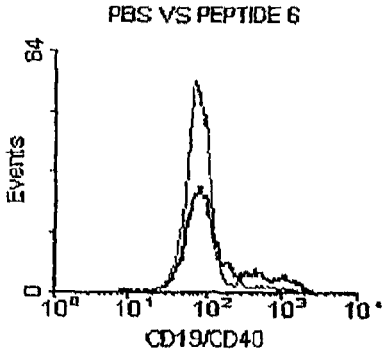
Figure 23:
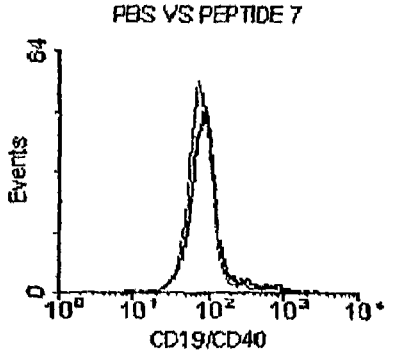
Figure 23:
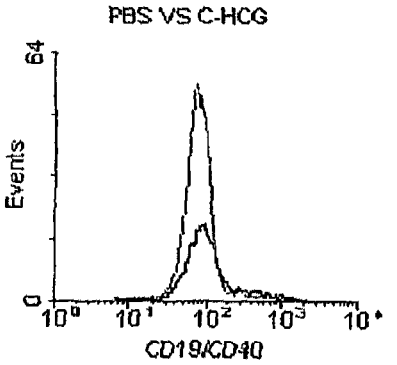
Figure 24:
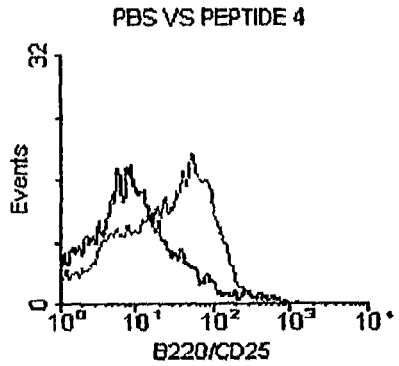
Figure 24:
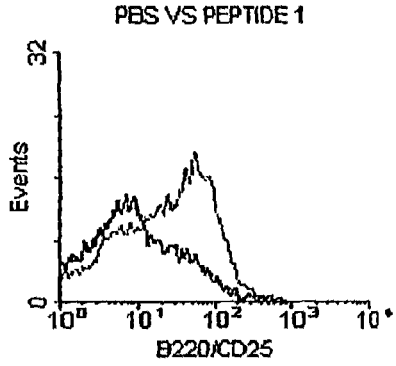
Figure 24:
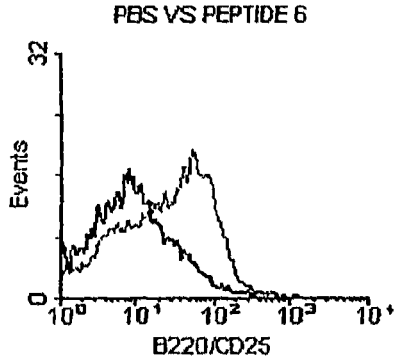
Figure 24:
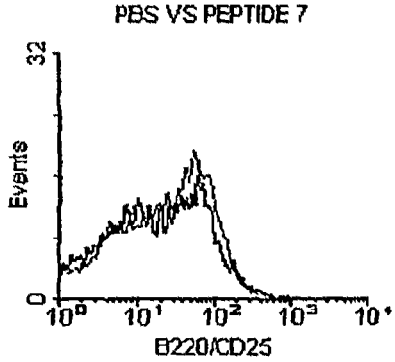
Figure 24:
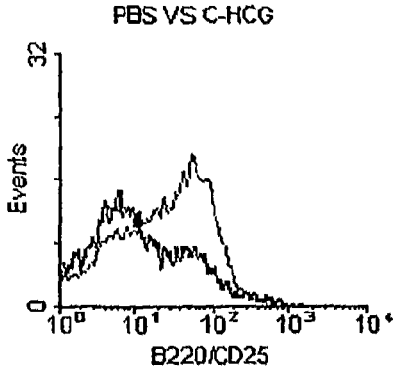
Figure 25:
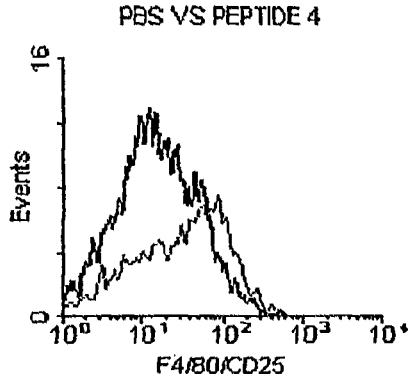
Figure 25:
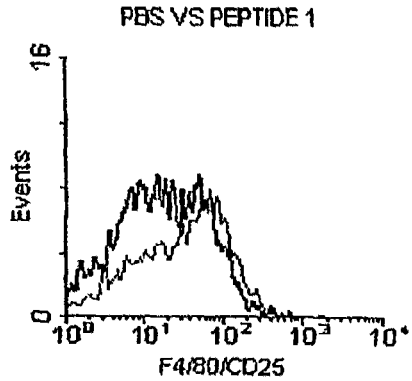
Figure 25:
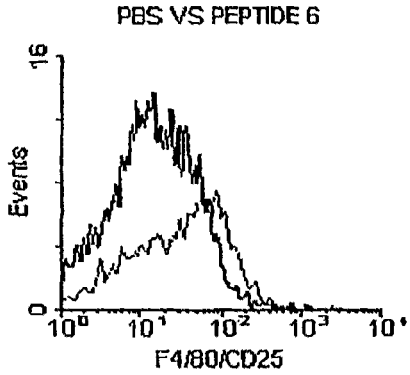
Figure 25:
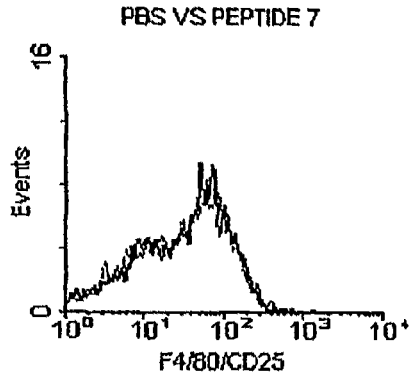
Figure 25:
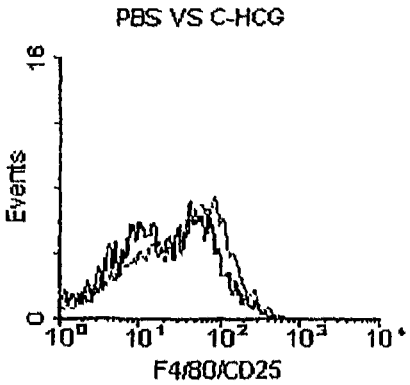
Figure 26:
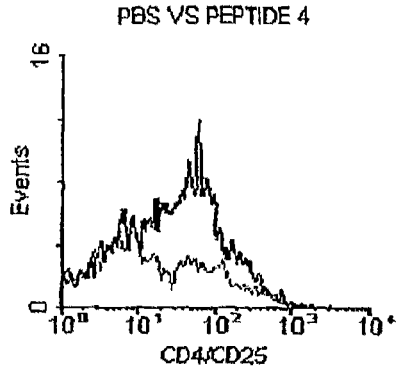
Figure 26:
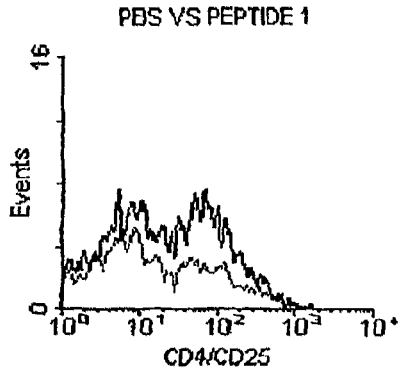
Figure 26:
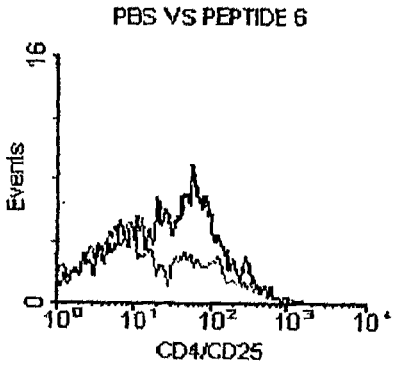
Figure 26:
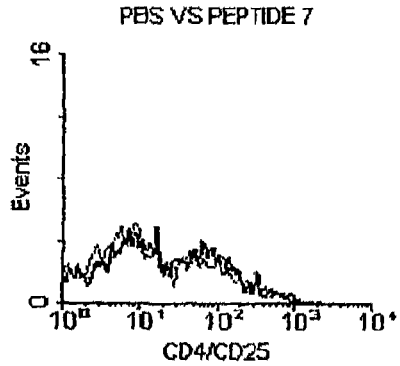
Figure 26:
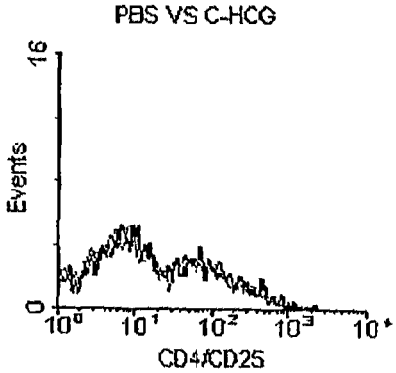
Figure 27:
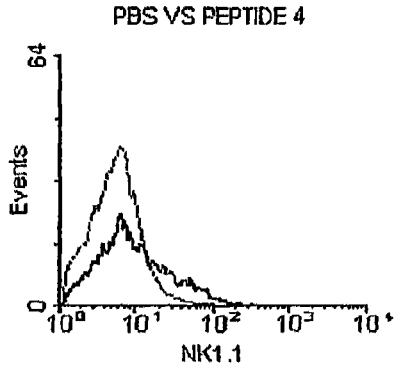
Figure 27:
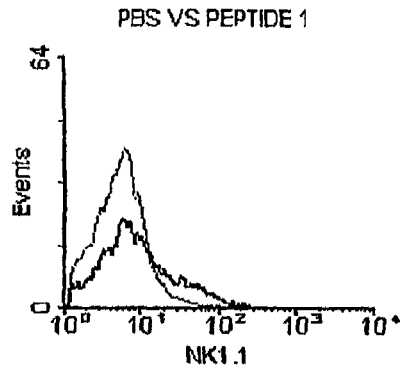
Figure 27:
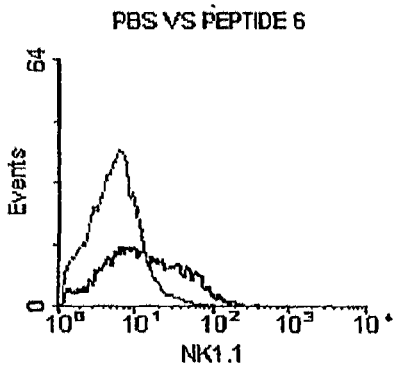
Figure 27:
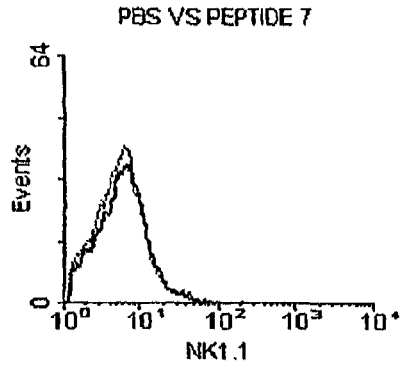
Figure 27:
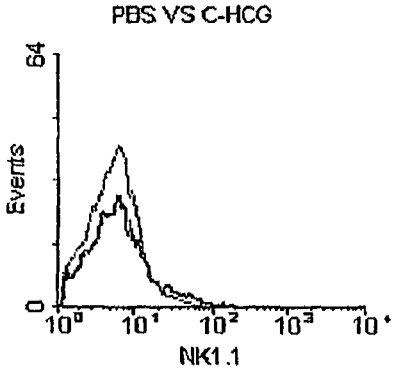
Figure 28:
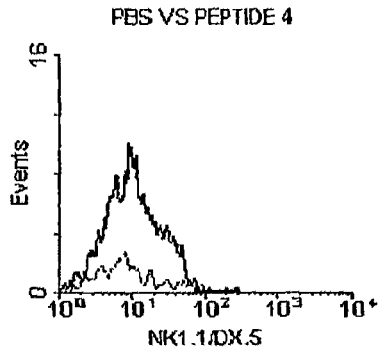
Figure 28:
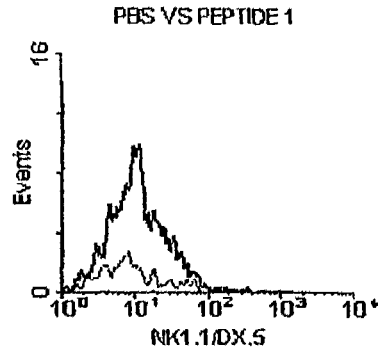
Figure 28:
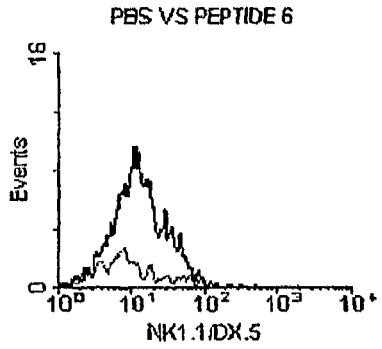
Figure 28:
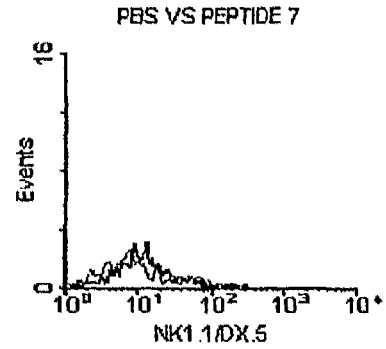
Figure 28:
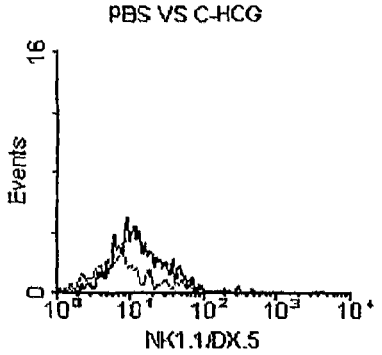
Figure 29:
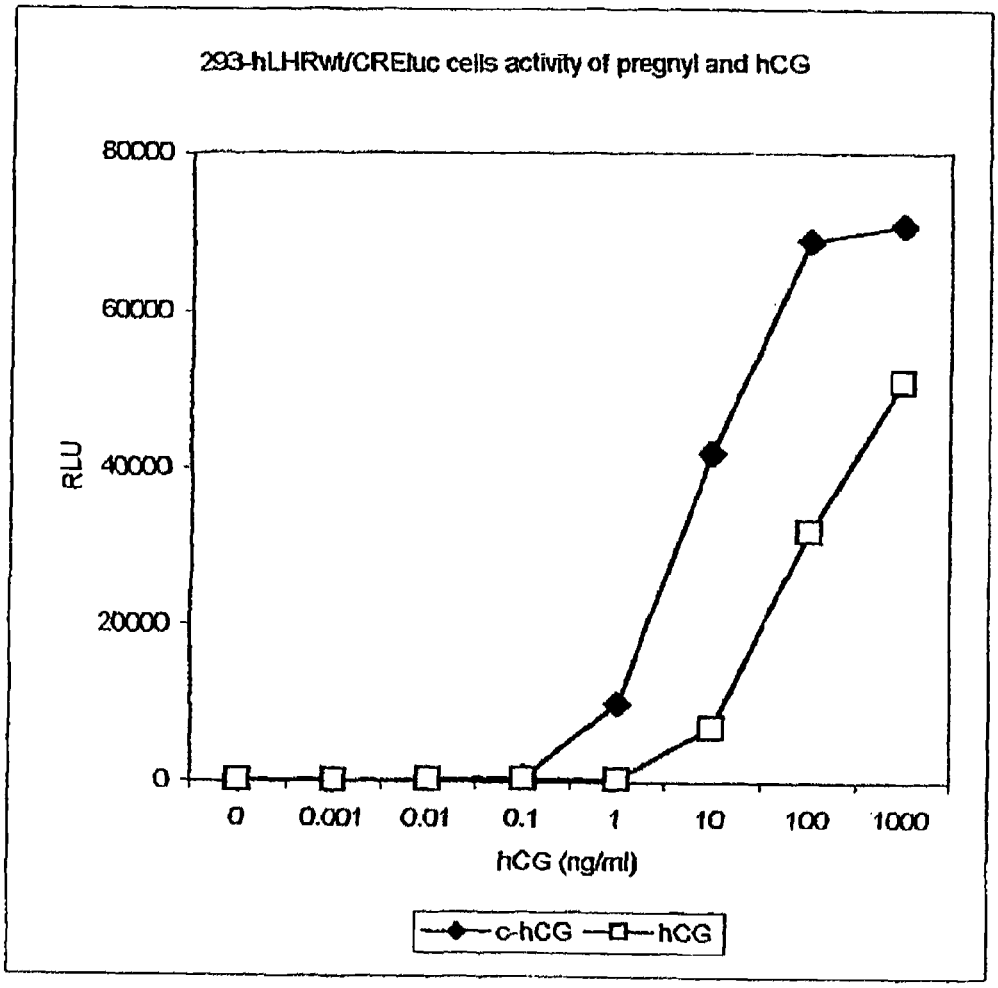
FIGS. 29-31: These figures show that hCG and c-hCG bind to 293-hLHRwt/CREluc cells and induce dose-dependent luciferase activity (FIG. 29), while no effect was observed in luciferase activity with peptide 1 (VLPALPQVVC (SEQ ID NO:3)), 2 (LQGVLPALPQ (SEQ ID NO:4)), 4 (LQGV (SEQ ID NO:8)), 6 (VLPALP (SEQ ID NO:12)) and low molecular weight fraction c-hCG-V (FIG. 30). Moreover, addition of peptide 1, 2, 4, 6 and fraction c-hCG-V in the presence of hCG also did not show effect on luciferase activity induce by hCG itself (FIG. 31).
Figure 30:
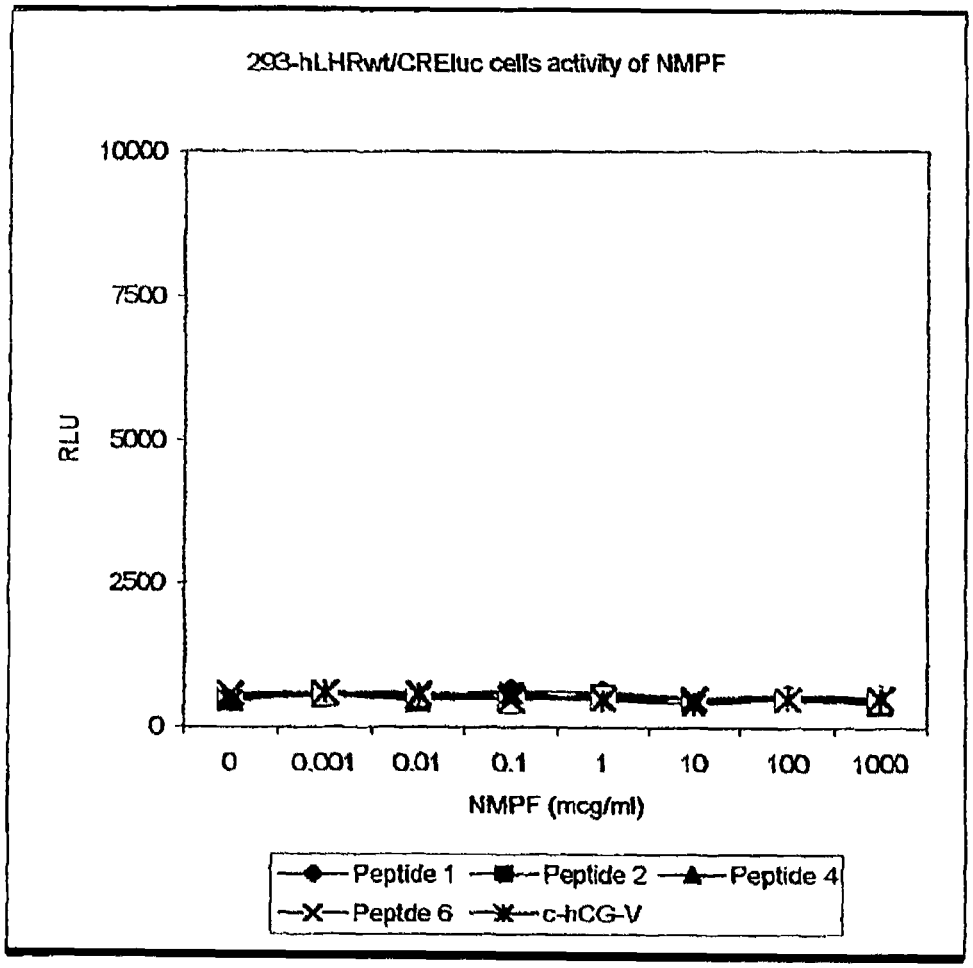
Figure 31:
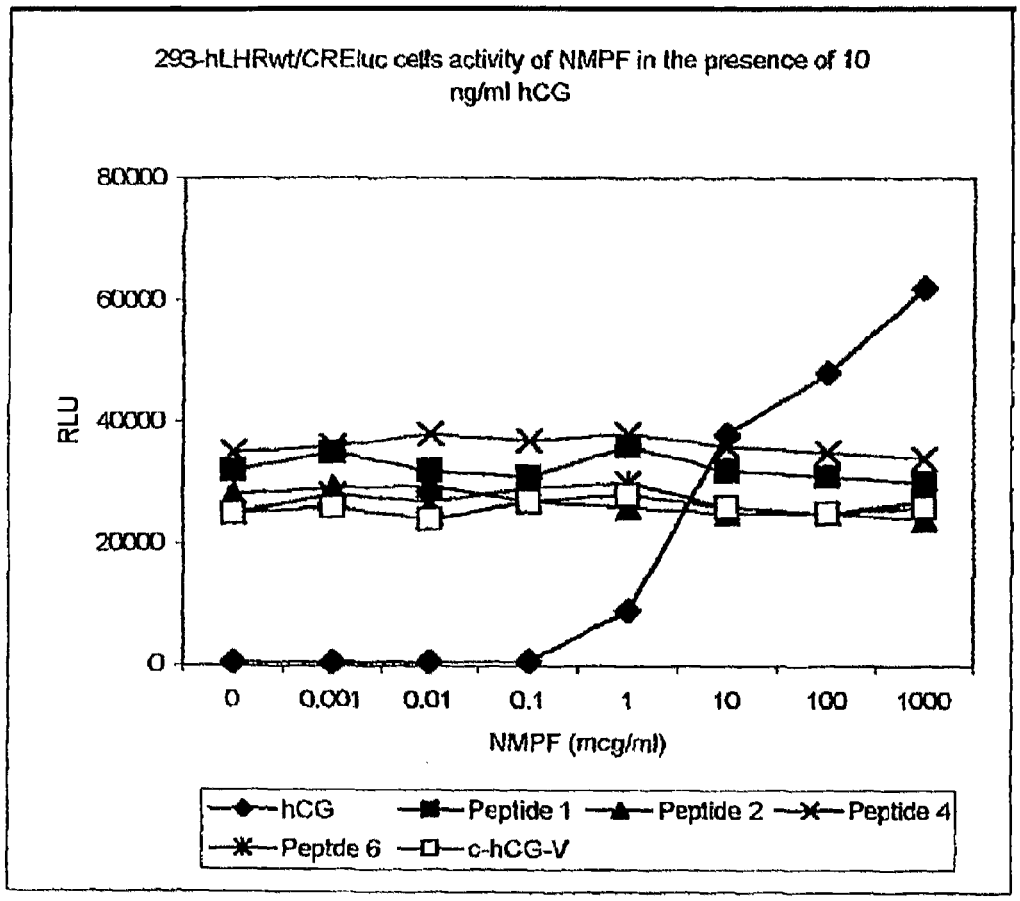
Figure 32:
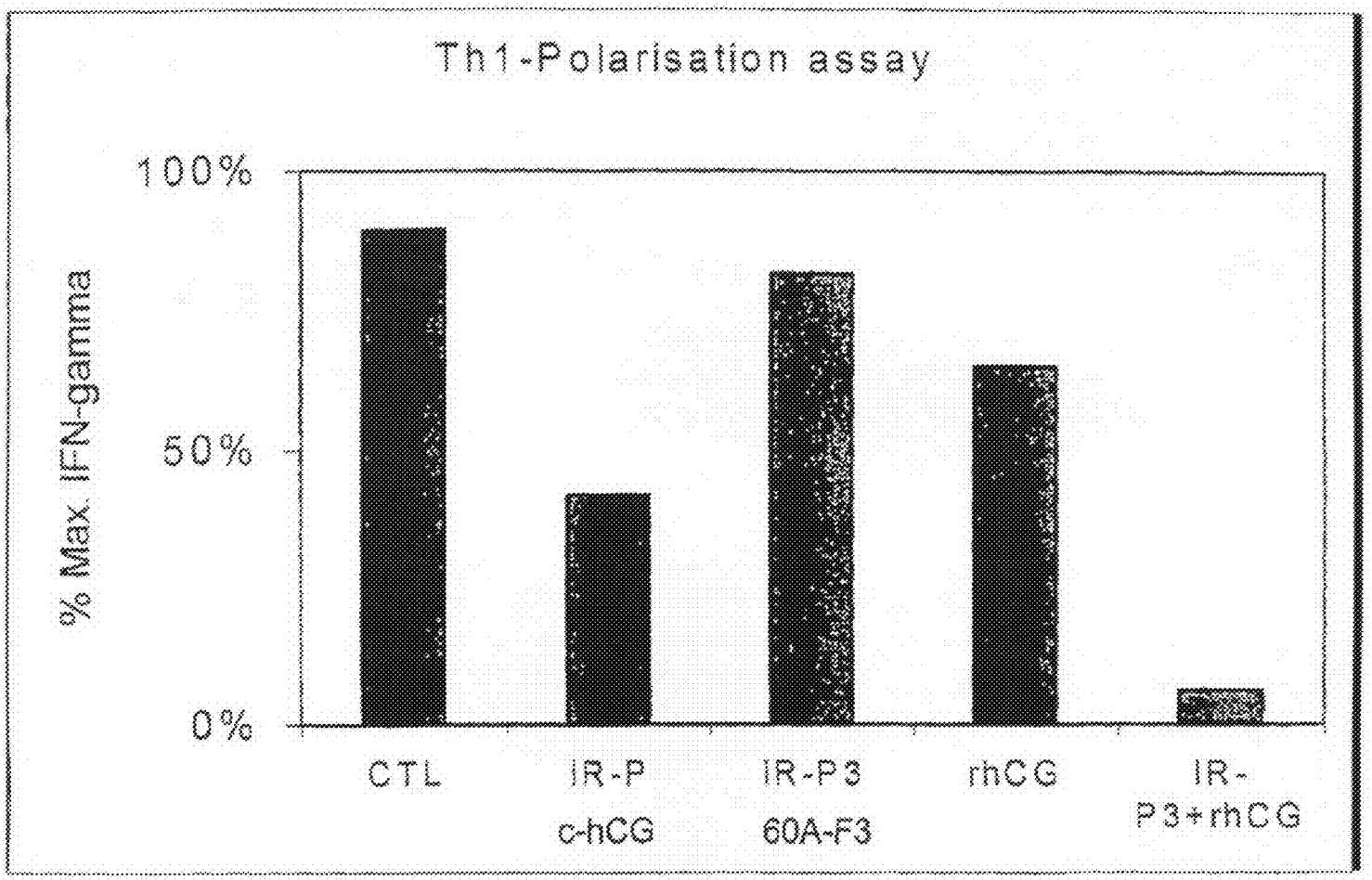
FIG. 32: This figure shows that there was moderate inhibition of IFN-gamma production found under Th1 polarisation conditions with 60A-F3 (c-hCG) and rhCG alone, while the outgrowth of Th1 cells was completely blocked with the combination of rhCG and 60A-F3 (c-hCG).
Figure 33:
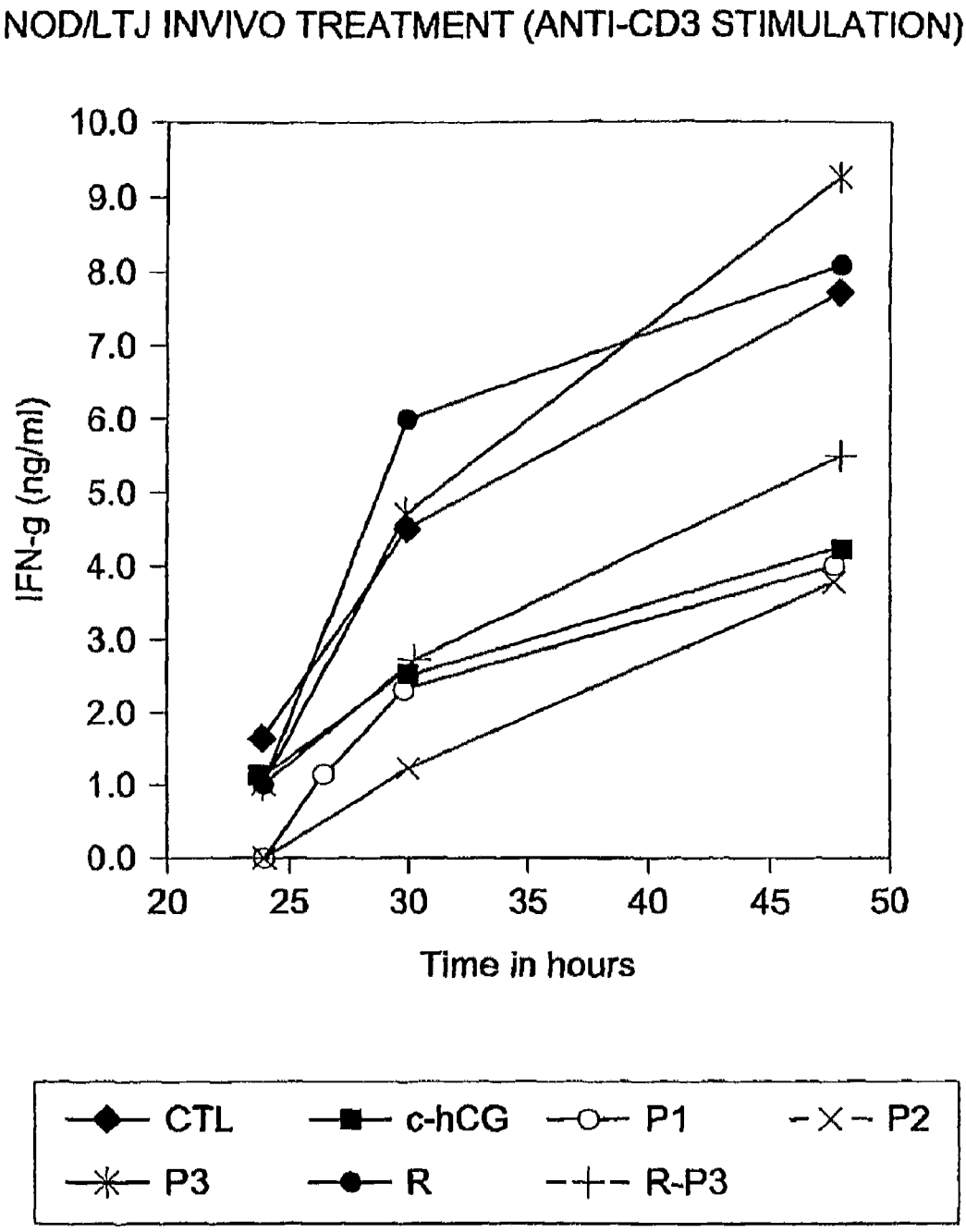
FIGS. 33-34: These figures show that anti-CD3 stimulated splenocytes from NOD mice treated with c-hCG, and 60A-F 1 have a smaller capacity to proliferate in vitro. Furthermore, splenocytes from 60A-F3 (IR-P3) and rhCG treated mice showed a higher capacity to proliferate as compared to the PBS treated control mice (CTL), while 60A-F3 (IR-P3) in combination with rhCG caused the same decrease in proliferation as c-hCG and 60A-F1 (IR-P 1) (FIG. 34). Moderate effect was found in the anti-CD3 stimulated proliferation of splenocytes from 60A-F2 treated NOD mice.
Figure 34:
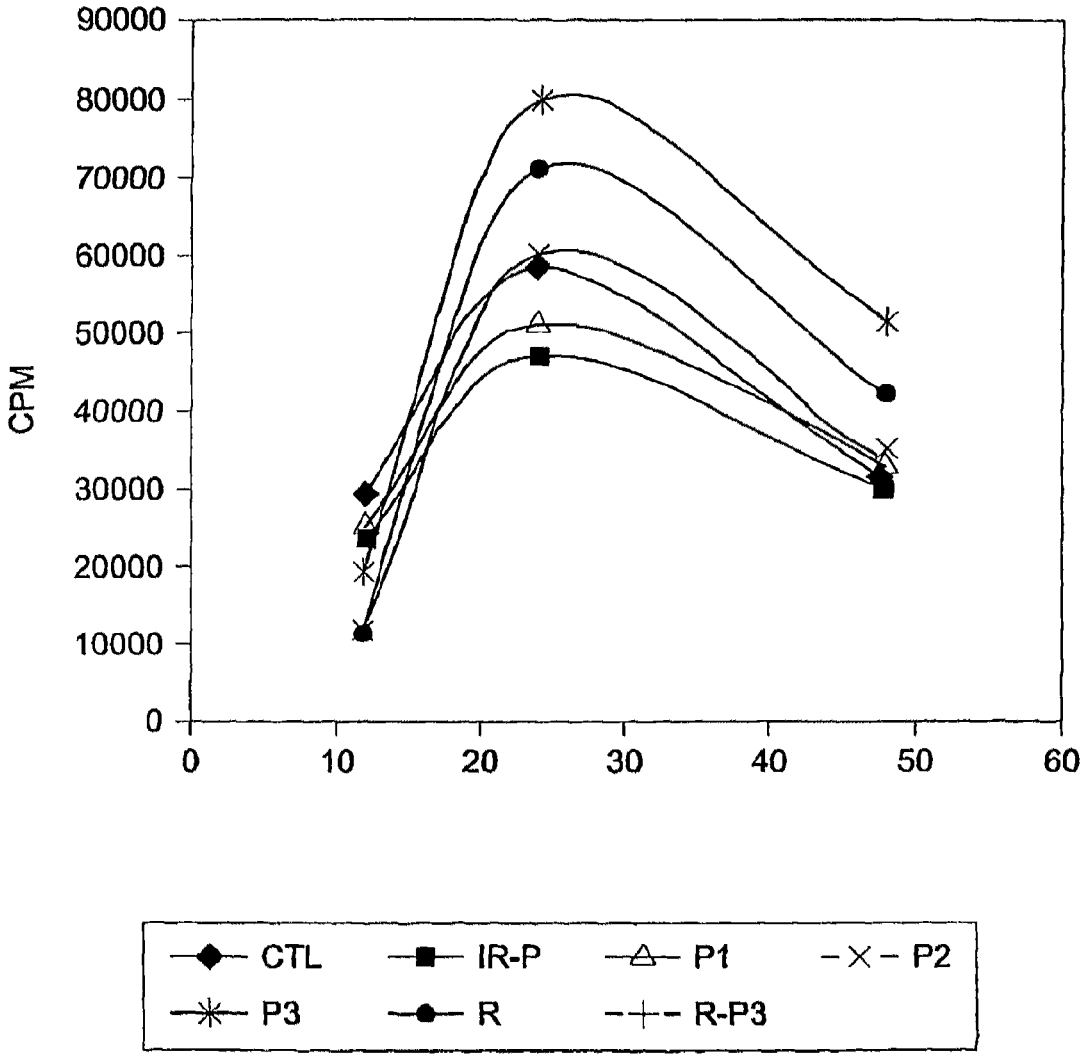
Figure 35:
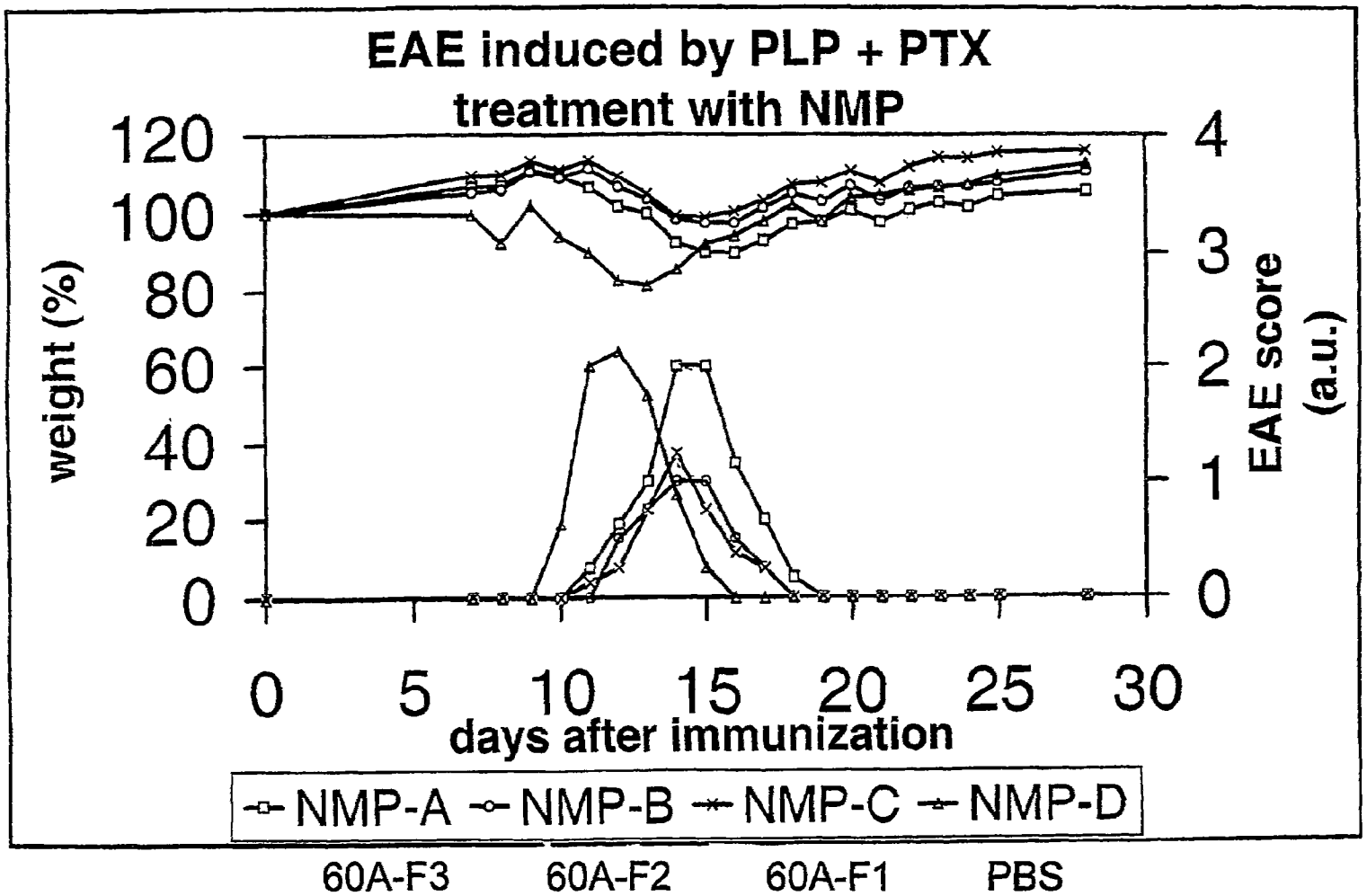
FIGS. 35-36: These figures show the effect of 60A-F1 (IR-P3), 60A-F2 (IR-P2) and 60A-F3 (IR-P3) in EAE model induced by PLP+PTX. In addition
Figure 36:
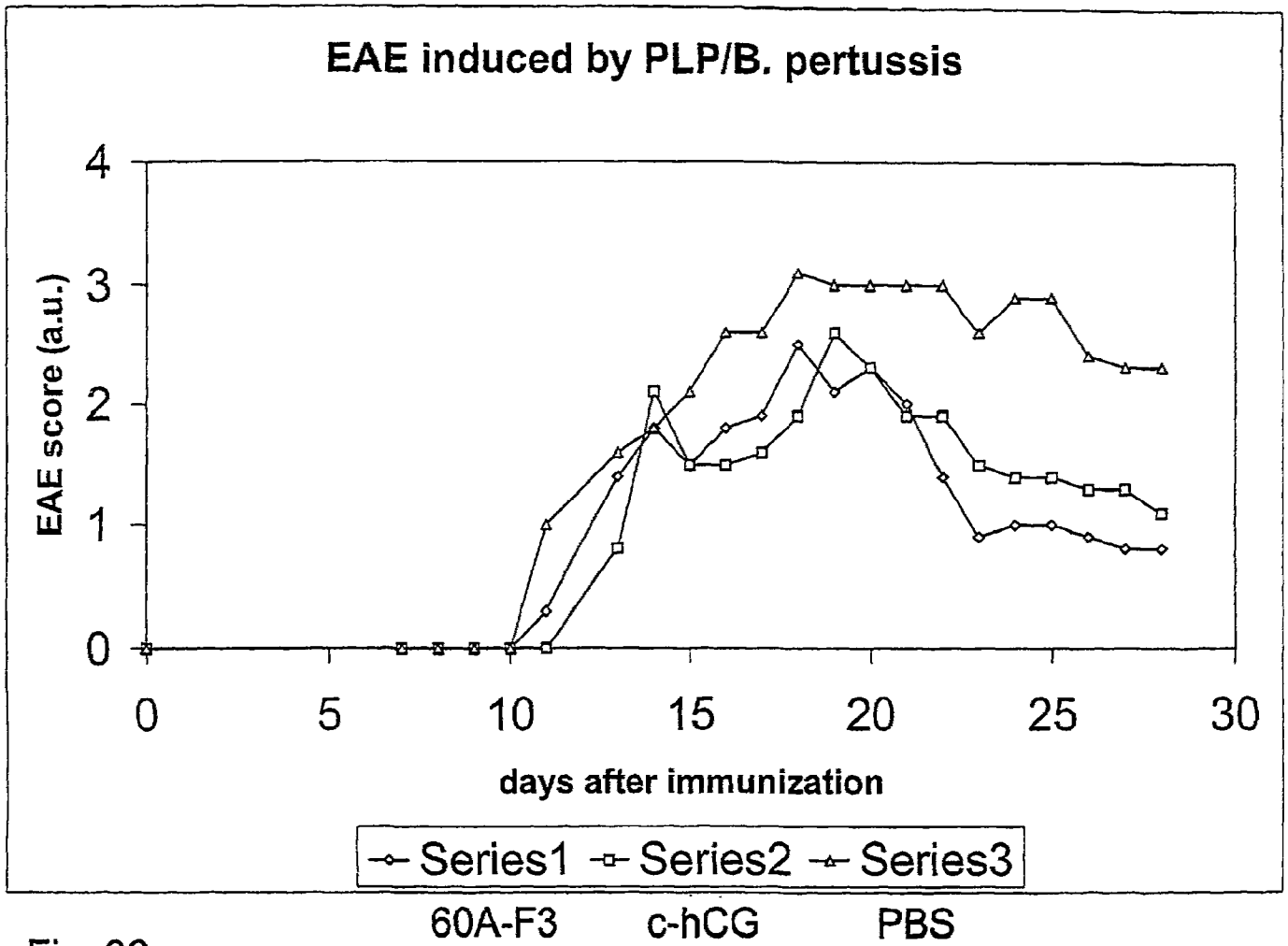

```
<160> NUMBER OF SEQ ID NOS: 30

<210> SEQ ID NO 1
<211> LENGTH: 17
<212> TYPE: PRT
<213> ORGANISM: Artificial Sequence
<220> FEATURE:
<221> NAME/KEY: SITE
<222> LOCATION: (1)..(17)
<223> OTHER INFORMATION: peptide obtainable or derivable from beta-HCG

<400> SEQUENCE: 1

Met Thr Arg Val Leu Gln Gly Val Leu Pro Ala Leu Pro Gln Val Val
1               5                   10                  15

Cys


<210> SEQ ID NO 2
<211> LENGTH: 13
<212> TYPE: PRT
<213> ORGANISM: Artificial Sequence
<220> FEATURE:
<221> NAME/KEY: SITE
<222> LOCATION: (1)..(13)
<223> OTHER INFORMATION: functional fragment of an immunoregulator of
      the invention

<400> SEQUENCE: 2

Leu Gln Gly Val Leu Pro Ala Leu Pro Gln Val Val Cys
1               5                   10


<210> SEQ ID NO 3
<211> LENGTH: 10
<212> TYPE: PRT
<213> ORGANISM: Artificial Sequence
<220> FEATURE:
<221> NAME/KEY: SITE
<222> LOCATION: (1)..(10)
<223> OTHER INFORMATION: functional fragment of an immunoregulator of
      the invention

<400> SEQUENCE: 3

Val Leu Pro Ala Leu Pro Gln Val Val Cys
1               5                   10


<210> SEQ ID NO 4
<211> LENGTH: 10
<212> TYPE: PRT
<213> ORGANISM: Artificial Sequence
<220> FEATURE:
<221> NAME/KEY: SITE
<222> LOCATION: (1)..(10)
<223> OTHER INFORMATION: functional fragment of an immunoregulator of
      the invention
```

<400> SEQUENCE: 4

Leu Gln Gly Val Leu Pro Ala Leu Pro Gln
1 5 10

<210> SEQ ID NO 5
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator

<400> SEQUENCE: 5

Met Thr Arg Val
1

<210> SEQ ID NO 6
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator

<400> SEQUENCE: 6

Gln Val Val Cys

<210> SEQ ID NO 7
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator

<400> SEQUENCE: 7

Cys Leu Gln Gly
1

<210> SEQ ID NO 8
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator

<400> SEQUENCE: 8

Leu Gln Gly Val
1

<210> SEQ ID NO 9
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: functional fragment of an immunoregulator of
the invention

<400> SEQUENCE: 9

Val Leu Pro Ala Leu Pro Gln
1 5

<210> SEQ ID NO 10
<211> LENGTH: 8
<212> TYPE: PRT
<213> ORGANISM: Artificial Sequence
<220> FEATURE:
<221> NAME/KEY: SITE
<222> LOCATION: (1)..(8)
<223> OTHER INFORMATION: functional fragment of an immunoregulator of
the invention

<400> SEQUENCE: 10

Gly Val Leu Pro Ala Leu Pro Gln
1 5

<210> SEQ ID NO 11
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: functional fragment of an immunoregulator of
the invention

<400> SEQUENCE: 11

Gly Val Leu Pro Ala Leu Pro
1 5

<210> SEQ ID NO 12
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: functional fragment of an immunoregulator of
the invention

<400> SEQUENCE: 12

Val Leu Pro Ala Leu Pro
1 5

<210> SEQ ID NO 13
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator

<400> SEQUENCE: 13

Pro Ala Leu Pro

<210> SEQ ID NO 14
<211> LENGTH: 13
<212> TYPE: PRT
<213> ORGANISM: Artificial Sequence
<220> FEATURE:
<221> NAME/KEY: SITE
<222> LOCATION: (1)..(13)
<223> OTHER INFORMATION: proteolipid protein peptide 139-151

<400> SEQUENCE: 14

His Ser Leu Gly Lys Trp Leu Gly His Pro Asp Lys Phe
1 5 10

<210> SEQ ID NO 15
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: ALA-replacement in peptide LQGV

<400> SEQUENCE: 15

Ala Gln Gly Val
1

<210> SEQ ID NO 16
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: ALA-replacement in peptide LQGV

<400> SEQUENCE: 16

Leu Gln Gly Ala
1

<210> SEQ ID NO 17
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: ALA-replacement in peptide VLPALP

<400> SEQUENCE: 17

Ala Leu Pro Ala Leu Pro
1 5

<210> SEQ ID NO 18
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: ALA-replacement in peptide VLPALP

<400> SEQUENCE: 18

Val Ala Pro Ala Leu Pro
1 5

<210> SEQ ID NO 19
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: ALA-replacement in peptide VLPALPQ

<400> SEQUENCE: 19

Ala Leu Pro Ala Leu Pro Gln
1 5

<210> SEQ ID NO 20
<211> LENGTH: 7
<212> TYPE: PRT
<213> ORGANISM: Artificial Sequence <220> FEATURE:
<221> NAME/KEY: SITE
<222> LOCATION: (1)..(7)
<223> OTHER INFORMATION: ALA-replacement in peptide VLPALPQ

<400> SEQUENCE: 20

Val Leu Pro Ala Ala Pro Gln
1 5

<210> SEQ ID NO 21
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: ALA-replacement in peptide VLPALPQ

<400> SEQUENCE: 21

Val Leu Pro Ala Leu Ala Gln
1 5

<210> SEQ ID NO 22
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: ALA-replacement in peptide LQGV

<400> SEQUENCE: 22

Leu Ala Gly Val
1

<210> SEQ ID NO 23
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: ALA-replacement in peptide LQGV

<400> SEQUENCE: 23

Leu Gln Ala Val
1

<210> SEQ ID NO 24
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: ALA-replacement in peptide VLPALP

<400> SEQUENCE: 24

Val Leu Ala Ala Leu Pro
1 5

<210> SEQ ID NO 25
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: ALA-replacement in peptide VLPALP

<400> SEQUENCE: 25

Val Leu Pro Ala Ala Pro
1 5

<210> SEQ ID NO 26
<211> LENGTH: 6
<212> TYPE: PRT
<213> ORGANISM: Artificial Sequence
<220> FEATURE:
<221> NAME/KEY: SITE
<222> LOCATION: (1)..(6)
<223> OTHER INFORMATION: ALA-replacement in peptide VLPALP

<400> SEQUENCE: 26

Val Leu Pro Ala Leu Ala
1 5

<210> SEQ ID NO 27
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: functional fragment of an immunoregulator of
the invention

<400> SEQUENCE: 27

Val Leu Pro Ala Leu Pro Gln
1 5

<210> SEQ ID NO 28
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: ALA-replacement in peptide VLPALPQ

<400> SEQUENCE: 28

Val Leu Ala Ala Leu Pro Gln
1 5

<210> SEQ ID NO 29
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: ALA-replacement in peptide VLPALPQ

<400> SEQUENCE: 29

Val Leu Pro Ala Leu Pro Ala
1 5

<210> SEQ ID NO 30
<211> LENGTH: 4
<212> TYPE: PRT
<213> ORGANISM: Artificial Sequence
<220> FEATURE:
<221> NAME/KEY: SITE
<222> LOCATION: (1)..(4)
<223> OTHER INFORMATION: third immunoregulator -continued

```
<400> SEQUENCE: 30

Leu Gln Gly Val
1
```

What is claimed is:

1. A purified immunoregulator consisting of LQGV (SEQ ID NO:8).

2. A pharmaceutical composition for treating an immune-mediated disorder in a subject comprising the immunoregulator of claim 1.

3. A pharmaceutical composition for treating a cardiovascular or circulatory disorder in a subject comprising the immunoregulator of claim 1.

4. A purified oligopeptide consisting of LQGV (SEQ ID NO:8).

5. A composition comprising the purified oligopeptide according to claim 4.

* * * * *

UNITED STATES PATENT AND TRADEMARK OFFICE

CERTIFICATE OF CORRECTION

PATENT NO. : RE43,140 E
APPLICATION NO. : 13/065318
DATED : January 24, 2012
INVENTOR(S) : Nisar Ahmed Khan and Robbert Benner It is certified that error appears in the above-identified patent and that said Letters Patent is hereby corrected as shown below:

On the title page:

In ITEM (56) References Cited
OTHER PUBLICATIONS

| | |
|---|---|
| Page 1, 2nd column, 1st line of the 4th entry (line 53), | change "NF-ΘB" to --NF-κB-- |
| Page 2, 2nd column, 1st line of the 1st entry (line 1), | change "from a women" to --from women-- |
| Page 2, 2nd column, 1st line of the 3rd entry (line 7), | change "Factor-ΘB" to --Factor-κB-- |
| Page 2, 2nd column, 1st line of the 4th entry (line 10), | change "NF-ΘB" to --NF-κB-- |
| Page 2, 2nd column, 1st line of the 14th entry (line 39), | change "Nisan" to --Nisar-- |

In the specification:

| | |
|---|---|
| COLUMN 33, LINE 12, | change "(SEQ ID NO:1)" to --(SEQ ID NO:2)-- |

Signed and Sealed this
Second Day of April, 2013

Teresa Stanek Rea
*Acting Director of the United States Patent and Trademark Office*